(12) United States Patent
Maier et al.

(10) Patent No.: US 7,990,533 B2
(45) Date of Patent: *Aug. 2, 2011

(54) SYSTEM AND METHOD FOR ANALYZING BIOLOGICAL SAMPLES USING RAMAN MOLECULAR IMAGING

(75) Inventors: John Maier, Pittsburgh, PA (US); Shona Stewart, Pittsburgh, PA (US); Jeffrey Cohen, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/834,370

(22) Filed: Jul. 12, 2010

(65) Prior Publication Data
US 2010/0280762 A1    Nov. 4, 2010

Related U.S. Application Data

(63) Continuation of application No. 12/206,467, filed on Sep. 8, 2008, now Pat. No. 7,755,757, which is a continuation-in-part of application No. 12/070,010, filed on Feb. 14, 2008, now Pat. No. 7,808,633.

(51) Int. Cl.
*G01J 3/44* (2006.01)
*G01N 21/65* (2006.01)

(52) U.S. Cl. .......................................... 356/301; 356/73

(58) Field of Classification Search .................. 356/301
See application file for complete search history.

(56) References Cited

U.S. PATENT DOCUMENTS

| 6,751,576 | B2 * | 6/2004 | Hall et al. | 702/183 |
| 7,755,757 | B2 * | 7/2010 | Maier et al. | 356/301 |
| 2002/0186875 | A1 * | 12/2002 | Burmer et al. | 382/133 |
| 2004/0068193 | A1 * | 4/2004 | Barnes et al. | 600/476 |

* cited by examiner

*Primary Examiner* — F. L Evans
(74) *Attorney, Agent, or Firm* — Morgan Lewis & Bockius LLP

(57) ABSTRACT

A system and method for determining at least one of: a disease state, a metabolic state, a clinical outcome, and a disease progression of a test renal or prostate sample. A test Raman data set is obtained from the sample wherein said test Raman data set may comprise at least one of a plurality of Raman spectra and a plurality of spatially accurate wavelength resolved Raman images. The test Raman data set is compared to a plurality of reference Raman data sets using a chemometric technique. For analysis of renal samples, each of these reference Raman data sets may have an associated known renal sample and an associated known metabolic state, clinical outcome, and/or disease progression. For analysis of prostate samples, each of these reference Raman data sets may have an associated known prostate sample and an associated known disease state, metabolic state, clinical outcome, and/or disease progression.

30 Claims, 38 Drawing Sheets

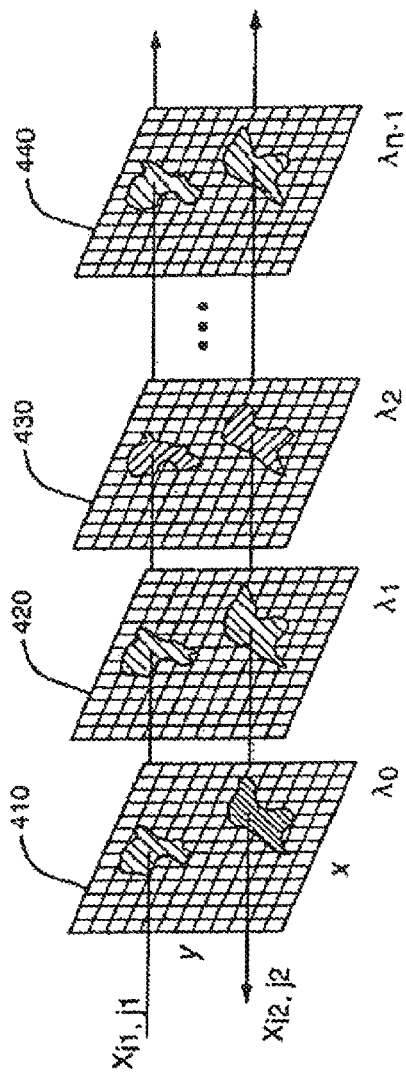
FIG. 4A
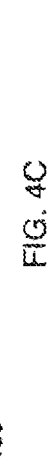
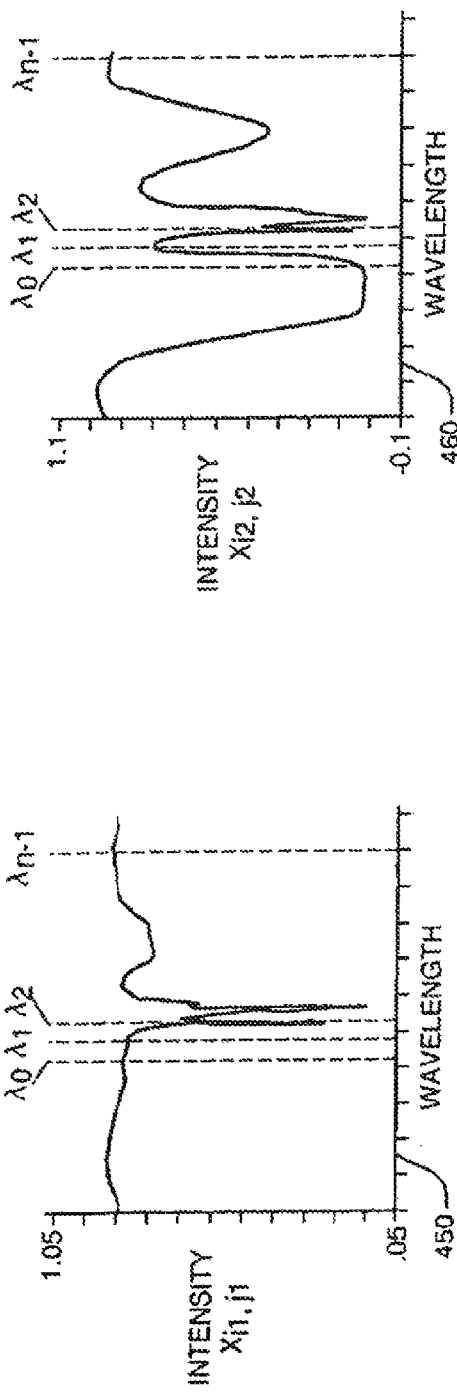
FIG. 4B
FIG. 4C

SYSTEM AND METHOD FOR ANALYZING BIOLOGICAL SAMPLES USING RAMAN MOLECULAR IMAGING

RELATED APPLICATIONS

This application is a continuation of U.S. patent application Ser. No. 12/206,467, filed on Sep. 8, 2008, entitled "Distinguishing Between Renal Oncocytoma and Chromophobe Renal Cell Carcinoma Using Raman Molecular Imaging," which itself claims the benefit of U.S. Provisional Application No. 60/971,940, filed Sep. 13, 2007, entitled "Distinguishing Between Renal Oncocytoma and Chromophobe Renal Cell Carcinoma Using Raman Molecular Imaging" U.S. patent application Ser. No. 12/206,467 is also continuation-in-part of U.S. patent application Ser. No. 12/070,010, filed Feb. 14, 2008. entitled "Spectroscopic System and Method for Prediction Disease Outcome" which claims the benefit of U.S. Provisional Application No. 60/901,497, filed Feb. 14, 2007, entitled "Method for Using Raman Scattered Light to Predict Clinical Outcome of Disease for Tissue Sample," and U.S. Provisional Application No. 60/896,236, filed Mar. 21, 2007, entitled "Spectroscopic System and Method for Predicting Progressive Outcome of Cancer Patients." Each of the above referenced patents and patent applications are hereby incorporated by reference in their entireties.

FIELD OF DISCLOSURE

The present disclosure relates to systems and methods for analyzing biological samples using Raman spectroscopy. The system and method disclosed herein may be applied to renal and/or prostate samples to determine at least one of: a disease state, a metabolic state, a clinical outcome, and a disease progression.

BACKGROUND

The biochemical composition of a cell is a complex mix of biological molecules including, but not limited to, proteins, nucleic acids, lipids, and carbohydrates. The composition and interaction of the biological molecules determines the metabolic state of a cell. The metabolic state of the cell will dictate the type of cell and its function (i.e., red blood cell, epithelial cell, etc.). Tissue is generally understood to mean a group of cells that work together to perform a function. Raman spectroscopic techniques provide information about the biological molecules contained in cells and tissues and therefore provide information about the metabolic state. As the cell's or tissue's metabolic state changes from the normal state to a diseased state, Raman spectroscopic techniques can provide information to indicate the metabolic change and therefore serve to diagnose and predict the outcome of a disease. Cancer is a prevalent disease, so physicians are very concerned with being able to accurately diagnose cancer and to determine the best course of treatment.

Raman spectroscopy may be explored for detection of various types of diseases in particular cancers. Because Raman spectroscopy is based on irradiation of a sample and detection of scattered radiation, it can be employed non-invasively to analyze biological samples in situ. Thus, little or no sample preparation is required. Raman spectroscopy techniques can be readily performed in aqueous environments because water exhibits very little, but predictable, Raman scattering. It is particularly amenable to in vivo measurements as the powers and excitation wavelengths used are non-destructive to the tissue and have a relatively large penetration depth.

Raman Molecular Imaging (RMI) is a reagentless tissue imaging approach based on the scattering of laser light from tissue samples. The approach yields an image of a sample wherein each pixel of the image is the Raman spectrum of the sample at the corresponding location. The Raman spectrum carries information about the local chemical environment of the sample at each location. RMI has a spatial resolving power of approximately 250 nm and can potentially provide qualitative and quantitative image information based on molecular composition and morphology.

The vast majority of diseases, in particular cancer cases, are pathologically diagnosed using tissue from a biopsy specimen. An experienced pathologist can provide diagnostic information used to make management decisions for the treatment of the cancer. In the case of renal disease, the diagnosis of renal oncocytoma (OC) and chromophobe renal cell carcinoma (ChRCC) based on histological features can often be challenging. Currently, there are no reliable immunohistochemical markers which separate these two neoplasms. Because OC is benign and ChRCC may behave aggressively, the correct identification of these diseases is crucial. A reliable method for distinguishing between OC and ChRCC may assist clinicians to improve prognoses and treatment options for patients with kidney disease.

Therefore it is desirable to devise methodologies that use Raman spectroscopy techniques to differentiate various cell types (e.g., normal, malignant, benign, etc.), to classify biological samples under investigation (e.g., a normal tissue, a diseased tissue, renal oncocytomas disease state and chromophobe renal cell carcinoma disease state), and to also predict clinical outcome (e.g., progressive or non-progressive state of cancer, etc.) of a diseased cell or tissue.

SUMMARY

The present disclosure provides for a method to provide a diagnosis of the renal disease state of a test renal sample. A group of known renal samples is provided where each known renal sample has an associated known renal disease state. The known renal disease state includes a renal oncocytoma disease state or a chromophobe renal cell carcinoma disease state. A Raman data set is obtained from each known renal sample. Each Raman data set is analyzed to identify a renal oncocytoma reference Raman data set or chromophobe renal cell carcinoma reference Raman data set depending on whether respective known renal sample is a renal oncocytoma sample or a chromophobe renal cell carcinoma sample. A first database is generated containing all renal oncocytoma reference Raman data sets. A second database is generated containing all chromophobe renal cell carcinoma reference Raman data sets. A test Raman data set of a test renal sample is obtained where the test renal sample has an unknown renal disease state. A diagnostic of whether the test renal sample has a renal oncocytoma disease state or a chromophobe renal cell carcinoma disease state is provided by comparing the test Raman data set against the reference Raman data sets in then first reference Raman and the second reference Raman databases using a chemometric technique.

The present disclosure further provides for yet another method to provide a diagnosis of the renal disease state of a test renal sample. A database containing a plurality of reference Raman data sets is provided where each reference Raman data set has an associated known renal sample and an associated known renal disease state. A test renal sample is irradiated with substantially monochromatic light to thereby generate scattered photons. A test Raman data set is collected based on the scattered photons. The test Raman data set is compared to the plurality of reference Raman data sets using a chemometric technique. Based on the comparison, a diagnosis of a renal disease state of the test renal sample is provided.

In one such embodiment, the known renal disease state includes a renal oncocytoma disease state or a chromophobe renal cell carcinoma disease state.

In another such embodiment, the reference Raman data sets includes a plurality of reference Raman spectra obtained from the one or more regions of interest of the known renal sample.

In still another such embodiment, the test Raman data set has at least one of the following associated therewith: a corresponding test Raman image; and a corresponding test non-Raman image.

In still yet another embodiment, the test Raman image is used to identify one or more regions of interest of the test renal sample, wherein the one or more regions of interest contain at least one of the following: an epithelium tissue, a stroma tissue, and a nuclei tissue of said test renal sample. From the one or more regions of interest, a plurality of test Raman spectra are obtained for the test renal sample.

In one embodiment, the chemometric technique is at least one of the following: Principal Component Analysis, Minimum noise function, spectral mixture resolution, and linear discriminant analysis. In one such embodiment, the chemometric technique is Principal Component analysis in which the analysis is performed by selecting a pre-determined vector space that mathematically describes the plurality of reference Raman data sets. The test Raman data set is transformed into the pre-determined vector space. A distribution of transformed data in the pre-determined vector space is analyzed so to generate the renal disease state diagnosis.

In one embodiment, the analysis of the transformed data distribution is performed by using a classification scheme. The classification scheme includes at least one of the following: Mahalanobis distance, Adaptive subspace detector, Band target entropy method, Neural network, and support vector machine. When the classification scheme is Mahalanobis distance, a Mahalanobis distance is calculated between the test Raman data set transformed into the pre-determined vector space and the plurality of reference Raman data sets in the pre-determined vector space so to generate the renal disease state diagnosis.

The present disclosure further provides for a system to provide a diagnosis of the renal disease state of a test renal sample. The system includes a reference database, an illumination source, a spectroscopic device, a machine readable program code and a processor. The reference database contains a plurality of reference Raman data sets, each reference Raman data set has an associated known renal sample and an associated known renal disease state. The illumination source is configured to illuminate a test renal sample with substantially monochromatic light to generate scattered photons. The spectroscopic device is configured to collect a test Raman data set based on the scattered photons. The machine readable program code contains executable program instructions. The processor is operatively coupled to the illumination source and the spectroscopic device, and configured to execute the machine readable program code so to perform a series of steps. In one embodiment, the spectroscopic device includes an imaging spectrometer. In another embodiment, the spectroscopic device includes a dispersive spectrometer and a fiber array spectral translator.

The present disclosure further provides for a storage medium containing machine readable program code, which, when executed by a processor, causes the processor to perform a series of steps. An irradiation source is configured to irradiate a test renal sample with substantially monochromatic light to thereby generate scattered photons. A spectroscopic device is configured to collect a test Raman data set based on the scattered photons. The test Raman data set is compared to a plurality of reference Raman data sets using a chemometric technique. Based on the comparison, a renal disease state of the test renal sample is diagnosed.

The present disclosure further provides for a method to generate a diagnosis of renal disease state where a test Raman data set from a test renal sample is generated at a data generation site remote from an analysis center. The test Raman data set is transmitted over a data communication network to an analysis center. A database is provided at the analysis center where the database contains a plurality of reference Raman data sets, each reference Raman data set has an associated known renal sample and an associated known renal disease state. The test Raman data set is compared to the plurality of reference Raman data sets at the analysis center using a chemometric technique. Based on the comparison, a renal disease state of the test renal sample is diagnosed. The diagnosis is transmitted to the data generation site via the data communication network.

The present disclosure further yet provides for a system to generate a diagnosis of renal disease state of a test renal sample. The system includes a data generation site, a communication interface, an analysis site, a database, a machine readable program code, and a processor. The data generation site has one or more spectroscopic devices which generate a test Raman data set for a test renal sample. The communication interface links the data generation site to a data analysis site. The database at the analysis site contains a plurality of reference Raman data sets, each reference Raman data set has an associated known renal sample and an associated known renal disease state. The machine readable program code, at the data analysis site, contains executable program instructions. The processor, at the data analysis site, is operatively coupled to the communication interface, and is configured to execute the machine readable program code to perform a series of steps including: facilitate transfer of the test Raman data set from the data generation site to the data analysis site via the communication interface; compare the test Raman data set to the plurality of reference Raman data sets using a chemometric technique; based on said comparison, diagnose a renal disease state of the test renal sample; and transfer the diagnosis to the data generation site via the data communication network. In one such embodiment, the spectroscopic device includes an imaging spectrometer. In another such embodiment, the spectroscopic device includes a dispersive spectrometer and a fiber array spectral translator.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings:

FIGS. 4A-4C illustrate a Raman data set of one embodiment;

DETAILED DESCRIPTION OF THE DISCLOSURE

Reference will now be made in detail to the preferred embodiments of the present disclosure, examples of which are illustrated in the accompanying drawings. Wherever possible, the same reference numbers will be used throughout the drawings to refer to the same or like parts.

Raman spectroscopy has utility in differentiating normal vs. malignant tissue and differentiating normal vs. benign tissue. In the case of breast cancer, the Raman spectra of malignant and benign tissues show an increase in protein content and a decrease in lipid content versus normal breast tissue. These results demonstrate that cancer disease states have a molecular basis for their origin. This method is not limited to the prediction of the clinical outcome of cancer as the molecular basis for other disease states can also be detected by Raman spectroscopy. Despite the reported ability to differentiate tissue types, there are no reports describing the use of Raman spectroscopy to diagnosis a renal sample as having a renal oncocytoma ("OC") disease state or a chromophobe renal cell carcinoma ("ChRCC") disease state.

The systems and methods described herein can potentially be utilized by a decision maker, such as pathologist, to identify type of kidney disease in cases where existing lesions have overlapping histopathologic features of OC and ChRCC. Because these diseases have different prognoses and treatments, correctly identifying them has major implications for the health of patients.

Figure 1:
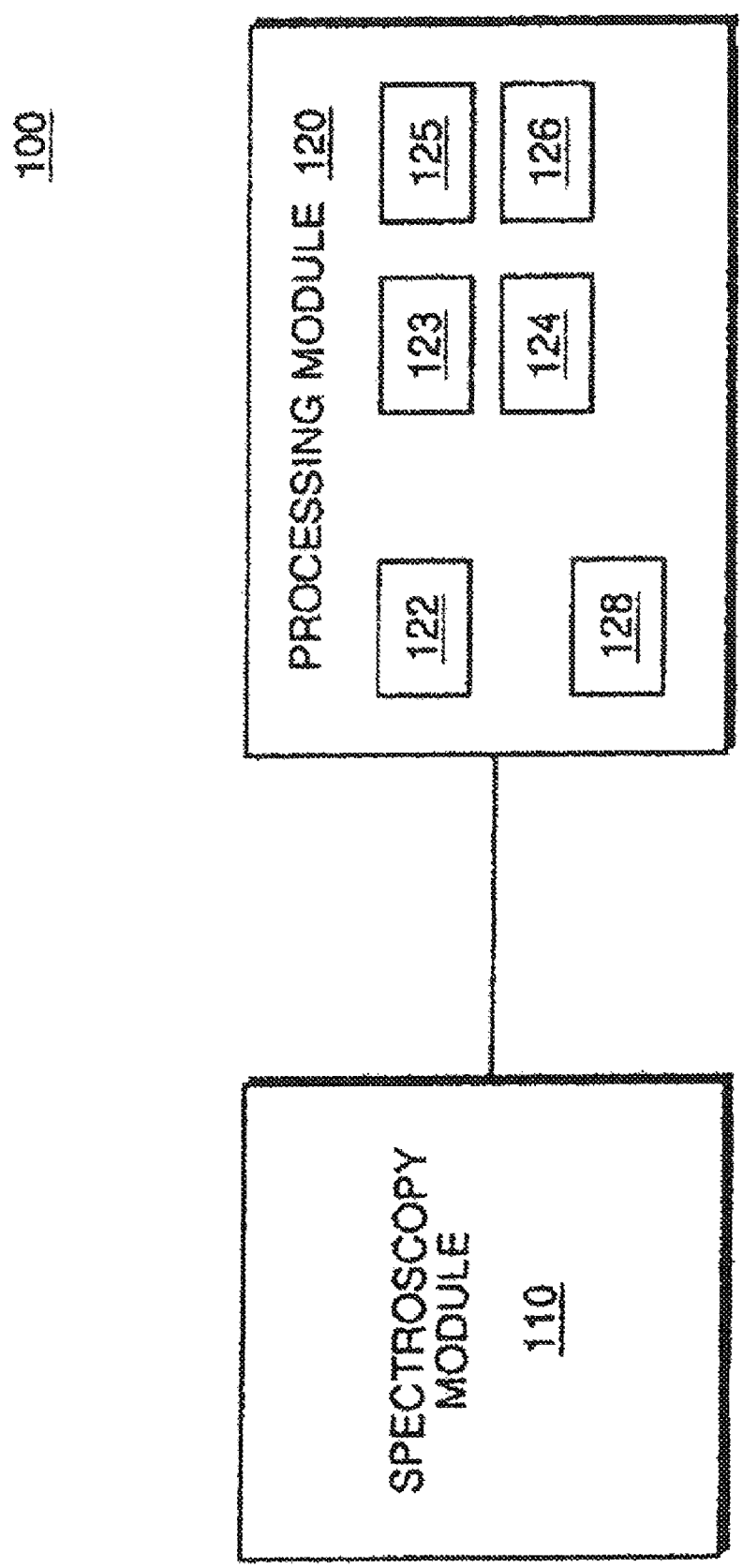
FIG. 1 schematically represents an exemplary system of the present disclosure.

FIG. 1 illustrates an exemplary system 100 according to one embodiment of the present disclosure. System 100 includes a spectroscopy module 110 in communication with a processing module 120. Processing module 120 may include a processor 122, databases 123, 124, 125 and 126, and machine readable program code 128. The machine readable program code 128 may contain executable program instructions, and the processor 122 may be configured to execute the machine readable program code 128 so as to perform the methods of the present disclosure. In one embodiment, the program code 128 may contain the ChemImage Xpert™ software marketed by ChemImage Corporation of Pittsburgh, Pa. The Xpert™ software may be used to process spectroscopic data and information received from the spectroscopy module 110 to obtain various spectral plots and images, and to also carry out various multivariate image analysis methods discussed later herein below.

Figure 2A:
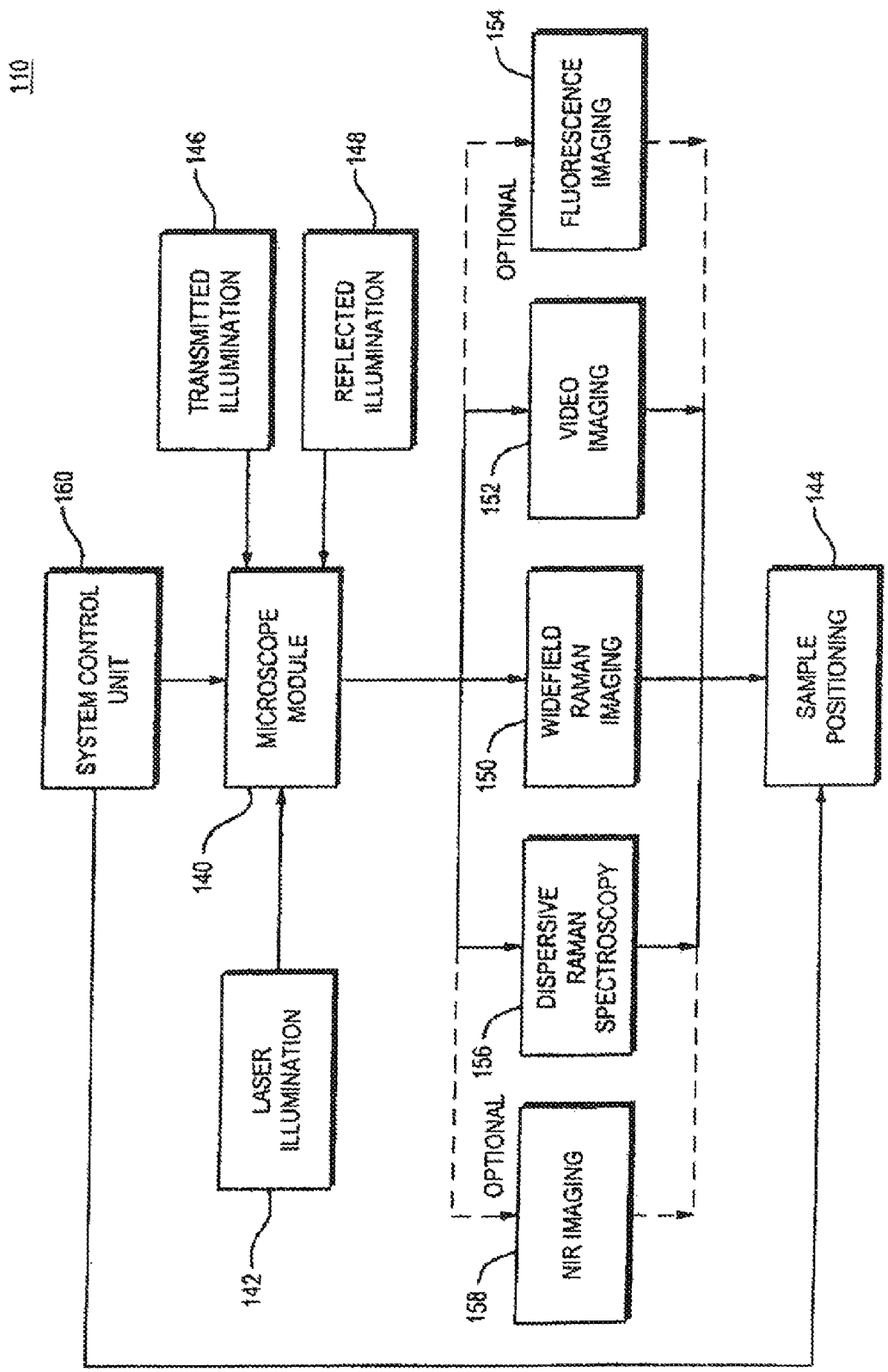
FIGS. 2A and 2B schematically represent an exemplary spectroscopy module of the present disclosure.

FIG. 2A illustrates an exemplary schematic layout of the spectroscopy module 110 shown in FIG. 1. The layout in FIG.

2A may relate to the Falcon II™ Raman chemical imaging system marketed by ChemImage Corporation of Pittsburgh, Pa. In one embodiment, the spectroscopy module 110 may include a microscope module 140 containing optics for microscope applications. An illumination source 142 (e.g., a laser illumination source) may provide illuminating photons to a sample (not shown) handled by a sample positioning unit 144 via the microscope module 140. In one embodiment, photons transmitted, reflected, emitted, or scattered from the illuminated sample (not shown) may pass through the microscope module (as illustrated by exemplary blocks 146, 148 in FIG. 2A) before being directed to one or more of spectroscopy or imaging optics in the spectroscopy module 110. In the embodiment of FIG. 2A, dispersive Raman spectroscopy 156, widefield Raman imaging 150, and brightfield video imaging 152 are illustrated as "standard" operational modes of the spectroscopy module 110. Two optional imaging modes—fluorescence imaging 154 and NIR (Near Infrared) imaging 158—may also be provided if desired. The spectroscopy module 110 may also include a control unit 160 to control operational aspects (e.g., focusing, sample placement, laser beam transmission, etc.) of various system components including, for example, the microscope module 140 and the sample positioning unit 144 as illustrated in FIG. 2A. In one embodiment, operation of various components (including the control unit 160) in the spectroscopy module 110 may be fully automated or partially automated, under user control.

It is noted here that in the discussion herein the terms "illumination," "illuminating," "irradiation," and "excitation" are used interchangeably as can be evident from the context. For example, the terms "illumination source," "light source," and "excitation source" are used interchangeably. Similarly, the terms "illuminating photons" and "excitation photons" are also used interchangeably. Furthermore, although the discussion hereinbelow focuses more on Raman spectroscopy and Raman molecular imaging, various methodologies discussed herein may be adapted to be used in conjunction with other types of spectroscopy applications as can be evident to one skilled in the art based on the discussion provided herein.

Figure 2B:
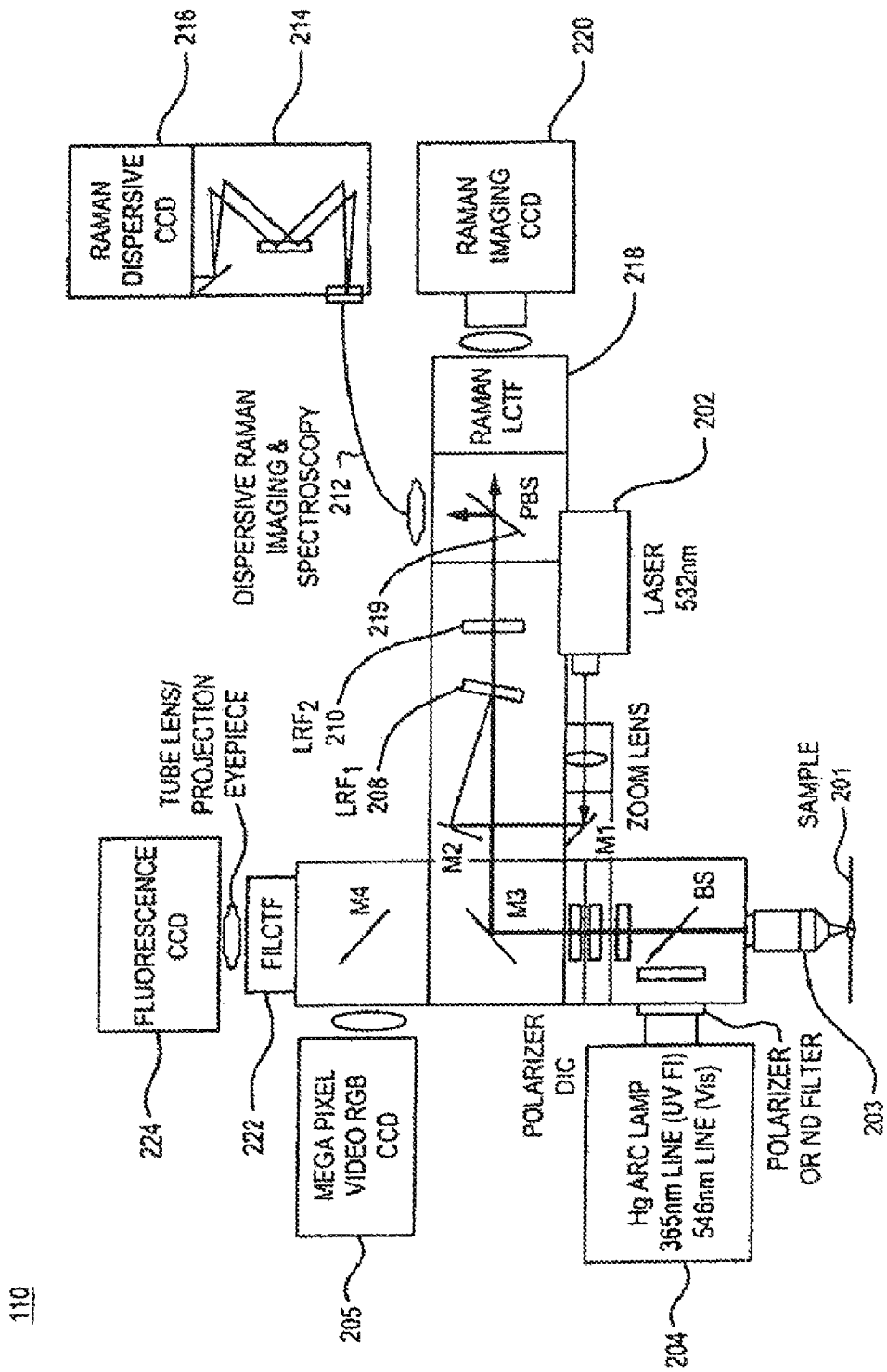

FIG. 2B illustrates exemplary details of the spectroscopy module 110 in FIG. 2A according to one embodiment of the present disclosure. Spectroscopy module 110 may operate in several experimental modes of operation including bright field reflectance and transmission imaging, polarized light imaging, differential interference contrast (DIC) imaging, UV induced autofluorescence imaging, NIR imaging, wide field illumination whole field Raman spectroscopy, wide field spectral fluorescence imaging, and wide field spectral Raman imaging. Module 110 may include collection optics 203, light sources 202 and 204, and a plurality of spectral information processing devices including, for example: a tunable fluorescence filter 222, a tunable Raman filter 218, a dispersive spectrometer 214, a plurality of detectors including a fluorescence detector 224, and Raman detectors 216 and 220, a fiber array spectral translator ("FAST") device 212, filters 208 and 210, and a polarized beam splitter (PBS) 219. In one embodiment, the processor 122 (FIG. 1) may be operatively coupled to light sources 202 and 204, and the plurality of spectral information processing devices 214, 218 and 222. In another embodiment, the processor 122 (FIG. 1), when suitably programmed, can configure various functional parts of the spectroscopy module in FIG. 1 and may also control their operation at run time. The processor, when suitably programmed, may also facilitate various remote data transfer and analysis operations discussed in conjunction with FIG. 3. Module 110 may optionally include a video camera 205 for video imaging applications. Although not shown in FIG. 2B, spectroscopy module 110 may include many additional optical and electrical components to carry out various spectroscopy and imaging applications supported thereby.

A sample 201 may be placed at a focusing location (e.g., by using the sample positioning unit 144 in FIG. 2A) to receive illuminating photons and to also provide reflected, emitted, scattered, or transmitted photons from the sample 201 to the collection optics 203. Sample 201 may include a variety of biological samples. In one embodiment, the sample 201 includes at least one cell or a tissue containing a plurality of cells. The sample may contain normal (non-diseased or benign) cells, diseased cells (e.g., cancerous tissues with or without a progressive cancer state or malignant cells with or without a progressive cancer state) or a combination of normal and diseased cells. In one embodiment, the cell/tissue is a mammalian cell/tissue. Some examples of biological samples may include prostate cells, kidney cells, lung cells, colon cells, bone marrow cells, brain cells, red blood cells, and cardiac muscle cells. In one embodiment, the biological sample may include prostate cells. In one such embodiment, the biological sample may include Gleason 6 prostate cells: In another such embodiment, the biological sample may include Gleason 7 prostate cells. In another embodiment the biological sample may include a renal sample. In one such embodiment, the biological sample may include renal oncocytoma cells. In another such embodiment, the biological sample may include chromophobe renal carcinoma. In another embodiment, the sample 201 may include cells of plants, non-mammalian animals, fungi, protists, and monera. In yet another embodiment, the sample 201 may include a test sample (e.g., a biological sample under test to determine its metabolic state or its disease status or to determine whether it is cancerous state would progress to the next level). The "test sample," "target sample" or unknown sample are used interchangeably herein to refer to a biological sample or renal sample under investigation, wherein such interchange use may be without reference to such biological sample's metabolic state or disease status.

A progressive cancer state is a cancer that will go on to become aggressive and acquire subsequent treatment by more aggressive means in order for the patient to survive. An example of progressive cancer is a Gleason score 7 cancer found in a prostate which has been surgically removed, where the patient, subsequent to the removal of the prostate, develops metastatic cancer. In this example the cancer progressed even after the removal of the source organ. Progressive cancers can be detected and identified in other organs and different types of cancer.

A non-progressive cancer is a cancer that does not progress to more advanced disease, requiring aggressive treatment. Many prostate cancers are non-progressive by this definition because though they are cancer by standard histopathological definition, they do not impact the life of the patient in a way that requires significant treatment. In many cases such cancers are observed and treated only if they show evidence of becoming progressive. Again, this is not a state particular to prostate cancer. Cancer cells are present in tissues of many health people. Because these do not ever transition to a state where they become progressive in terms of growth, danger to the patient, or inconvenience to the patient they would be considered non-progressive as the term is used herein.

The designation of progressive vs. non progressive can also be extended to other disease or metabolic states. As an example, diabetes can be clinically described as "stable", "well managed" by a clinician and would fall into the non-progressive class. In contrast diabetes can be progressing through the common course of the disease with all of the effects on kidneys, skin, nerves, heart and other organs which are part of the disease. As a second example multiple sclerosis is a disease which exists in many people is a stable, non-progressive state. In some people the disease rapidly progresses through historically observed pattern of physical characteristics with clinical manifestations.

The cells can be isolated cells, such as individual blood cells or cells of a solid tissue that have been separated from other cells of the tissue (e.g., by degradation of the intracellular matrix). The cells can also be cells present in a mass, such as a bacterial colon/.y grown on a semi-solid medium or an intact or physically disrupted tissue. By way of example, blood drawn from a human can be smeared on the surface of a suitable Raman scattering substrate (e.g., an aluminum-coated glass slide) and individual cells in the sample can be separately imaged by light microscopy and Raman scattering analysis using the spectroscopy module 110 of FIG. 2B. Similarly a slice of a solid tissue (e.g., a piece of fresh tissue or a paraffin-embedded thin section of a tissue) can be imaged on a suitable surface.

The cells can be cells obtained from a subject (e.g., cells obtained from a human blood or urine sample, semen sample, tissue biopsy, or surgical procedure). Cells can also be studied where they naturally occur, such as cells in an accessible location (e.g., a location on or within a human body), cells in a remote location using a suitable probe, or by revealing cells (e.g., surgically) that are not normally accessible.

Referring again to FIG. 2B, light source 202 may be used to irradiate the sample 201 with substantially monochromatic light. Light source 202 can include any conventional photon source, including, for example, a laser, an LED (light emitting diode), or other IR (infrared) or near IR (NIR) devices. The substantially monochromatic radiation reaching sample 201 illuminates the sample 201, and may produce photons scattered from different locations on or within the illuminated sample 201. A portion of the Raman scattered photons from the sample 201 may be collected by the collection optics 203 and directed to dispersive spectrometer 214 or Raman tunable filter 218 for further processing discussed later herein below. In one embodiment, light source 202 includes a laser light source producing light at 532.1 nm. The laser excitation signal is focused on the sample 201 through combined operation of reflecting mirrors M1, M2, M3, the filter 208, and the collection optics 203 as illustrated by an exemplary optical path in the embodiment of FIG. 2B. The filter 208 may be tilted at a specific angle from the vertical (e.g., at 6.50°) to reflect laser illumination onto the mirror M3, but not to reflect Raman-scattered photons received from the sample 201. The other filter 210 may not be tilted (i.e., it remains at 0° from the vertical). Filters 208 and 210 may function as laser line rejection filters to reject light at the wavelength of laser light source 202.

In the spectroscopy module 110 in the embodiment of FIG. 2B, the second light source 204 may be used to irradiate the sample 201 with ultraviolet light or visible light. In one embodiment, the light source 204 includes a mercury arc (Hg arc) lamp that produces ultraviolet radiation (UV) having wavelength at 365 nm for fluorescence spectroscopy applications. In yet another embodiment, the light source 204 may produce visible light at 546 nm for visible light imaging applications. A polarizer or neutral density (ND) filter with or without a beam splitter (BS) may he provided in front of the light source 204 to obtain desired illumination light intensity and polarization.

In the embodiment of FIG. 2B, the dispersive spectrometer 214 and the Raman tunable filter 218 function to produce Raman data sets of sample 201. A Raman data set corresponds to one or more of the following: a plurality of Raman spectra of the sample; and a plurality of spatially accurate wavelength resolved Raman images of the sample. In one embodiment, the plurality of Raman spectra is generated by dispersive spectral measurements of individual cells. In this embodiment, the illumination of the individual cell may cover the entire area of the cell so the dispersive Raman spectrum is an integrated measure of spectral response from all the locations within the cell.

In another embodiment, the Raman data set corresponds to a three dimensional block of Raman data (e.g., a spectral hypercube or a Raman image) having spatial dimensional data represented in the x and y dimensions and wavelength data represented in the z dimension as exemplified in FIGS. 4A-4C. Each Raman image has a plurality of pixels where each has a corresponding x and y position in the Raman image. The Raman image may have one or more regions of interest. The regions of interest may be identified by the size and shape of one or more pixels and is selected where the pixels are located within the regions of interest. A single Raman spectrum is then extracted from each pixel located in the region of interest, leading to a plurality of Raman spectra for each of the regions of interest. The extracted plurality of Raman spectra are then designated as the Raman data set. In this embodiment, the plurality of Raman spectra and the plurality of spatially accurate wavelength resolved Raman images are generated, as components of the hypercube, by a combination of the Raman tunable filter 218 and Raman imaging detector 220 or by a combination of the FAST device 212, the dispersive spectrometer 214, and the Raman detector 216.

In yet another embodiment, a Raman dataset is generated using a Raman image to identify one or more regions of interest of the sample 201. In one such embodiment, the one or more regions of interest contain at least one of the following: an epithelium area, a stroma area, epithelial-stromal junction (ESJ) area and/or nuclei area. A plurality of Raman spectra may be obtained from the one or more regions of interest of the sample 201. In standard operation the Raman spectrum generated by selecting a region of interest in a Raman image is the average spectrum of all the spectra at each pixel within the region of interest. The standard deviation between of all the spectra in the region of interest may be displayed along with the average Raman spectrum of the region of interest. Alternatively, all of the spectra associated with pixels within a region can be considered as a plurality of spectra, without the step of reducing them to a mean and standard deviation.

With further reference to FIG. 2B, the fluorescence tunable filter 222 may function to produce fluorescence data sets of the photons emitted from the sample 201 under suitable illumination (e.g., UV illumination). In one embodiment, the fluorescence data set includes a plurality of fluorescence spectra of sample 201 and/or a plurality of spatially accurate wavelength resolved fluorescence images of sample 201. A fluorescence spectrum of sample 210 may contain a fluorescence emission signature of the sample 201. In one embodiment, the emission signature may be indicative of a fluorescent probe (e.g., fluorescein isothiocyanate) within the sample 201. The fluorescence data sets may be detected by fluorescence CCD detector 224. A portion of the fluorescence emitted photons or visible light reflected photons from the sample 201 may be directed to the video imaging camera 205 via a mirror M4 and appropriate optical signal focusing mechanism.

In one embodiment, a microscope objective (including the collection optics 203) may be automatically or manually zoomed in or out to obtain proper focusing of the sample.

The entrance slit (not shown) of the spectrometer 214 may be optically coupled to the output end of the fiber array spectral translator device 212 to disperse the Raman scattered photons received from the FAST device 212 and to generate a plurality of spatially resolved Raman spectra from the wavelength-dispersed photons. The FAST device 212 may receive Raman scattered photons from the beam splitter 219, which may split and appropriately polarize the Raman scattered photons received from the sample 201 and transmit corresponding portions to the input end of the FAST device 212 and the input end of the Raman tunable filter 218.

Referring again to FIG. 2B, the tunable fluorescence filter 222 and the tunable Raman filter 218 may be used to individually tune specific photon wavelengths of interest and to thereby generate a plurality of spatially accurate wavelength resolved spectroscopic fluorescence images and Raman images, respectively, in conjunction with corresponding detectors 224 and 220. In one embodiment, each of the fluorescence filter 222 and the Raman filter 218 includes a two-dimensional tunable filter, such as, for example, an electro-optical tunable filter, a liquid crystal tunable filter (LCTF), or an acousto-optical tunable filter (AOTF). A tunable filter may be a band-pass or narrow band filter that can sequentially pass or "tune" fluorescence emitted photons or Raman scattered photons into a plurality of predetermined wavelength bands. The plurality of predetermined wavelength bands may include specific wavelengths or ranges of wavelengths. In one embodiment, the predetermined wavelength bands may include wavelengths characteristic of the sample undergoing analysis. The wavelengths that can be passed through the fluorescence filter 222 and Raman filter 218 may range from 200 nm (ultraviolet) to 2000 nm (i.e., the far infrared). The choice of a tunable filter depends on the desired optical region and/or the nature of the sample being analyzed. Additional examples of a two-dimensional tunable filter may include a Fabry Perot angle tuned filter, a Lyot filter, an Evans split element liquid crystal tunable filter, a Solc liquid crystal tunable filter, a spectral diversity filter, a photonic crystal filter, a fixed wavelength Fabry Perot tunable filter, an air-tuned Fabry Perot tunable filter, a mechanically-tuned Fabry Perot tunable filter, and a liquid crystal Fabry Perot tunable filter. As noted before, the tunable filters 218, 222 may be selected to operate in one or more of the following spectral ranges: the ultraviolet (UV), visible, and near infrared. In one such embodiment, the tunable filters 218, 222 may be selected to operate in spectra ranges of 900-1155 $cm^{-1}$ and 15-30-1850 $cm^{-1}$ Raman shift values.

In one embodiment, a multi-conjugate filter (MCF) may be used instead of a simple LCTF (e.g., the LCTF 218 or 222) to provide more precise wavelength tuning of photons received from the sample 201. Some exemplary multi-conjugate filters are discussed, for example, in U.S. Pat. No. 6,992,809, titled "Multi-Conjugate Liquid Crystal Tunable Filter;" and in the United States Published Patent Application Number US2007/0070260A1, titled "Liquid Crystal Filter with Tunable Rejection Band," the disclosures of both of these publications are incorporated herein by reference in their entireties.

In the embodiment of FIG. 2B, the fluorescence spectral data sets (output from the tunable filter 222) may be detected by the detector 224, and the Raman spectral data sets (output from the spectrometer 214 and the tunable filter 218) may be detected by detectors 216 and 220. The detectors 216, 220, and 224 may detect received photons in a spatially accurate manner. Detectors 216, 220 and 224 may include an optical signal (or photon) collection device such as, for example, an image focal plane array (FPA) detector, a charge coupled device (CCD) detector, or a CMOS (Complementary Metal Oxide Semiconductor) array sensor. Detectors 216, 220 and 224 may measure the intensity of scattered, transmitted or reflected light incident upon their sensing surfaces (not shown) at multiple discrete locations or pixels, and transfer the spectral information received to the processor module 120 for storage and analysis. The optical region employed to characterize the sample of interest governs the choice of two-dimensional array detector. For example, a two-dimensional array of silicon charge-coupled device (CCD) detection elements can be employed with visible wavelength emitted or reflected photons, or with Raman scatter photons, while gallium arsenide (GaAs) and gallium indium arsenide (GaInAs) FPA detectors can be employed for image analyses at near infrared wavelengths. The choice of such devices may also depend on the type of sample being analyzed.

In one embodiment, a display unit (not shown) may be provided to display spectral data collected by various detectors 216, 220, 224 in a predefined or user-selected format. The display unit may be a computer display screen, a display monitor, an LCD (liquid crystal display) screen, or any other type of electronic display device.

Referring again to FIG. 1, the databases 123-126 may store various reference spectral data sets including, for example, a reference Raman data set, a reference fluorescence data set, a reference NIR data set, etc. The reference data sets may be collected from different samples and may be used to detect or identify the sample 201 from comparison of its spectral data set with the reference data sets. In one embodiment, during operation, the Raman data sets and fluorescence data sets of the sample 201 also may be stored in one or more of the databases (e.g., database 123) of the processing module 120.

Figure 30:
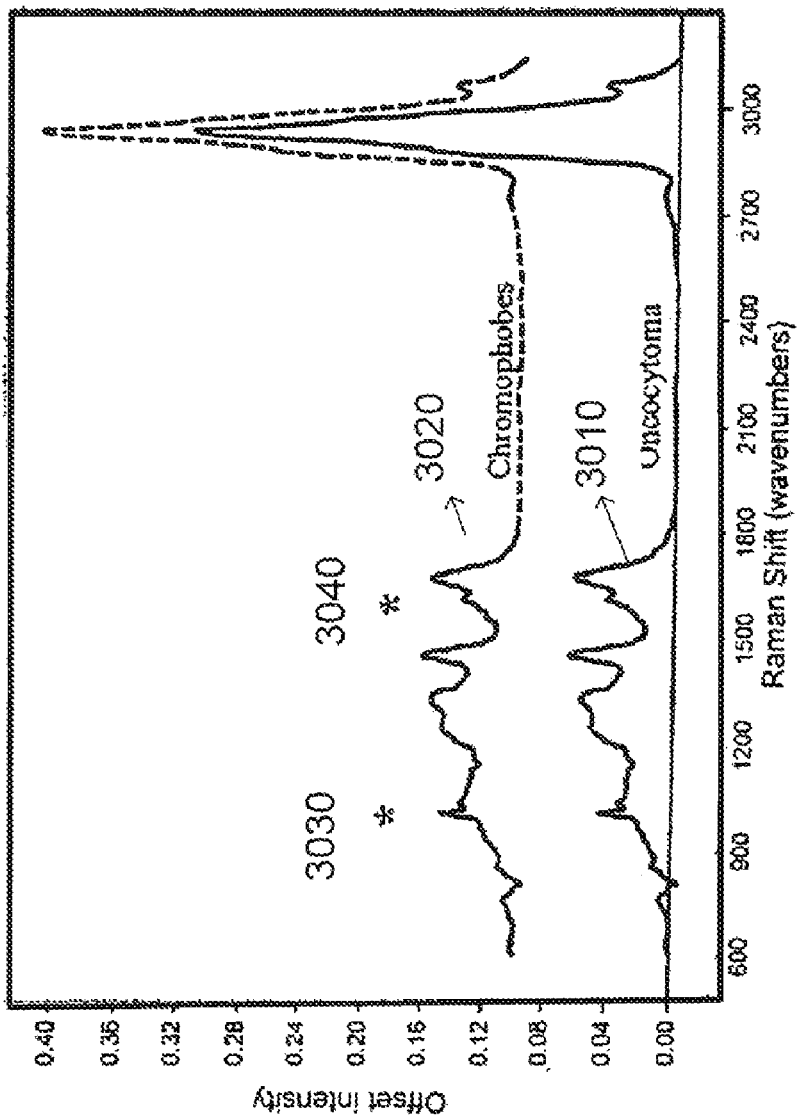
FIG. 30 illustrates reference Raman spectra for samples identified as having a renal oncocytoma disease state and a chromophobe renal carcinoma disease state.

For example, in one embodiment, database 123 may be used to store a plurality of reference Raman data sets from reference cells having a known metabolic state or a known disease state. In one such embodiment, the reference Raman data sets may correspond to a plurality of reference Raman spectra. FIG. 30 illustrates two exemplary reference Raman spectra for known samples being diagnosed as having a renal oncocytoma disease state and a chromophobe renal carcinoma disease state, based on histopathological examination. Spectrum 3010 corresponds to the Raman spectrum for a sample diagnosed as having renal oncocytoma disease. Spectrum 3020 corresponds to the Raman spectrum for a sample diagnosed as having chromophobe renal carcinoma. In another such embodiment, the reference Raman data sets may correspond to a plurality of reference spatially accurate wavelength resolved Raman images.

In another embodiment, the database 124 may be used to store a first plurality of reference Raman data sets from reference normal (non-diseased) cells. In one such embodiment, the reference normal cells correspond to renal oncocytoma cells. In one embodiment, the first reference set of Raman data sets may include a plurality of first reference Raman spectra. In another embodiment, a first reference Raman spectrum may correspond to a dispersive Raman spectrum. In a further embodiment, the first reference set of Raman data sets may include a plurality of first reference spatially accurate wavelength resolved Raman images obtained from corresponding reference normal cells.

In yet another embodiment, the database 125 may store a second plurality of reference Raman data sets from different types of reference diseased cells. In one such embodiment, the reference diseased cells correspond to chromophobe renal carcinoma cells. In one embodiment, the second reference set of Raman data sets includes a plurality of second reference Raman spectra. In one embodiment, the second reference Raman spectrum may correspond to a dispersive Raman spectrum. In another embodiment, the second reference set of Raman data sets may include a plurality of second reference spatially accurate wavelength resolved Raman images obtained from corresponding reference diseased cells.

Similarly, database 126 may store a plurality of reference fluorescence spectra and/or a plurality of reference spatially accurate wavelength resolved fluorescence spectroscopic images obtained from reference biological samples (e.g., cancerous human tissues). One or more of the reference biological samples may include fluorescence probe molecules (e.g., fluorescein isothiocyanate). In one embodiment, a single database may be used to store all types of spectra.

The reference Raman data sets may be associated with a reference Raman image and/or a corresponding reference non-Raman image. In one such embodiment, the reference non-Raman image may include at least one of: a brightfield image; a polarized light image; and a UV-induced autofluorescence image.

Figure 3:
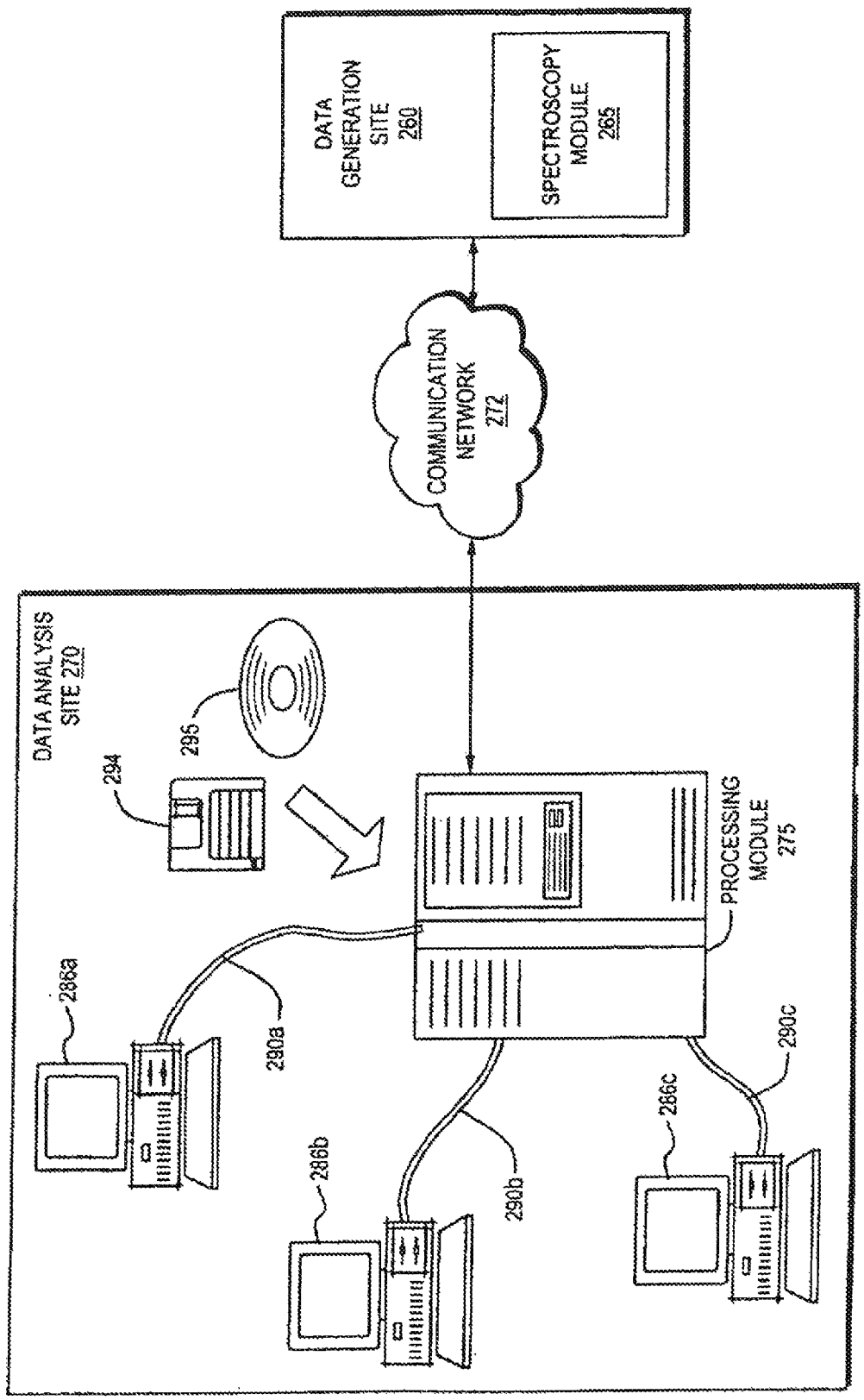
FIG. 3 schematically represents an exemplary system of the present disclosure.

FIG. 3 depicts an exemplary setup to remotely perform spectroscopic analysis of test samples according to one embodiment of the present disclosure. Spectroscopic data from a test sample or a test sample may be collected at a data generation site 260 using a spectroscopy module 265. In one embodiment, the spectroscopy module may be functionally similar to the spectroscopy module 110 discussed hereinbefore with reference to FIGS. 2A-2B. The spectroscopic data collected at the data generation site 260 may be transferred to a data analysis site 270 via a communication network 272. In one embodiment, the communication network 272 may be any data communication network such as an Ethernet LAN (local area network) connecting all the data processing and computing units within a facility, e.g., a university research laboratory, or a corporate research center. In that case, the data generation site 260 and the data analysis site 270 may be physically located within the same facility, e.g., a university research laboratory or a corporate research center. In alternative embodiments, the communication network 272 may include, independently or in combination, any of the present or future wireline or wireless data communication networks such as, for example, the Internet, the PSTN (public switched telephone network), a cellular telephone network, a WAN (wide area network), a satellite-based communication link, a MAN (metropolitan area network), etc. In this case, the data generation site 260 and the data analysis site 270 may be physically located in different facilities. In some embodiments, the data generation site 260 and the data analysis site 270 that are linked by the communication network 272 may be owned or operated by different entities.

The data analysis site 270 may include a processing module 275 to process the spectroscopic data received from the data generation site 260. In one embodiment, the processing module 275 may be similar to the processing module 120 and may also include a number of different databases (not shown) storing different reference spectroscopic data sets (e.g., a first plurality of reference Raman data sets for non-progressive cancer tissues, a second plurality of reference Raman data sets for progressive cancer tissues, a third plurality of reference Raman data sets for normal or non-diseased tissues; a fourth plurality of reference data set for renal oncocytomas samples and chromophobe renal cell carcinoma samples, etc.). The processing module 275 may include a processor (similar to the processor 122 of the processing module 120 in FIG. 1) that is configured to execute program code or software to perform various spectral data processing tasks according to the teachings of the present disclosure. The machine-readable program code containing executable program instructions may be initially stored on a portable data storage medium, e.g., a floppy diskette 294, a compact disc or a DVD 295, a data cartridge tape (not shown), or any other suitable digital data storage medium. The processing module 275 may include appropriate disk drives to receive the portable data storage medium and may be configured to read the program code stored thereon, thereby facilitating execution of the program code by its processor. The program code, upon execution by the processor of the processing module 275, may cause the processor to perform a variety of data processing and display tasks including, for example, initiate transfer of spectral data set from the data generation site 260 to the data analysis site 270 via the communication network 272, compare the received spectral data set to various reference data sets stored in the databases of the processing module 275, classify or identify the test sample based on the comparison (e.g., whether the test sample has a progressive cancer or non-progressive cancer state or whether the test sample has renal oncocytomas disease or chromophobe renal cell carcinoma disease), transfer the classification or identification results to the data generation site 260 via the communication network 272, etc.

In one embodiment, the data analysis site 270 may include one or more computer terminals 286A-286C communicatively connected to the processing module 275 via corresponding data communication links 290A-290C, which can be serial, parallel, or wireless communication links, or a suitable combination thereof. Thus, users may utilize functionalities of the processing module 275 via their computer terminals 286A-286C, which may also be used to display spectroscopic data received from the data generation site 260 and the results of the spectroscopic data processing by the processing module 275, among other applications. It is evident that in a practical application, there may be many more computer terminals 286 than just three terminals shown in FIG. 3.

The computer terminals 286A-286C may be, e.g., a personal computer (PC), a graphics workstation, a multiprocessor computer system, a distributed network of computers, or a computer chip embedded as part of a machine or mechanism. Similarly, the data generation site 260 may include one or more of such computers (not shown) for viewing the results of the spectroscopic analysis received from the data analysis site 270. Each computer terminal, whether at the data generation site 260 or at the data analysis site 270, may include requisite data storage capability in the form of one or more volatile and non-volatile memory modules. The memory modules may include RAM (random access memory), ROM (read only memory) and HDD (hard disk drive) storage.

It is noted that the arrangement depicted in FIG. 3 may be used to provide a commercial, network-based spectroscopic data processing service that may perform customer-requested processing of spectroscopic data in real time or near real time. For example, the processing module 275 at the data analysis site 270 may be configured to identify a test sample from the spectroscopic data remotely submitted to it over the communication network 272 (e.g., the Internet) from the spectroscopy module 265 automatically or through an operator at the data generation site 260. The client site (data generation site) 260 may be, for example, a government laboratory or a medical facility or pathological laboratory. The results of spectroscopic data analysis may be transmitted back to the client site 260 for review and further analysis. In one embodiment, the whole data submission, analysis, and reporting process can be automated.

It is further noted that the owner or operator of the data analysis site 270 may commercially offer a network-based spectroscopic data content analysis service, as illustrated by the arrangement in FIG. 3, to various individuals, corporations, governmental entities, laboratories, or other facilities on a fixed-fee basis, on a per-operation basis or on any other payment plan mutually convenient to the service provider and the service recipient.

Processing module 120 may also include a test Raman database associated with a test biological sample having an unknown metabolic state. In one such embodiment, the test Raman data set may correspond to a plurality of Raman spectra of the test biological sample. In another such embodiment, the test Raman data set may correspond to a plurality of spatially accurate wavelength resolved Raman images of the test biological sample. In another embodiment, each of the test Raman data sets may be associated with least one of the following: a corresponding test Raman image; and a corresponding test non-Raman image. In one such embodiment, the test non-Raman image may include at least one of the following: a brightfield image; a polarized light image; and a UV-induced autofluorescence image.

In one such embodiment, processing module 120 may also include a test Raman database associated with a test renal sample having an unknown renal disease state. In one such embodiment, the test Raman data set may correspond to a plurality of Raman spectra of the test renal sample. In another such embodiment, the test Raman data set may correspond to a plurality of spatially accurate wavelength resolved Raman images of the test renal sample. In another embodiment, each of the test Raman data sets may be associated with least one of the following: a corresponding test Raman image; and a corresponding test non-Raman image. In one such embodiment, the test non-Raman image may include at least one of the following: a brightfield image; a polarized light image; and a UV-induced autofluorescence image.

In one embodiment, the test Raman spectra are generated using a test Raman image to identify one or more regions of interest of the test biological sample or the test renal sample. In one such embodiment, the one or more regions of interest contain at least one of the following: an epithelium area, a stroma area, epithelial-stromal junction (ESJ) area, and/or nuclei area. A plurality of test Raman spectra may be obtained from the one or more of regions of interest of the test biological sample or the rest renal sample.

A diagnosis of a test sample as diseased or non-diseased or a prediction of the metabolic state of a test sample may be made by comparing a test Raman data set to reference Raman data sets using a chemometric technique. In one such embodiment, a diagnosis of a test renal sample as having a renal oncocytoma disease state or a chromophobe renal carcinoma disease state is generated. The chemometric technique may include at least one of the following: Principal Component Analysis, Minimum noise fraction, spectral mixture resolution and linear discriminant analysis.

In one embodiment, the chemometric technique may be spectral unmixing. The application of spectral unmixing to determine the identity of components of a mixture is described in U.S. Pat. No. 7,072,770, entitled "Method for Identifying Components of a Mixture via Spectral Analysis, issued on Jul. 4, 2006, which is incorporated herein by reference in it entirety. Spectral unmixing as described in the above referenced patent can be applied as follows: Spectral unmixing requires a library of spectra which include possible components of the test sample. The library can in principle be in the form of a single spectrum for each component, a set of spectra for each component, a single Raman image for each component, a set of Raman images for each component, or any of the above as recorded after a dimension reduction procedure such as Principle Component Analysis. In the methods discussed herein, the library used as the basis for application of spectral unmixing is the reference Raman data sets.

With this as the library, a set of Raman measurements made on a sample of unknown state, described herein as a test Raman data set, is assessed using the methods of U.S. Pat. No. 7,072,770 to determine the most likely groups of components which are present in the sample. In this instance the components are actually disease states of interest and/or clinical outcome. The result is a set of disease state groups and/or clinical outcome groups with a ranking of which are most likely to be represented by the test data set.

Given a set of reference spectra, such as those described above, a piece or set of test data can be evaluated by a process called spectral mixture resolution. In this process, the test spectrum is approximated with a linear combination of reference spectra with a goal of minimizing the deviation of the approximation from the test spectrum. This process results in a set of relative weights for the reference spectra.

In one embodiment, the chemometric technique may be Principal Component Analysis. Using Principal Component Analysis results in a set of mathematical vectors defined based on established methods used in multivariate analysis. The vectors form an orthogonal basis, meaning that they are linearly independent vectors. The vectors are determined based on a set of input data by first choosing a vector which describes the most variance within the input data. This first "principal component" or PC is subtracted from each of the members of the input set. The input set after this subtraction is then evaluated in the same fashion (a vector describing the most variance in this set is determined and subtracted) to yield a second vector—the second principal component. The process is iterated until either a chosen number of linearly independent vectors (PCs) are determined, or a chosen amount of the variance within the input data is accounted for.

In one embodiment, the Principal Component Analysis may include a series of steps. A pre-determined vector space is selected that mathematically describes a plurality of reference Raman data sets. Each reference Raman data set may be associated with a known biological sample having an associated metabolic state. The test Raman data set, may be transformed into the pre-determined vector space, and then a distribution of transformed data may be analyzed in the pre-determined vector space to generate a diagnosis.

In another embodiment, the Principal Component Analysis may include a series of steps. A pre-determined vector space is selected that mathematically describes a first plurality of reference Raman data sets associated with a known biological sample having an associated diseased state and a second plurality of reference Raman data sets associated with a known biological sample having an associated non-diseased state. The test Raman data set may be transformed into the pre-determined vector space, and then a distribution of transformed data may be analyzed in the pre-determined vector space to generate a diagnosis.

In yet another embodiment, the Principal Component Analysis may include a series of steps. A pre-determined vector space is selected that mathematically describes a first plurality of reference Raman data sets associated with a known biological sample having an associated progressive state and a second plurality of reference Raman data sets associated with a known biological sample having an associated non-progressive state. The test Raman data set may be transformed into the pre-determined vector space, and then a distribution of transformed data may be analyzed in the pre-determined vector space to generate a diagnosis.

Figure 31:
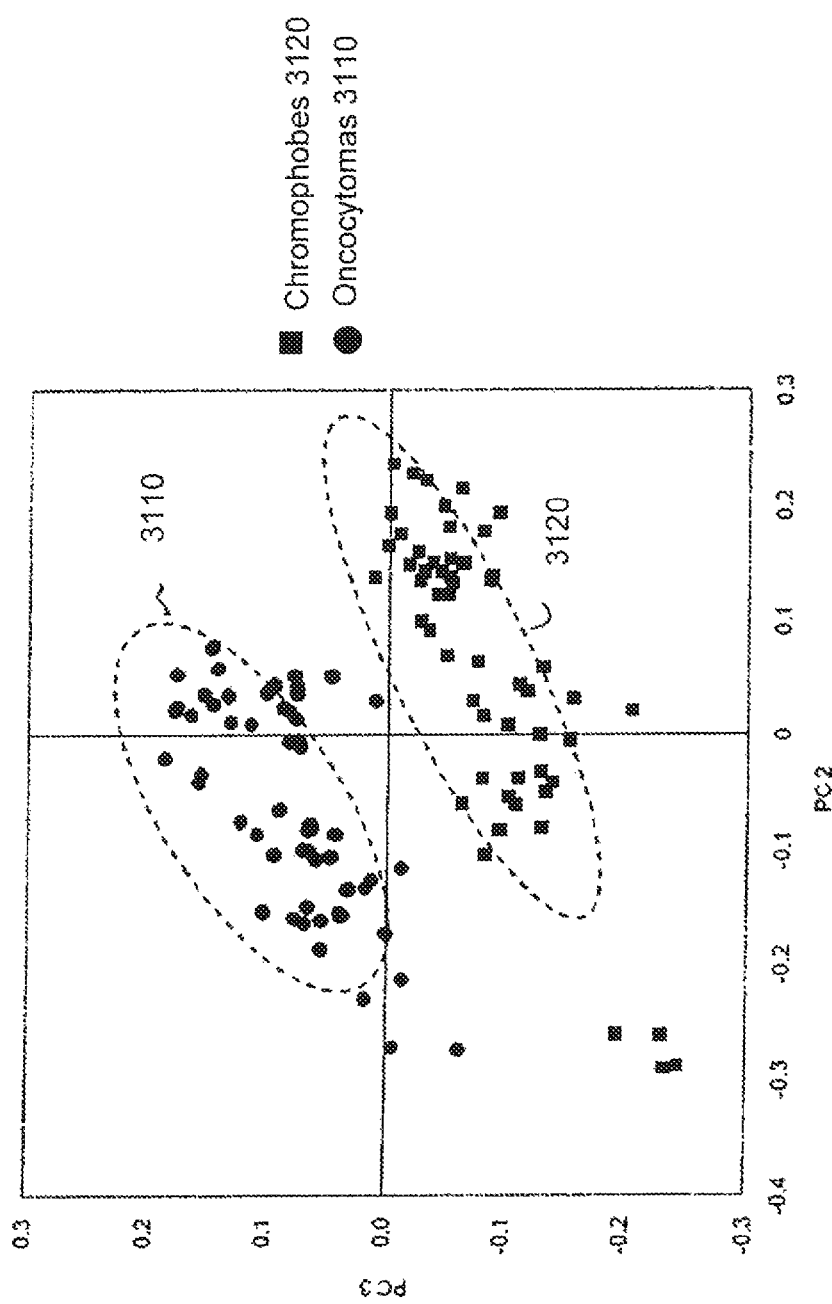
FIG. 31 illustrates an exemplary classification model for renal tissue samples.

In still yet another embodiment, the Principal Component Analysis may include a series of steps. A pre-determined vector space is selected that mathematically describes a first plurality of reference Raman data sets associated with a known renal sample having an associated renal oncocytoma disease state and a second plurality of reference Raman data sets associated with a known renal sample having an associated chromophobe renal carcinoma disease state. The test Raman data set may be transformed into the pre-determined vector space, and then a distribution of transformed data may he analyzed in the pre-determined vector space. FIG. 31 illustrates scatter plots generated by applying Principal Component Analysis on such reference Raman data sets associated with known renal samples. The scatter plots show a clear separation between the reference data associated with the known renal oncocytoma samples and referenced data associated with the known renal carcinoma disease samples in principal component space. Data points 3110 correspond to data for the known renal oncocytoma samples and data points 3120 correspond to known chromophobe renal carcinoma disease samples.

The analysis of the distribution of the transformed data may be performed using a classification scheme. Some examples of the classification scheme may include: Mahalanobis distance, Adaptive subspace detector, Band target entropy method, Neural network, and support vector machine as an incomplete list of classification schemes known to those skilled in the art.

In one such embodiment, the classification scheme is Mahalanobis distance. The Mahalanobis distance is an established measure of the distance between two sets of points in a multidimensional space that takes into account both the distance between the centers of two groups, but also the spread around each centroid. A Mahalanobis distance model of the data is represented by plots of the distribution of the spectra in the principal component space. The Mahalanobis distance calculation is a general approach to calculating the distance between a single point and a group of points. It is useful because rather than taking the simple distance between the single point and the mean of the group of points, Mahalanobis distance takes into account the distribution of the points in space as part of the distance calculation. The Mahalanobis distance is calculated using the distances between the points in all dimensions of the principal component space.

In one such embodiment, once the test Raman data is transformed into the space defined by the predetermined PC vector space, the test data is analyzed relative to the pre-determined vector space. This may be performed by calculating a Mahalanobis distance between the test Raman data set transformed into the pre-determined vector space and the Raman data sets in the pre-determined vector space to generate a diagnosis.

Figure 5:
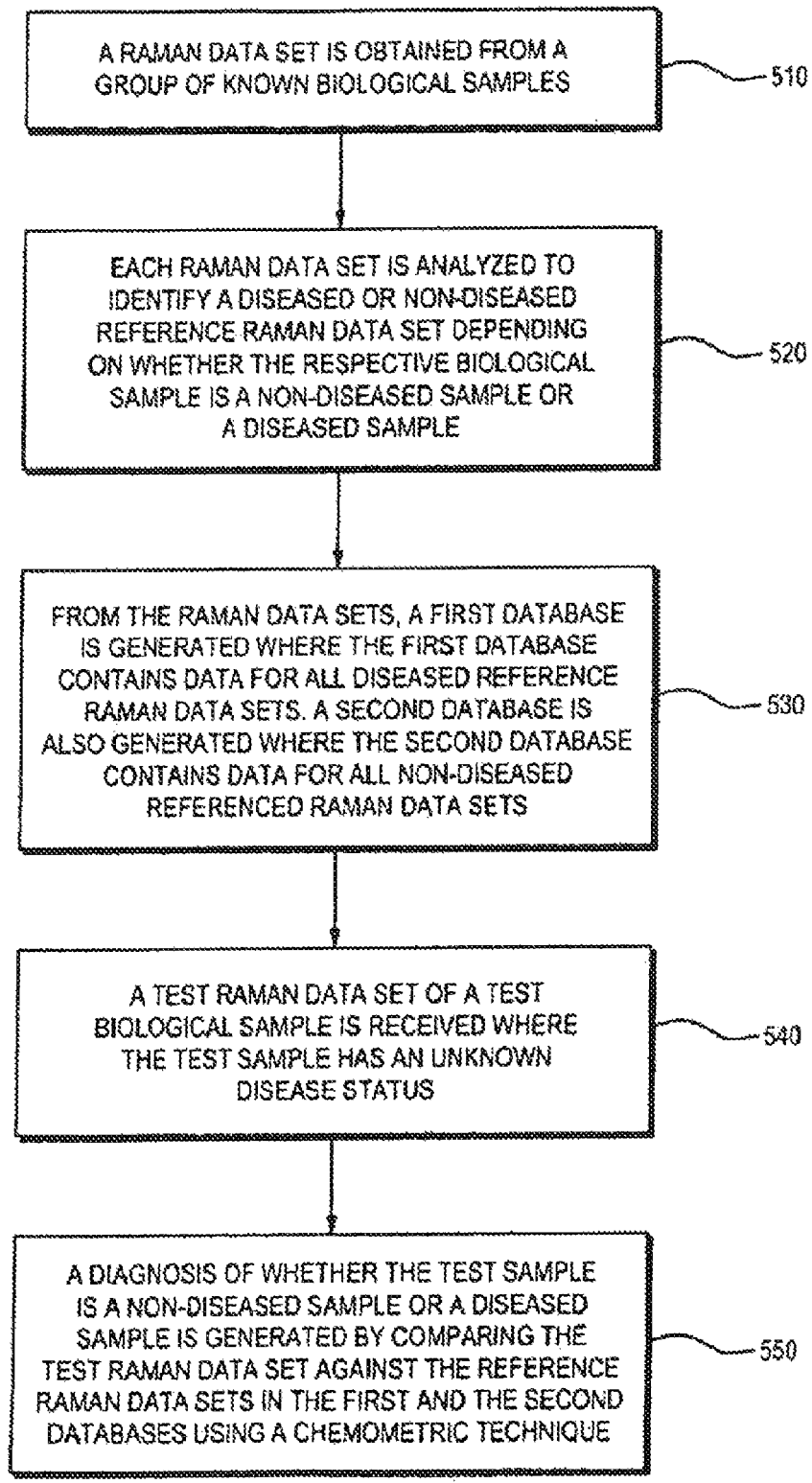
FIG. 5 is a flow chart illustrating an exemplary method of the present disclosure.

The exemplary systems of FIGS. 1 and 2 may be used to perform methods to predict the clinical outcome of patients or diagnose a disease state of patients. Processor 122 is configured to execute program instructions to carry out these methods. One such embodiment is illustrated in FIG. 5 which shows a flow chart for a method of the present disclosure. In step 510, a Raman data set is obtained from a group of known biological samples. Each Raman data set is analyzed to identify a diseased or non-diseased reference Raman data set depending on whether the respective biological sample is a non-diseased sample or a diseased sample, step 520. From the Raman data sets, a first database is generated where the first database contains data for all diseased reference Raman data sets. A second database is also generated where the second database contains data for all non-diseased reference Raman data sets, step 530. In step 540, a test Raman data set of a test biological sample is received where the test sample has an unknown disease status. In step 550, a diagnosis of whether the test sample is a non-diseased sample or a diseased sample is generated by comparing the test Raman data set against the reference Raman data sets in the first and the second databases using a chemometric technique.

Figure 6:
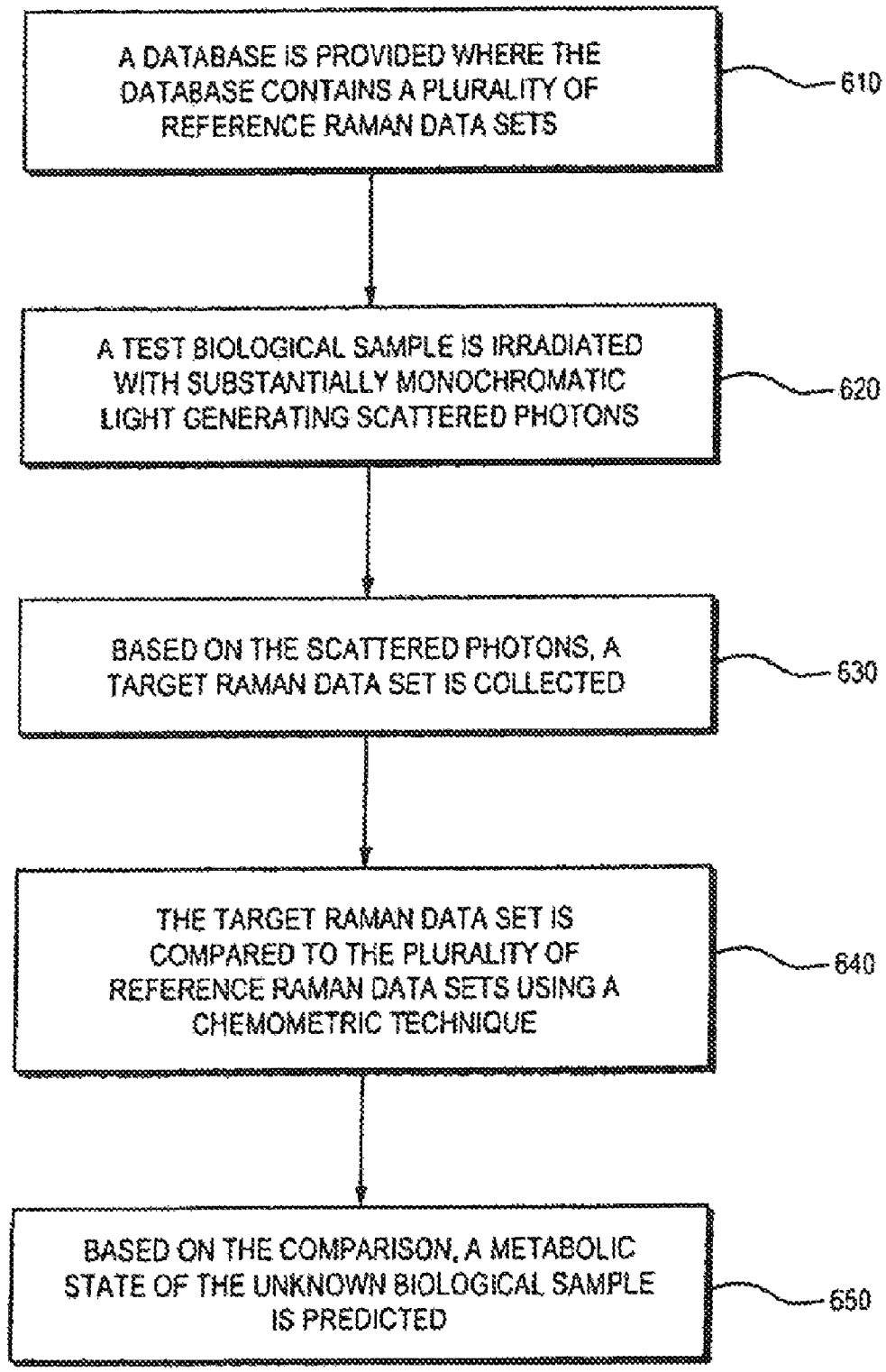
FIG. 6 is a flow chart illustrating an exemplary method of the present disclosure.

In another such embodiment, FIG. 6 illustrates a flow chart for another method of the present disclosure. In step 610, a database is provided where the database contains a plurality of reference Raman data sets. In step 620, a test biological sample is irradiated with substantially monochromatic light generating scattered photons. Based on the scattered photons, a test Raman data set is collected, in step 630. The test Raman data set is compared to the plurality of reference Raman data sets using a chemometric technique, in step 640. Based on the comparison, a metabolic state of the test biological sample is predicted, in step 650.

Figure 7:
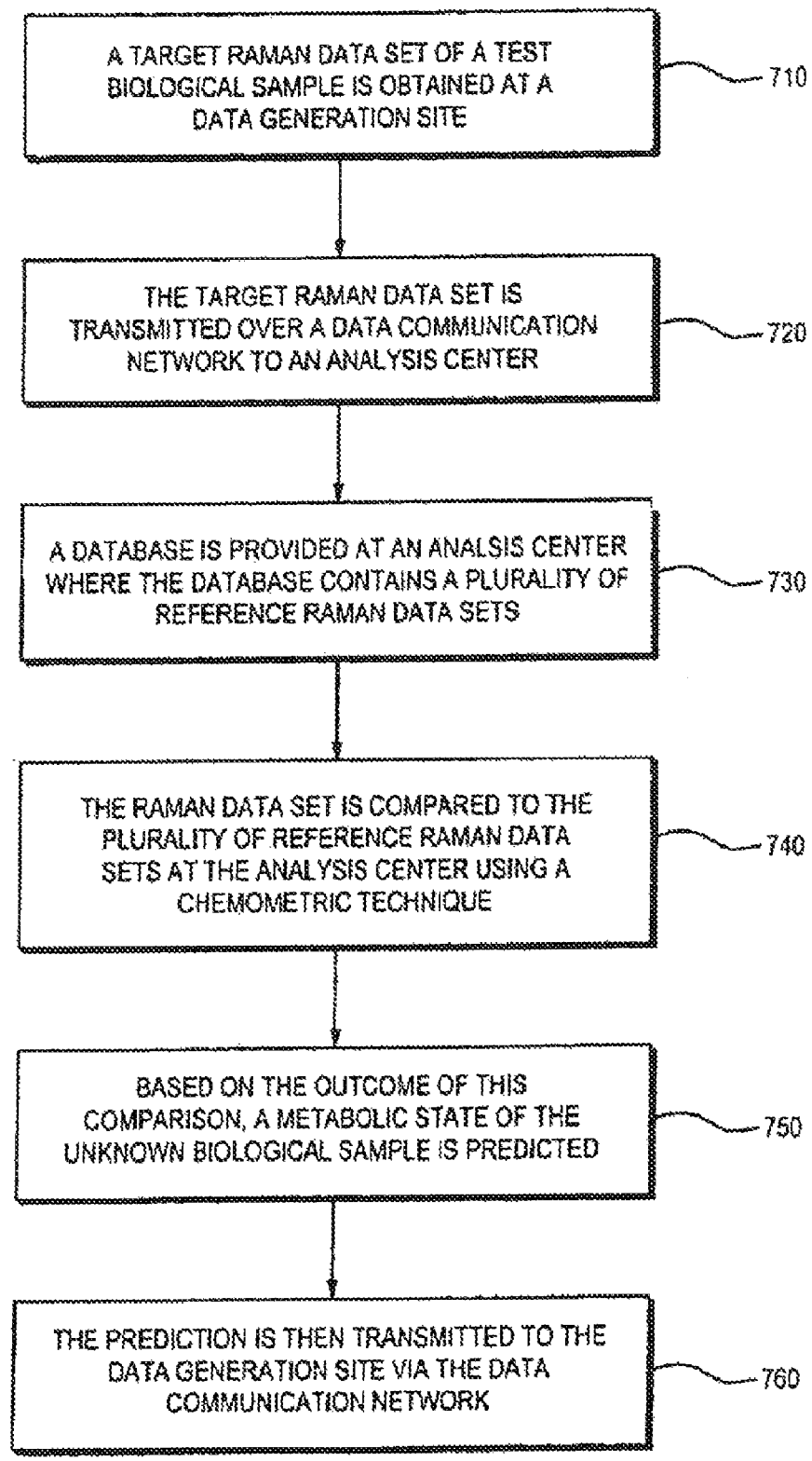
FIG. 7 is a flow chart illustrating an exemplary method of the present disclosure.

In another embodiment of the present disclosure, the exemplary system of FIG. 3 may be used to carry out methods to predict the clinical outcome of patients. In this method, data obtained at a data generation site is transmitted to an analysis site to obtain a prediction of the metabolic state of a test biological sample. The prediction is then transmitted back to the data generation site. The transmission may be performed over a data communication network such as the Internet. FIG. 7 illustrates an exemplary flow chart for such a method. In step 710, a test Raman data set of a test biological sample is obtained at a data generation site. The test Raman data set is transmitted over a data communication network to an analysis center, in step 720. A database is provided at an analysis center where the database contains a plurality of reference Raman data sets, step 730. Each reference Raman data set has an associated known biological sample and an associated known metabolic state. The Raman data set is compared to the plurality of reference Raman data sets at the analysis center using a chemometric technique, in step 740. Based on the outcome of this comparison, a metabolic state of the test biological sample is predicted, in step 750. The prediction is then transmitted to the data generation site via the data communication network, in step 760.

Figure 32:
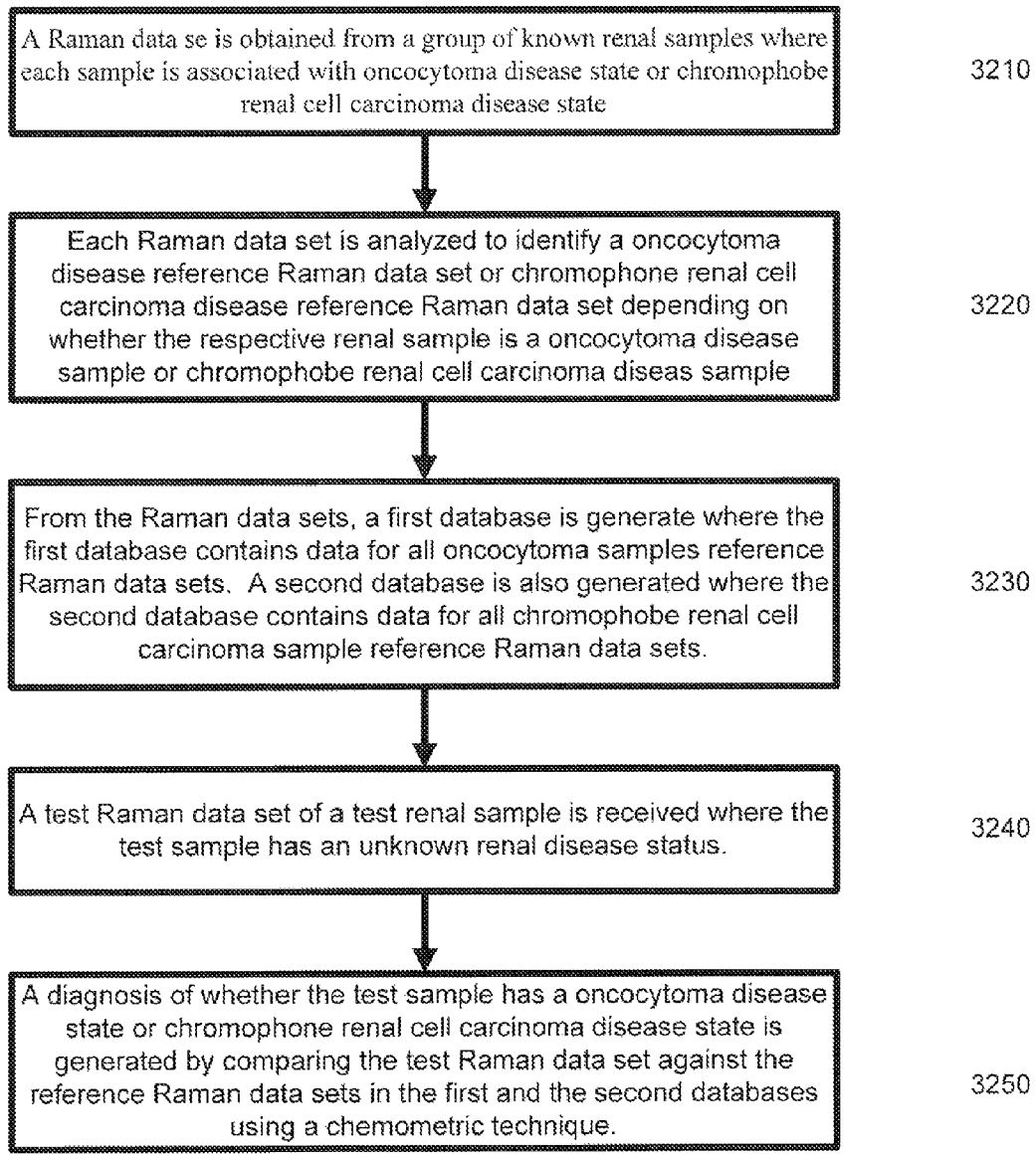
FIG. 32 is a flow chart illustrating an exemplary method of the present disclosure.

Yet another embodiment is illustrated in FIG. 32 which shows a flow chart for a method of the present disclosure. In step 3210, a Raman data set is obtained from a group of known renal samples. Each Raman data set is analyzed to identify an oncocytoma disease reference Raman data set or chromophobe renal carcinoma disease reference Raman data depending on whether the respective renal sample is an oncocytoma disease sample or chromophobe renal carcinoma disease sample, step 3220. From the Raman data sets, a first database is generated where the first database contains data for all oncocytoma disease reference Raman data sets. A second database is also generated where the second database contains data for all chromophobe renal carcinoma reference Raman data sets, step 3230. In step 3240, a test Raman data set of a test renal sample is received where the test sample has an unknown renal disease status. In step 3250, a diagnosis of whether the test sample has a oncocytoma disease state or a chromophobe renal carcinoma disease state is generated by comparing the test Raman data set against the reference Raman data sets in the first and the second databases using a chemometric technique.

Figure 33:
FIG. 33 is a flow chart illustrating an exemplary method of the present disclosure.

Still yet another such embodiment is illustrated in FIG. 33. In step 3310, a database is provided where the database contains a plurality of reference Raman data sets. In step 3320, a test renal sample is irradiated with substantially monochromatic light generating scattered photons. Based on the scattered photons, a test Raman data set is collected, in step 3330. The test Raman data set is compared to the plurality of reference Raman data sets using a chemometric technique, in step 3340. Based on the comparison, a diagnosis of a renal disease state is generated in step 3350. The diagnosis may include oncocytoma disease state or chromophobe renal carcinoma disease state.

Figure 34:
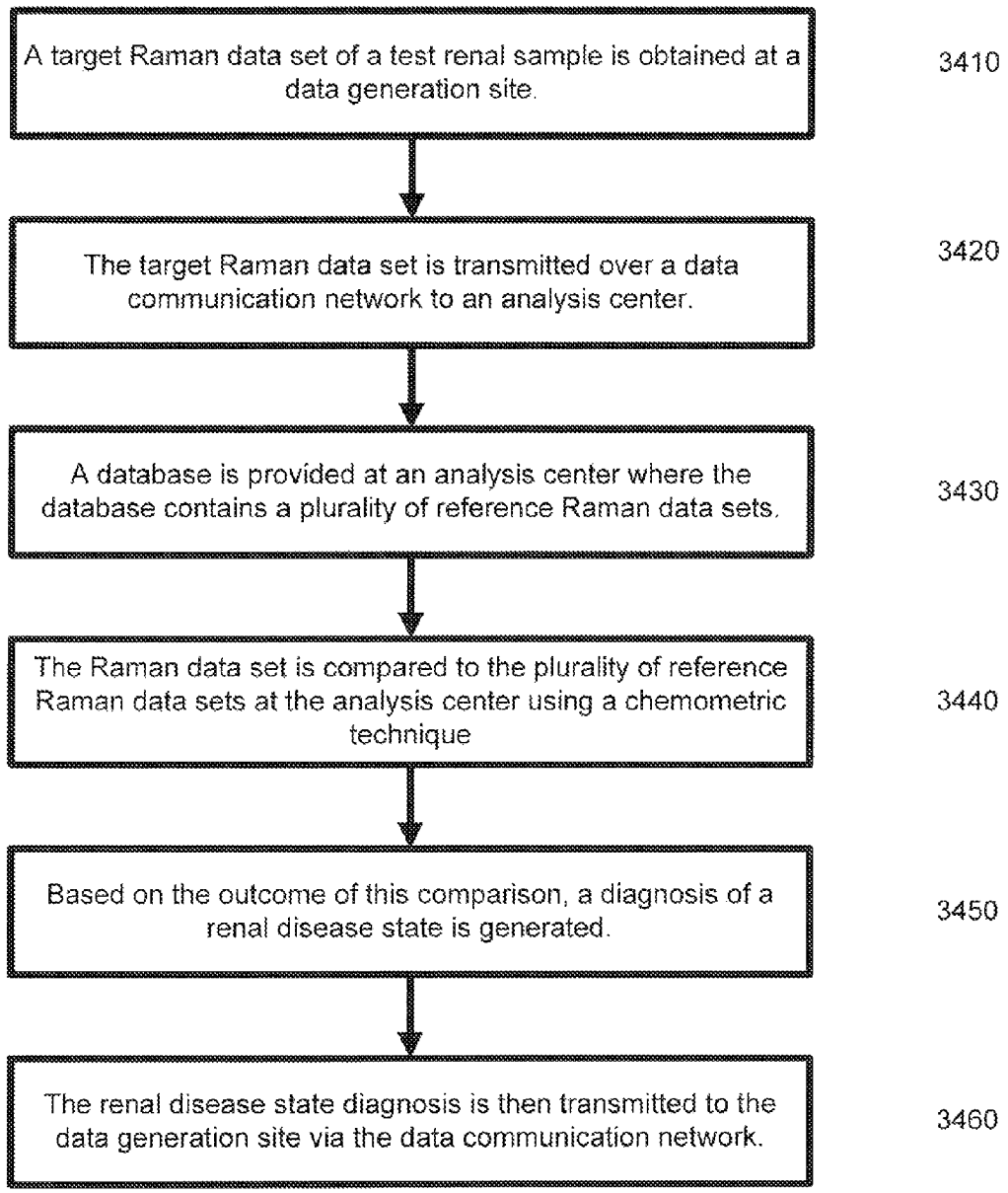
FIG. 34 is a flow chart illustrating an exemplary method of the present disclosure.

In another embodiment of the present disclosure, the exemplary system of FIG. 3 may be used to carry out methods to diagnose the renal disease states of patients. In this method, data obtained at a data generation site is transmitted to an analysis site to obtain a diagnosis of the renal disease state of a test renal sample. The diagnosis is then transmitted back to the data generation site. The transmission may be performed over a data communication network such as the Internet. FIG. 34 illustrates an exemplary flow chart for such a method. In step 3410, a test Raman data set of a test renal sample is obtained at a data generation site. The test Raman data set is transmitted over a data communication network to an analysis center, in step 3420. A database is provided at an analysis center where the database contains a plurality of reference Raman data sets, step 3430. Each reference Raman data set has an associated known renal sample and an associated known renal disease state. The Raman data set is compared to the plurality of reference Raman data sets at the analysis center using a chemometric technique, in step 3440. Based on the outcome of this comparison, a diagnosis of the renal disease state of the test biological sample is provided, in step 750. The diagnosis is then transmitted to the data generation site via the data communication network, in step 3460. The diagnosis may include oncocytoma disease state or chromophobe renal carcinoma disease state.

EXAMPLES

The following examples demonstrate the method and system of the present disclosure.

The samples discussed in the below examples were tissue samples prepared using standard histology techniques from paraffin embedded tissue sections which reside in a clinical sample database. Five (5) micron thick sections were prepared and placed on an aluminum side of an aluminum coated glass slide. Paraffin was removed using standard procedures and solvents. An adjacent section was prepared in standard fashion and stained with hematoxalin and Eosin for routine pathology analysis. Expert pathologists reviewed each sample and confirmed the diagnosis.

Raman spectra, under widefield illumination conditions, were obtained for each of the twenty tissue areas using the Falcon II™ Raman imaging system from ChemImage Corporation of Pittsburgh, Pa. Typical Raman dispersive spectral were collected from cells using 595 W/cm$^2$ laser power density, 100× objective, and appropriate exposure times to get good signal to noise (typically 10-60 s). Baseline, dark current and bias corrections were applied to the acquired spectra. Spectral processing and data analysis was performed using ChemImage Xpert™ 2.0 software available from ChemImage Corporation of Pittsburgh, Pa. Typical spatially accurate wavelength resolved Raman chemical images were acquired using 514 W/cm$^2$ laser power density, 50× objective, 8×8 binning, and 1.5 s exposure time, and 5 averages over the spectral range of 600-3200 cm$^{-1}$. These parameters are typical for the data discussed below.

Example 1

The example demonstrates the creation of a reference Raman database having progressive Raman data sets and non-progressive Raman data sets for Gleason 6 cancer tissue. A series of case-control pairs of patients were selected for analysis. A case sample was defined as a patient who developed prostate cancer characterized as having a Gleason 6 pattern and developed metastatic prostate cancer after removal of the prostate. For the purposes of this application, a case sample from a patient who developed metastatic cancer is defined having progressive cancer. A control sample was selected to match each case sample in terms of relative clinical variable but the patient did not develop metastatic prostate cancer after removal of the prostate. For the purposes of this application, a control sample, having cancer but no development of metastasis, is defined having non-progressive cancer.

An unstained thin section of a tissue sample, for each case and control sample, was placed on the stage of a FALCON II™ Raman imaging microscope. Twenty (20) tissue areas were evaluated on each unstained tissue sample section. For each area, non-Raman images were acquired using multiple modalities including bright field reflectance, cross polarized light reflectance, integrated autofluorescence under UV excitation, differential interference contrast, and monochromatic excitation. After collection of Raman data sets (dispersive spectrum under wide field illumination, Raman image), brightfield, cross polarized light reflectance and autofluorescence images, the sample was stained using standard pathology routines with haematoxylin and Eosin. Subsequent to staining a digital image of the stained sample was acquired. These non-Raman images were obtained for the same field of view using the procedures described in U.S. patent appl. Ser. No. 11/647,195, filed Dec. 29, 2006, and entitled "Method for Correlating Spectroscopic Measurements with Digital Images of Contrast Enhanced Images," which is incorporated by reference herein in its entirety.

Figure 8:
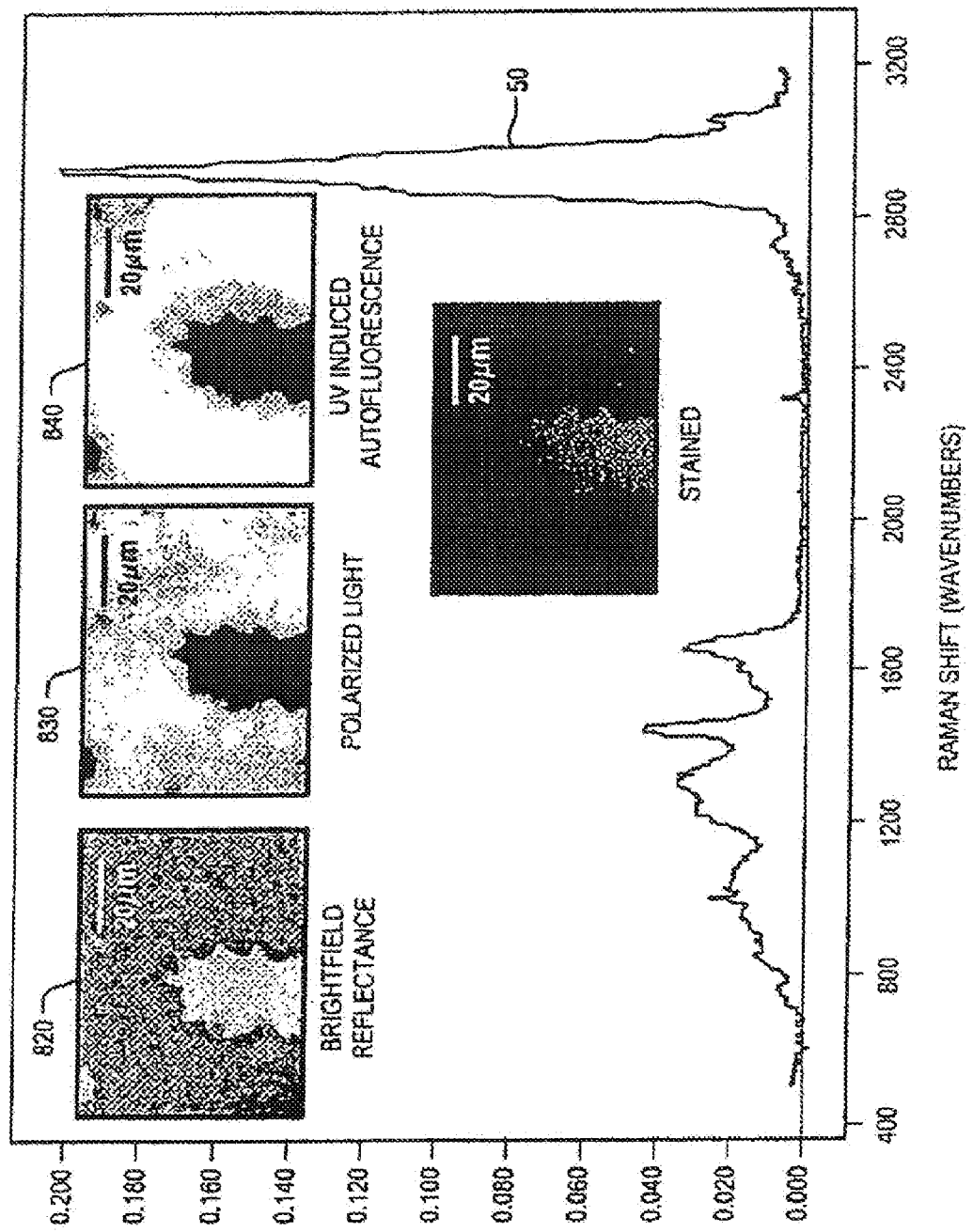
FIG. 8 illustrates a Raman spectrum and non-Raman images of a Gleason 6 prostate cancer sample.

FIG. 8 illustrates an exemplary data set for a tissue sample, including a bright field image 820, a polarized light image 830, an autofluorescence image 840, a stained image 850 and a Raman spectrum 850 for a selected tissue area.

Figure 9:
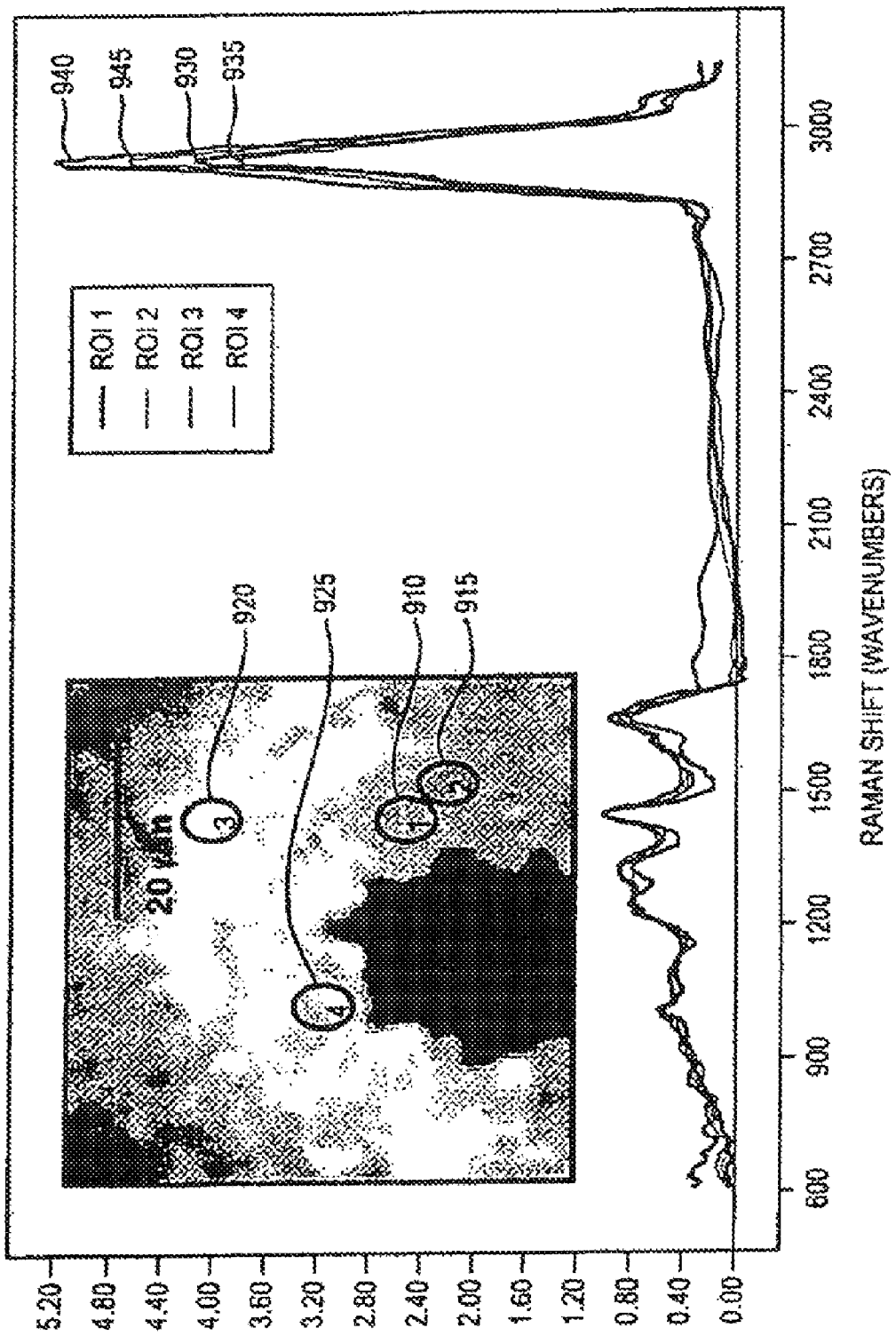
FIG. 9 illustrates regions of interest within a Raman image and the associated Raman spectra.

For this tissue area, four regions of interest, 910, 915, 920 and 925 were selected as illustrated in FIG. 9. A Raman spectrum was then obtained for each region of interest where spectrum 930 is associated with region of interest 910, spectrum 935 is associated with region of interest 935, spectrum 920 is associated with region of interest 940, and spectrum 925 is associated with region of interest 945. Similar data, as shown in FIGS. 8 and 9, were obtained for each of the three case-control pairs. Principal component analysis was applied to the Raman data sets for each case-control pair.

Figure 10:
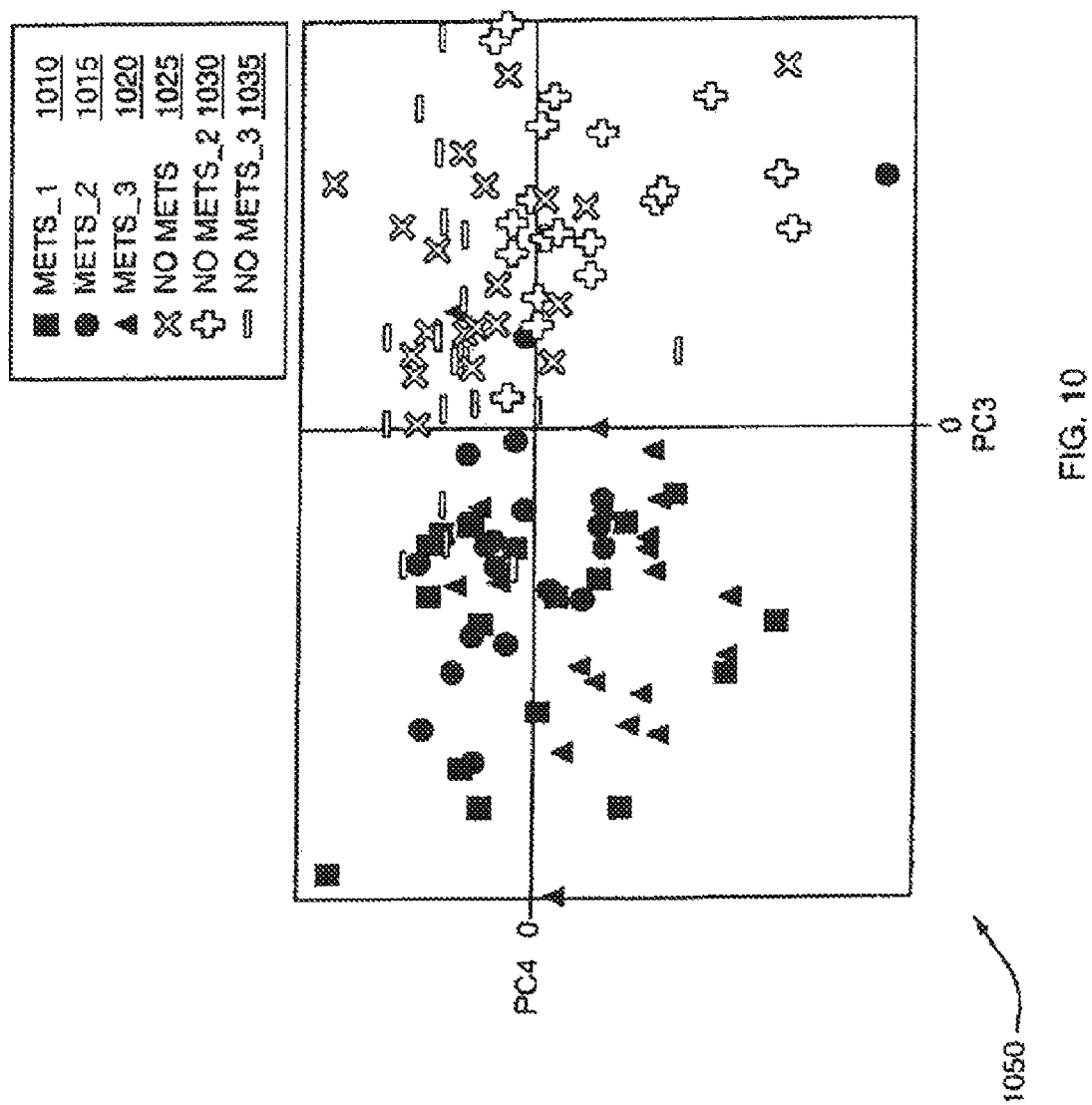
FIG. 10 illustrates an exemplary classification model for Gleason 6 prostate cancer samples.

From the evaluation of the reference Raman spectra obtained for the progressive prostate tissue and the non-progressive cancer tissue, scatter plots were generated showing a separation between the data for the progressive and non-progressive cancer tissue samples in principal component space. FIG. 10 represents an exemplary predetermined vector space, or a projection of the vector space onto the two coordinates (PC3 and PC4). As shown in FIG. 10, the points labeled 1010, 1015 and 1020 mathematically describe the reference Raman spectra data sets collected for progressive tissue. The points labeled 1025, 1030 and 1035 mathematically describe the reference Raman spectra data sets collected for non-progressive tissue. The scatter plots of the distribution of the Raman spectra in principal component space show a clear difference between progressive tissue 1010, 1015 and 1020 and non-progressive tissue 1025, 1030 and 1035. The data points associated with the Raman spectra for non-progressive tissue are clustered in the same area of the principal component space and are separate from the data points associated with the Raman spectra for progressive tissue.

Once the vector space is established, classification of a test Raman dataset is performed by transforming the test Raman dataset into the vector space and analyzing which group the transformed data lies nearest to. The determination of the metabolic state (in this example whether the cancer is going to be progressive) is made by selecting the group which the test data set lies closest to after the transformation.

To demonstrate the feasibility of the methods of the present disclosure, each Raman spectrum, for the Gleason 6 tissue samples, was then classified as progressive tissue or non-progressive tissue by using a Leave-One-Out (LOO) cross validation approach wherein a classification model (vector space) was generated with all of the Raman data sets except a single spectrum (test Raman data set). The classification model thus generated was used to classify the one spectrum (test Raman data set) which was left out. The process was repeated for all spectra.

The results of the LOO are shown below in Table 1. These results are consistent with a sensitivity of 93% and a specificity of 93%.

TABLE 1

| Sample | Gleason 7 Progressive | Gleason 7 Non-Progressive |
|---|---|---|
| # of samples | 58 | 60 |
| Classified as progressive | 54 | 4 |
| Classified as non-progressive | 4 | 56 |

Figure 11:
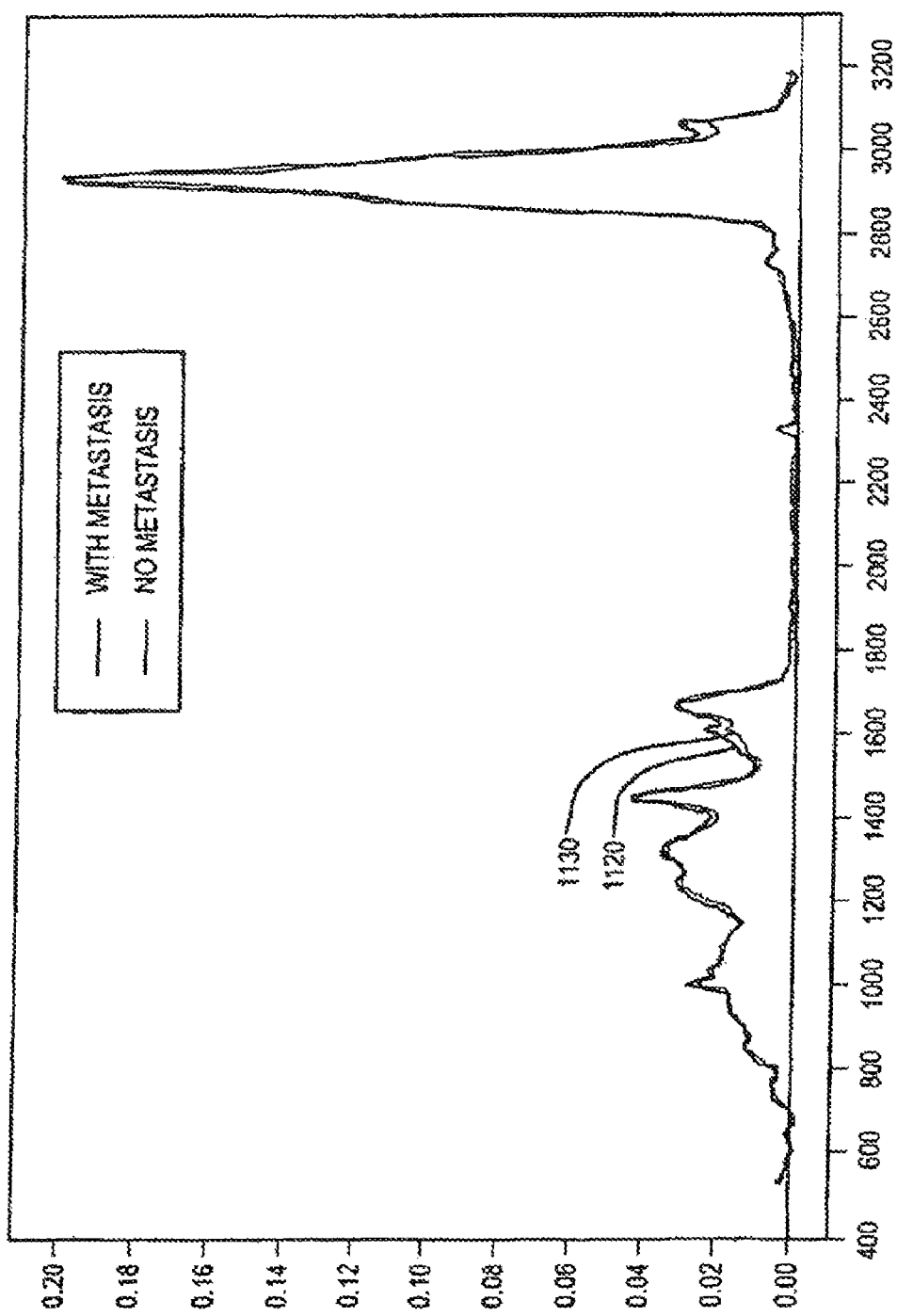
FIG. 11 illustrates mean Raman spectra for progressive Gleason 6 prostate cancer samples and non-progressive Gleason 6 prostate cancer samples.

Mean Raman spectra were generated for each tissue type from the 40 Raman spectra collected as described above. FIG. 11 shows mean Raman spectrum 1120 from known tissue samples of patients who progressed to metastatic prostate disease 1120, and the mean Raman spectrum 1120 from tissue samples of patients who did not progress to metastatic prostate disease. Subtle differences, in these mean spectra, are indicators of the presence or absence of components which are responsible for the progressive or non-progressive nature of the Gleason 6 prostate cancer.

From this example, several conclusions can be drawn. First, Raman spectroscopy is capable of detecting the components of prostate tissue which are responsible for the progressive or non-progressive nature of the cancer. Second, well characterized Gleason 6 prostate cancer tissue samples may be used to generate reference Raman data sets from which a classification mode, based on principal component analysis, may be generated. Using this classification model, the progressive or non-progressive nature of a prostate cancer sample can be predicted.

Example 2

The example demonstrates the creation of a reference Raman database for reference progressive Raman data sets and reference non-progressive Raman data sets and the development of a classification model for Gleason 7 cancer tissue. In this example, 18 samples from a different series of case-control pairs of patients, diagnosed with Gleason 7 cancer; were selected for analysis. A case was defined as a patient who had prostate cancer characterized as Gleason 7 pattern and after the removal of the prostate went on to later develop metastatic disease. For purposes of this application, metastatic Gleason 7 tissue sample will be referred to as progressive Gleason 7 tissue sample. A control was defined as a patient having prostate cancer characterized as Gleason 7 pattern and after the removal of the prostate did not later develop metastatic disease. For purposes of this application, a non-metastatic Gleason 7 tissue sample will be referred to as non-progressive Gleason 7 tissue sample.

Figure 12:
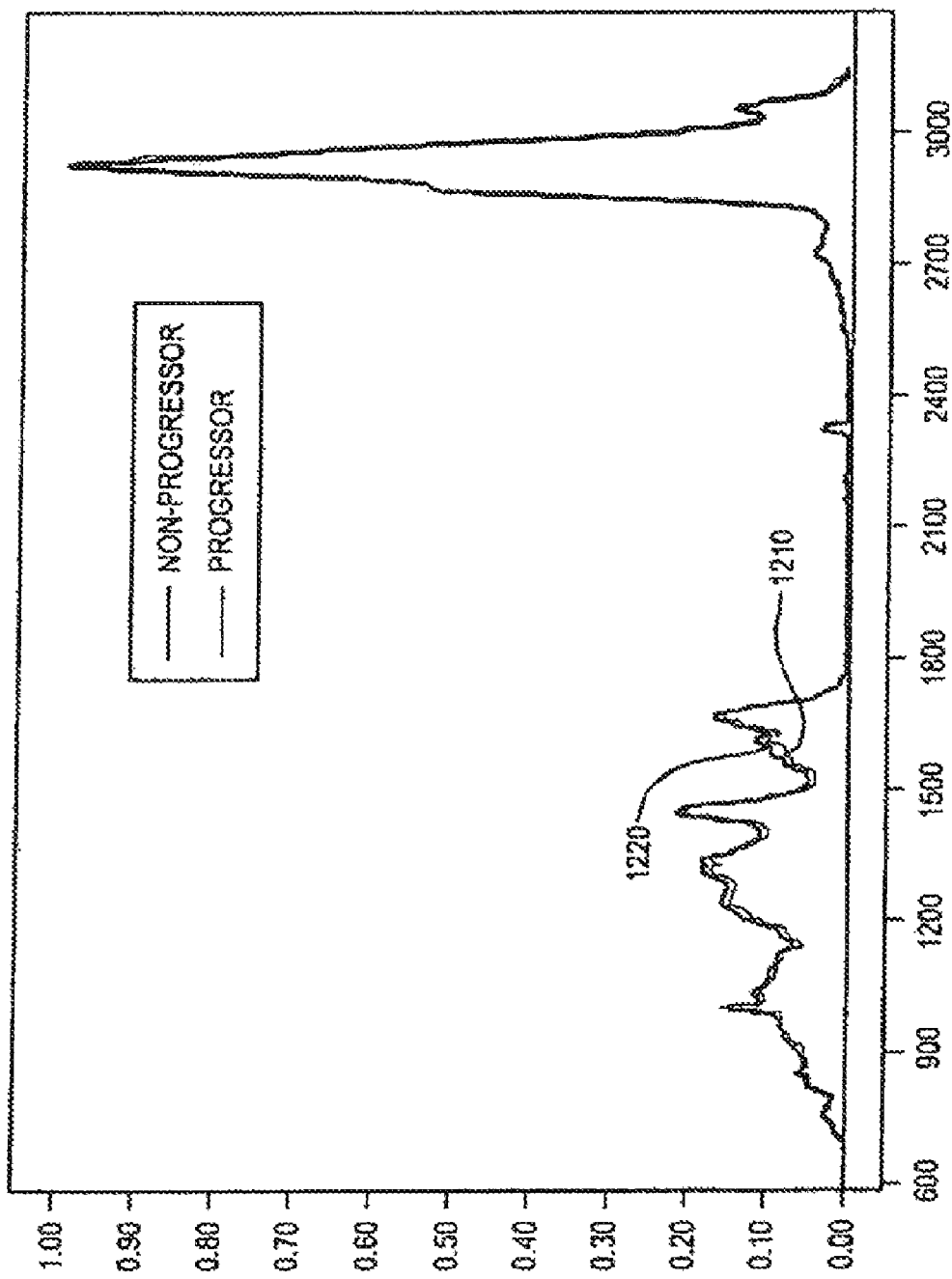
FIG. 12 illustrates mean Raman spectra for progressive Gleason 7 prostate cancer samples and non-progressive Gleason 6 prostate cancer samples.

Raman spectra were obtained for each case-control pair as discussed for the Gleason 6 tissue samples in Example 1. Raman spectra were obtained from approximately 20 regions of interest of each tissue section for the 9 unstained case-control (progressive-non-progressive) pairs. A total of 155 Raman dispersive spectra were obtained for the progressive tissue samples and a total of 154 Raman dispersive spectra were obtained for the non-progressive tissue samples. FIG. 12 illustrates the mean dispersive Raman spectra 1210 for the case pair tissue samples from patients with progressive Gleason 7 prostate cancer and the mean Raman spectra 1220 for the control pair tissue samples from patients with non-progressive Gleason 7 prostate cancer.

Figure 13:
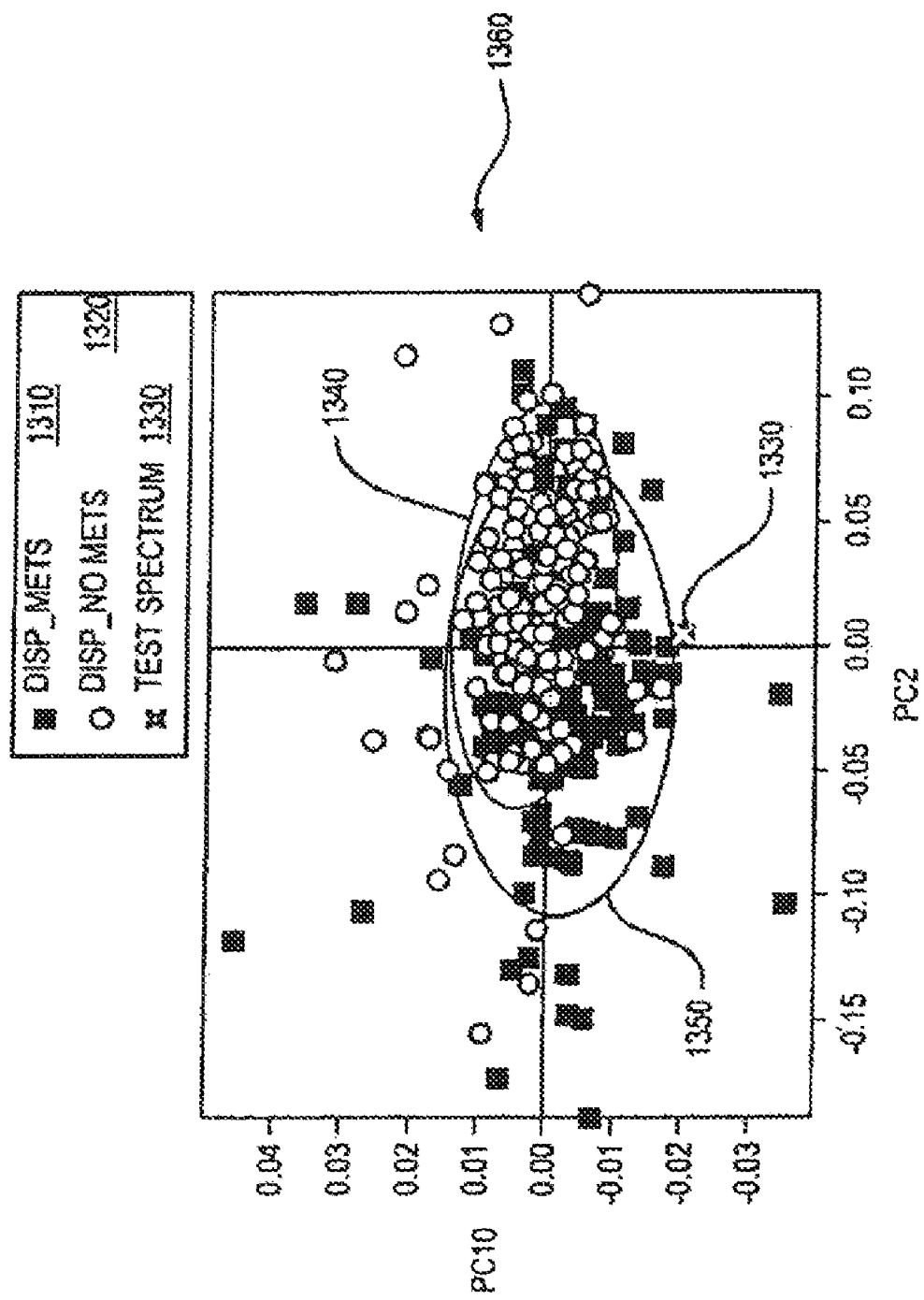
FIG. 13 illustrates an exemplary classification model for Gleason 7 prostate cancer samples.

Principal component analysis was applied to the Raman data sets for each progressive-non-progressive Gleason 7 pair. FIG. 13 illustrates the predetermined vector space obtained in this fashion for Gleason 7 progressive tissue 1310 and 1350 and Gleason 7 non-progressive tissue 1320 and 1340. The points labeled 1310 and 1350 mathematically describe the reference Raman spectra data sets collected for Gleason 7 progressive tissue. The points labeled 1320 and 1340 mathematically describe the reference Raman spectra data sets collected for Gleason 7 non-progressive tissue. Point 1330 mathematically describes the Raman spectrum obtained for the Gleason 7 test sample. The vector space, shown in FIG. 13, is a projection of the points in Principal Component space onto a single plane. In this projection there is a significant overlap between the groups. Though the data sets appear to overlap in this particular projection, the classification of a given test Raman measurement can be determined by considering all of the projections simultaneously, some of the projections, or even a single projection.

To demonstrate the feasibility of the methods of the present disclosure, each Raman spectrum, for the Gleason 7 tissue samples, was then classified as progressive tissue or non-progressive tissue by using a Leave-One-Out cross validation approach wherein a classification model (vector space) was generated with all of the Raman data sets except a single spectrum (test Raman data set). The classification model thus generated was used to classify the one spectrum which was left out. The process was repeated for all spectra. Statistics about how often the models generated correct results are shown in Table 2. For the 155 spectra for the progressive tissue samples, 140 were classified correctly as progressive and 15 were incorrectly classified as non-progressive. For the 154 spectra for the non-progressive tissue samples, 118 were classified correctly as non-progressive and 36 were incorrectly classified as progressive, as indicated in Table 2. For this classification, a sensitivity value of 90% was obtained and a specificity value of 77% was obtained.

| Sample | Gleason 7 Progressive | Gleason 7 Non-Progressive |
| --- | --- | --- |
| # of samples | 155 | 154 |
| Classified as progressive | 140 | 36 |
| Classified as non-progressive | 15 | 118 |

Example 3

A classification model as to progressive Gleason 7 cancer or non-progressive Gleason 7 cancer was also developed by extracting Raman spectra from regions of interest of a tissue sample identified as epithelium, stroma or nuclei tissue. There are different methods which can be used to select regions of interest for analysis within a data set representative of a tissue. These include manual selection by an expert (described below), automated selection using characteristics of the dataset itself (e.g. using Spectral Mixture Resolution to identify regions within the tissue which are epithelium or stroma), automated selection using analysis of some complimentary set of data (e.g. using the UV induced autofluorescence image to select regions of stroma and epithelium). These methods can be used alone or in combination. Moreover, tissue elements different from epithelium and stroma such as the epithelial-stromal junction (ESJ) can be targeted by similar methods.

Figure 14:
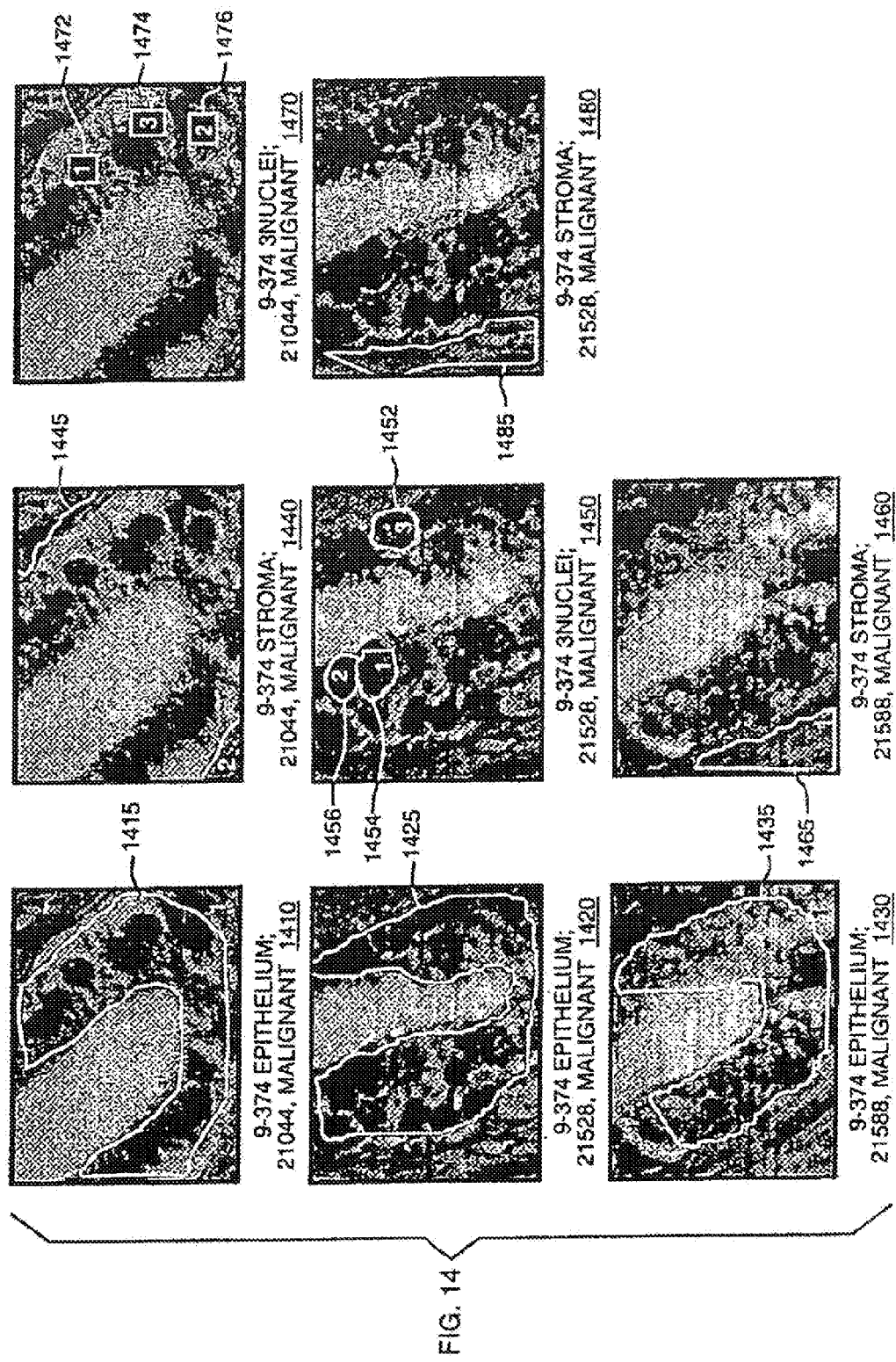
FIG. 14 illustrates various non-Raman images of Gleason 7 prostate cancer samples.

In this example, after consulting a pathologist, regions were drawn on the image using ChemImage Xpert software tools, specifically the lasso tool. The lasso tool enables the user to draw regions on the image corresponding to tissue components. The spectra associated with these regions are then saved and used for PCA analysis. FIG. 14 is an example of how this lasso tool is used and how the spectra associated with those regions were saved. FIG. 14 illustrates the various tissue areas 1410, 1420, 1430, 1440, 1450, 1460, 1470 and 1480 for a selected case. Epithelium regions 1415, 1425 and 1435 were identified for tissue samples 1410, 1420 and 1430, respectively. Stroma regions 1445, 1465, and 1485 were identified for tissue samples 1440, 1460 and 1480, respectively. Nuclei region 1452 was identified for tissue sample 1450. Nuclei regions 1472, 1474 and 1476 were identified for tissue sample 1470.

Figure 15:
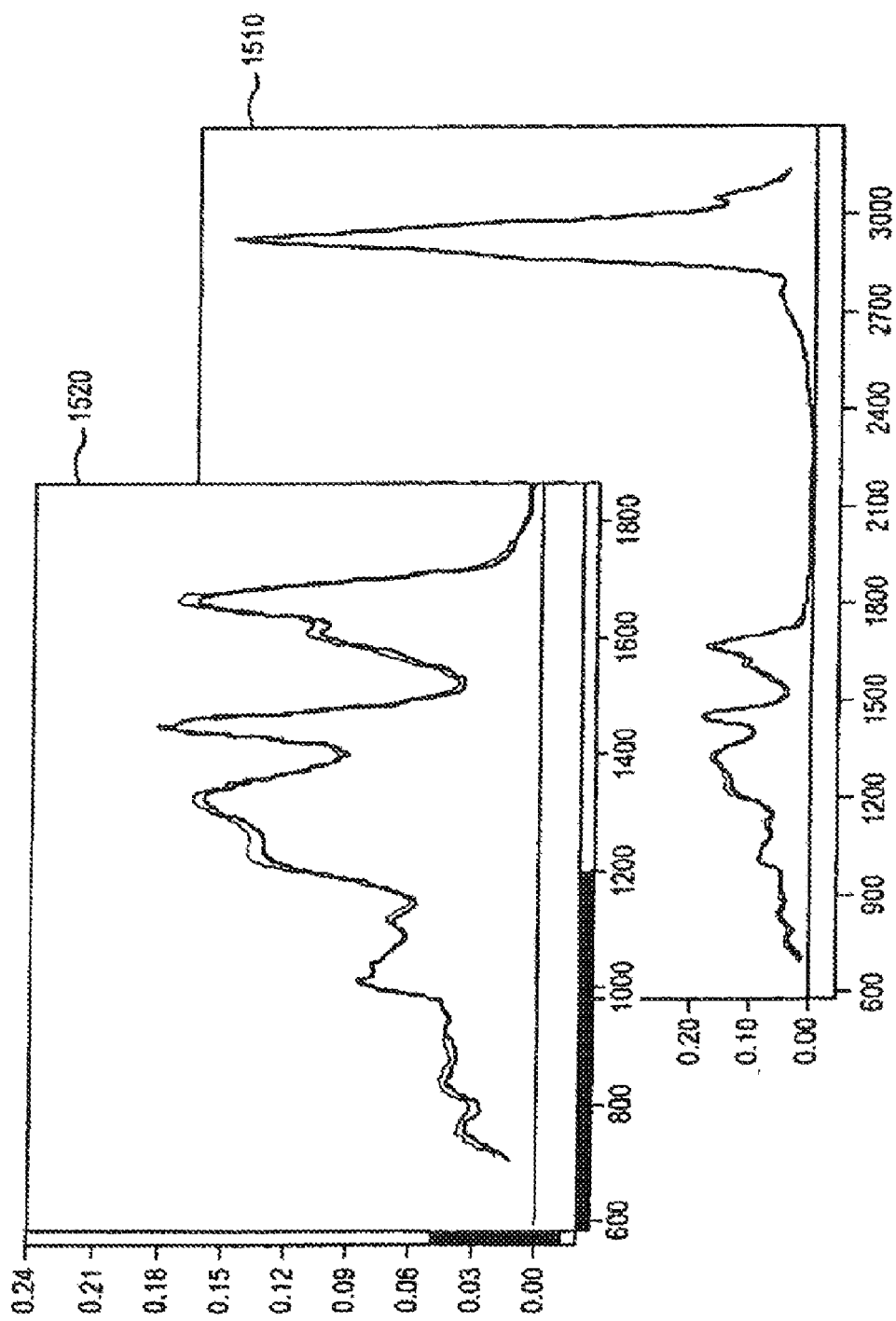
FIG. 15 illustrates an exemplary classification model for Gleason 7 prostate cancer samples.

FIG. 15 shows mean a Raman spectrum 1510 obtained for epithelium areas for progressive tissue samples and mean Raman spectrum 1520 obtained for non-progressive tissue samples. The mean spectra were generated from 55 spectra of epithelium areas for a progressive tissue sample and from 36 spectra of epithelium areas for non-progressive tissue sample. The spectra show slight differences in the region of 700 to 1800 $cm^{-1}$. These differences may reflect the different components of the epithelium tissue for progressive and non-progressive cancer.

Each spectrum was then classified as non-progressive Gleason 7 cancer or progressive Gleason 7 using a Leave-One-Out ("LOO") cross validation approach. In the LOO approach a model is built by transforming the Raman data sets into principal component space. All of the data except one measurement are used to create the space. Subsequent to the creation of the space, the measurement which was left out is classified by transforming it into the space and evaluating which group it is closest to. This evaluation can be performed using a measure of distance such as the Mahalanobis distance as used in this case. Alternative methods such as support vector machines can also be used to divide up the model space and determine where within the space the transformed test data lies. It is important to note that many different choices can be made in terms of the construction of a model space. These choices include parameters such as the number of principal components, wavelength ranges (which do not need to be contiguous) and others known to those skilled in the art.

As shown in Table 3, for the 55 spectra for the progressive Gleason 7 tissue samples, 22 were classified correctly as progressive Gleason 7 cancer and 33 were incorrectly classified as non-progressive Gleason 7 cancer. For the 36 spectra of the non-progressive tissue samples, 31 were classified correctly as non-progressive Gleason 7 cancer and 5 were incorrectly classified as progressive Gleason 7 cancer. For this classification, a sensitivity value of 40% was obtained and a specificity value of 86% was obtained.

| Sample | Gleason 7 Progressive | Gleason 7 Non-Progressive |
| --- | --- | --- |
| # of samples | 55 | 36 |
| Classified as progressive | 22 | 5 |
| Classified as non-progressive | 33 | 31 |

This method of extracting Raman spectra from epithelium, stroma or nuclei regions of interest was refined by further subsecting of the data. This was performed by taking the spectra from epithelium from regions a pathologist calls Gleason 3 pattern and separating those spectra from epithelium from regions a pathologist would call a Gleason 4 pattern. Thus the epithelium can be divided into two groups based on local histology. This results in a group of spectra from epithelium in tissues locally consistent with Gleason 3 pattern for both the progressors and the non-progressors. A similar set of spectra are available for Gleason 4, pattern epithelium and Gleason 3 and Gleason 4 pattern stroma.

Figure 16:
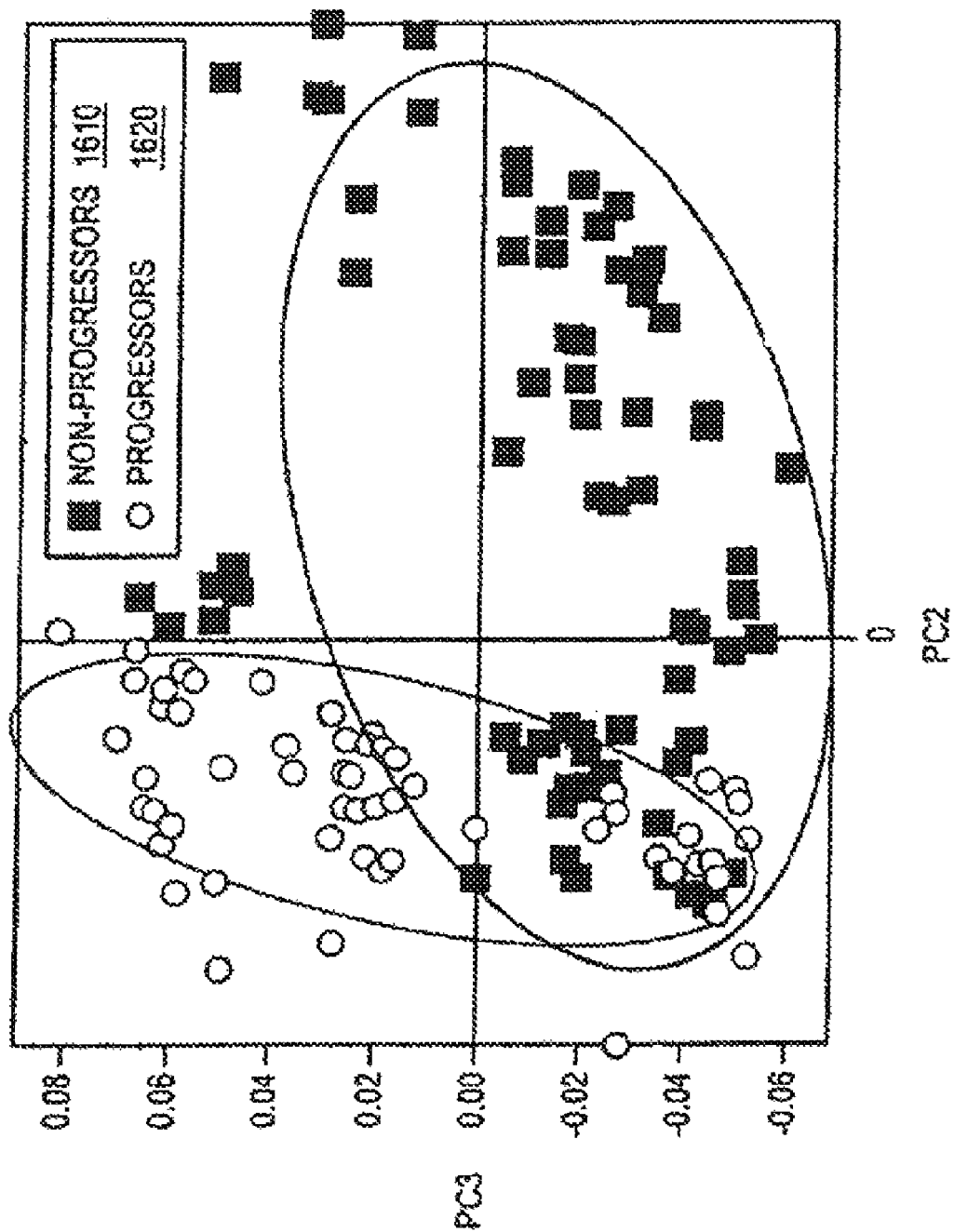
FIG. 16 illustrates mean Raman spectra obtained for epithelium tissue for Gleason 7 prostate cancer samples.

FIG. 16 shows a scatter plot of the spectra from regions of images of epithelial cells in Gleason 3 pattern areas for progressors 1620 and non-progressors 1610 in PCA space. Statistical analysis of the x and y coordinate of this plot shows that the distribution of the progressors and Non-progressors are distinct to a statistically significant degree.

Leave-One-Out (LOO) analysis as described above yields the results below, leading to a sensitivity of 95% and a specificity of 91%.

| Sample | Gleason 7 Progressive | Gleason 7 Non-Progressive |
| --- | --- | --- |
| # of regions of interest | 58 | 72 |
| Classified as progressive | 53 | 3 |
| Classified as non-progressive | 5 | 69 |

In similar fashion the stroma of Gleason 3 pattern areas and also the epithelium and stroma of Gleason 4 pattern areas can be evaluated. Note that the performance of this approach is significantly better than the wide field dispersive spectra discussed in Example 2, and the image spectra of epithelium only discussed in Example 3.

As for the Gleason 6 prostate samples, this data shows that Raman spectroscopy has the capability of detecting differences in progressive and non-progressive Gleason 7 prostate samples. Based on these distinctions, a classification model can be built from well characterized Example 4

This example illustrates the classification of various areas of a tissue sample by using a spectral mixture resolution algorithm to analyze a Raman image of a test sample. Using a spectral mixture resolution algorithm, it is possible to identify regions of interest for spectral selection in lieu of manual selection used in Example 3. This approach requires reference Raman data sets for a variety of known tissue types, cells or compositions. The concentration images generated in this example can also be used as part of a classification scheme. A simple example of this approach is to take the ratio of the total amount of a one component to another. This can be performed by, for each component, adding up and appropriately normalizing all the points in the concentration image for that component (e.g. epithelium from progressors) and taking the ratio of this number to the same calculation for the concentration image of another component (e.g. epithelium from progressors). This is not limited to simple ratio as in some cases algebraic manipulation of the total amounts of the components may be more indicative of metabolic or disease state.

Another important point in this example is that the components chosen here are based on histological interpretation (epithelium, stroma, etc.) and disease status (progressive vs. non-progressive) and not on component chemicals (DNA, collagen, etc.), or chemical classes (proteins, lipids etc.). Use of complex components defined based on clinical parameters has the effect of integrating over the details of local biochemical interactions and focusing on the desired endpoint which in this case is metabolic state or disease classification.

Figure 17:
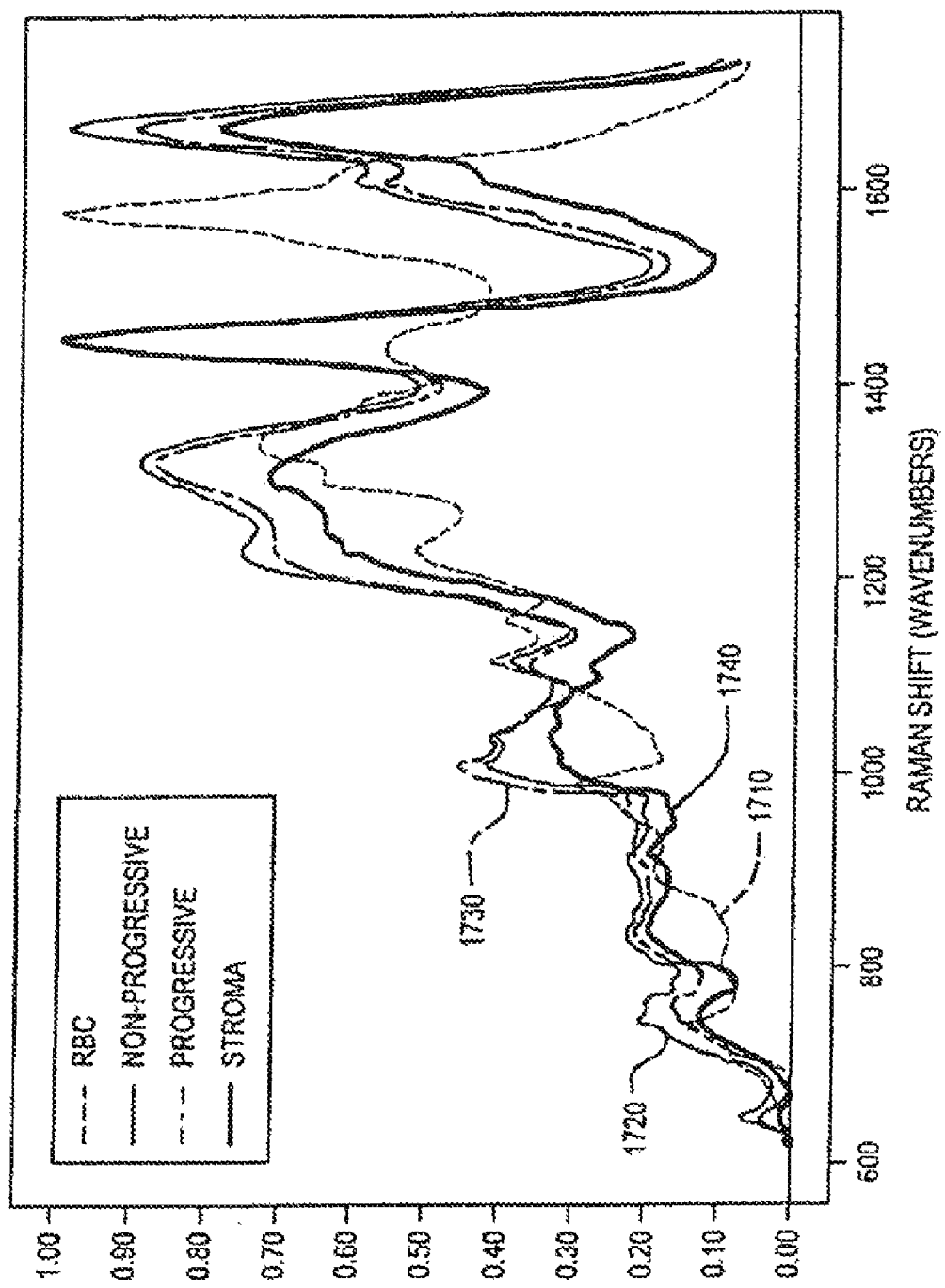
FIG. 17 illustrates reference Raman spectra for red blood cells, stroma, progressive Gleason 7 prostate cancer samples and non-progressive Gleason 7 prostate cancer samples.

FIG. 17 shows the reference Raman spectra for red blood cells (RBC) 1710, non-progressive prostate cancer tissue taken from epithelium 1720, progressive prostate cancer tissue taken from epithelium 1730, and stroma tissue 1740 which were used to classify the Raman images. Additional reference Raman spectra may be used for other tissue, cells or compositions found in sample under analysis.

Figure 18:
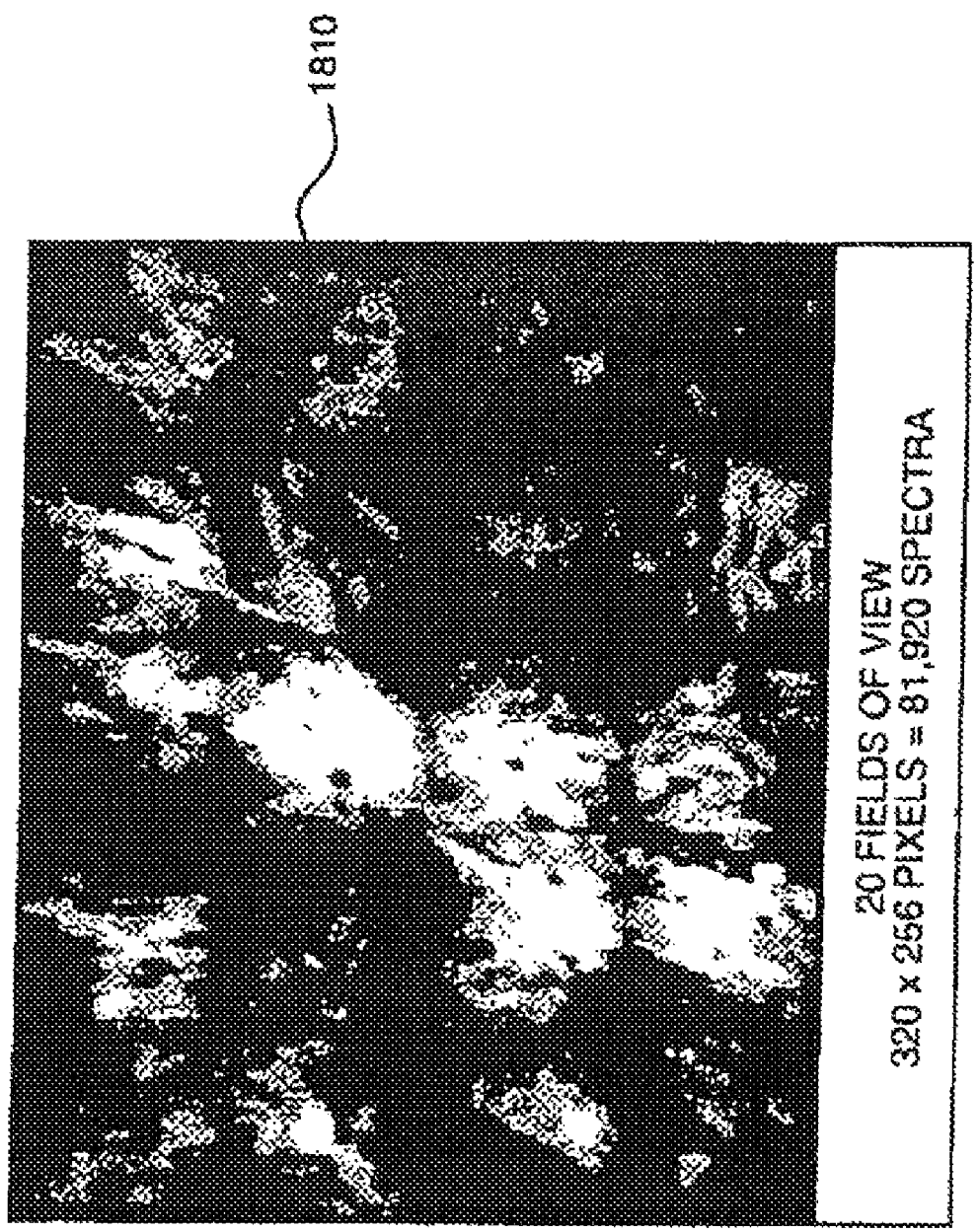
FIG. 18 illustrates a Raman image montage for a Gleason 7 prostate sample.

FIG. 18 shows an image montage 1810, taken at a Raman shift value of 2930 cm$^{-1}$ for a Gleason 7 prostate tissue sample. Because the Raman field of view is smaller than the size of the glass slide mounted tissue sample, the sample was divided into, twenty areas for Raman data collection. Spatially accurate wavelength resolved spectra and wavelength resolved spatially accurate images were obtained for each of the twenty areas. The final image (an example of a wavelength resolved spatially accurate image) is composed of 20 regions stitched together to allow visualization of large scale structural features. The image was analyzed using a spectral mixture resolution algorithm and the reference Raman spectra shown in FIG. 17.

FIGS. 19-23 show the results of the analysis of the Gleason 7 prostate tissue sample of FIG. 18 as concentration images. A concentration image encompasses all of the spectral information, not just one single Raman shift. Each frame of a concentration image describes where in the field of view the reference spectral signal appears. A digital image of the unstained sample is also shown 1920 in each of FIGS. 19-23, along with the corresponding H&E stained sample that was obtained after the Raman data was acquired.

Figure 19:
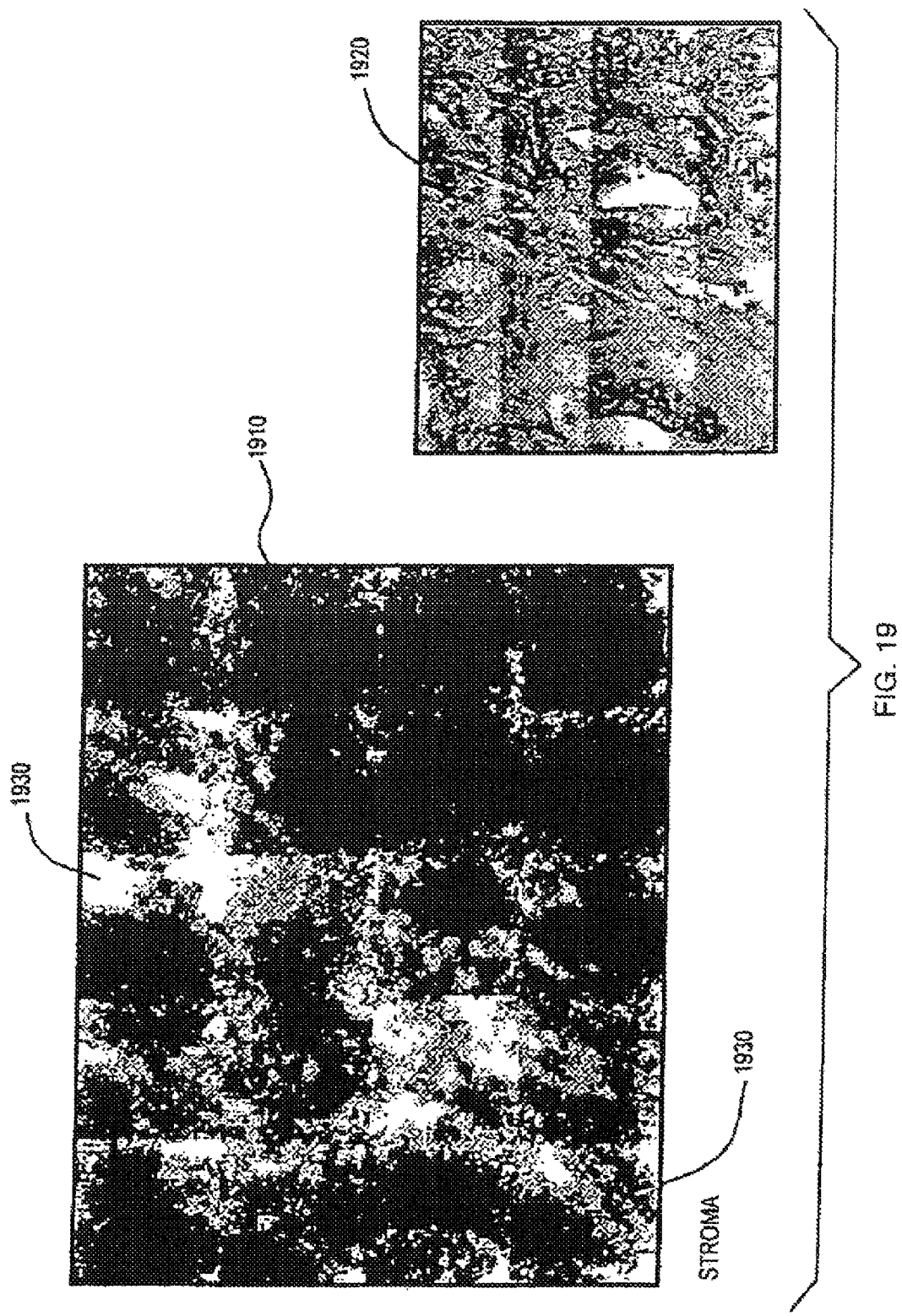
FIG. 19 illustrates an image montage, obtained by spectral mixture resolution, for a Gleason 7 prostate sample showing areas of stroma tissue.
Figure 20:
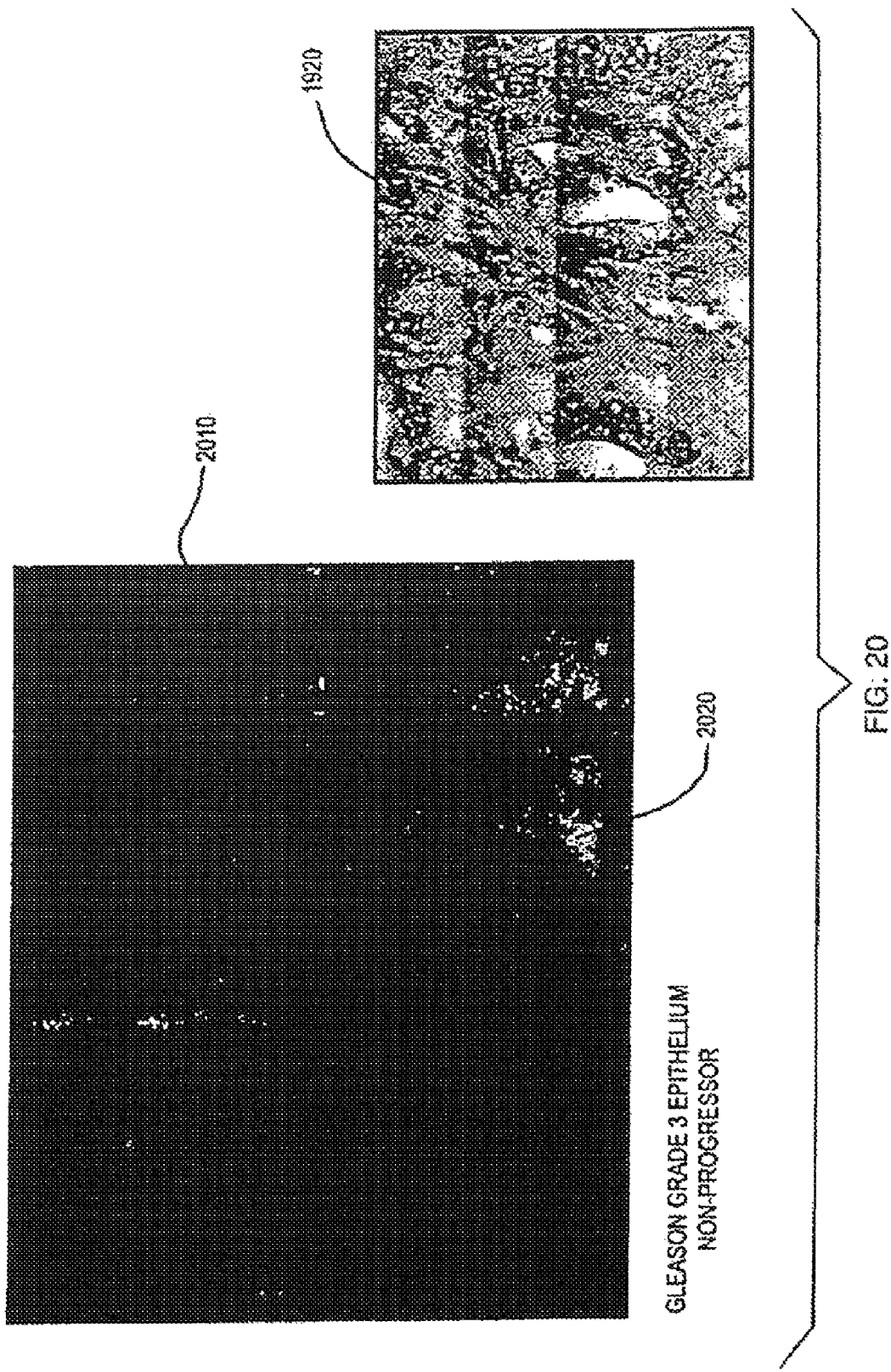
FIG. 20 illustrates an image montage, obtained by spectral mixture resolution, for a Gleason 7 prostate sample showing areas of epithelium tissue of a non-progressive Gleason 7 prostate cancer sample.
Figure 21:
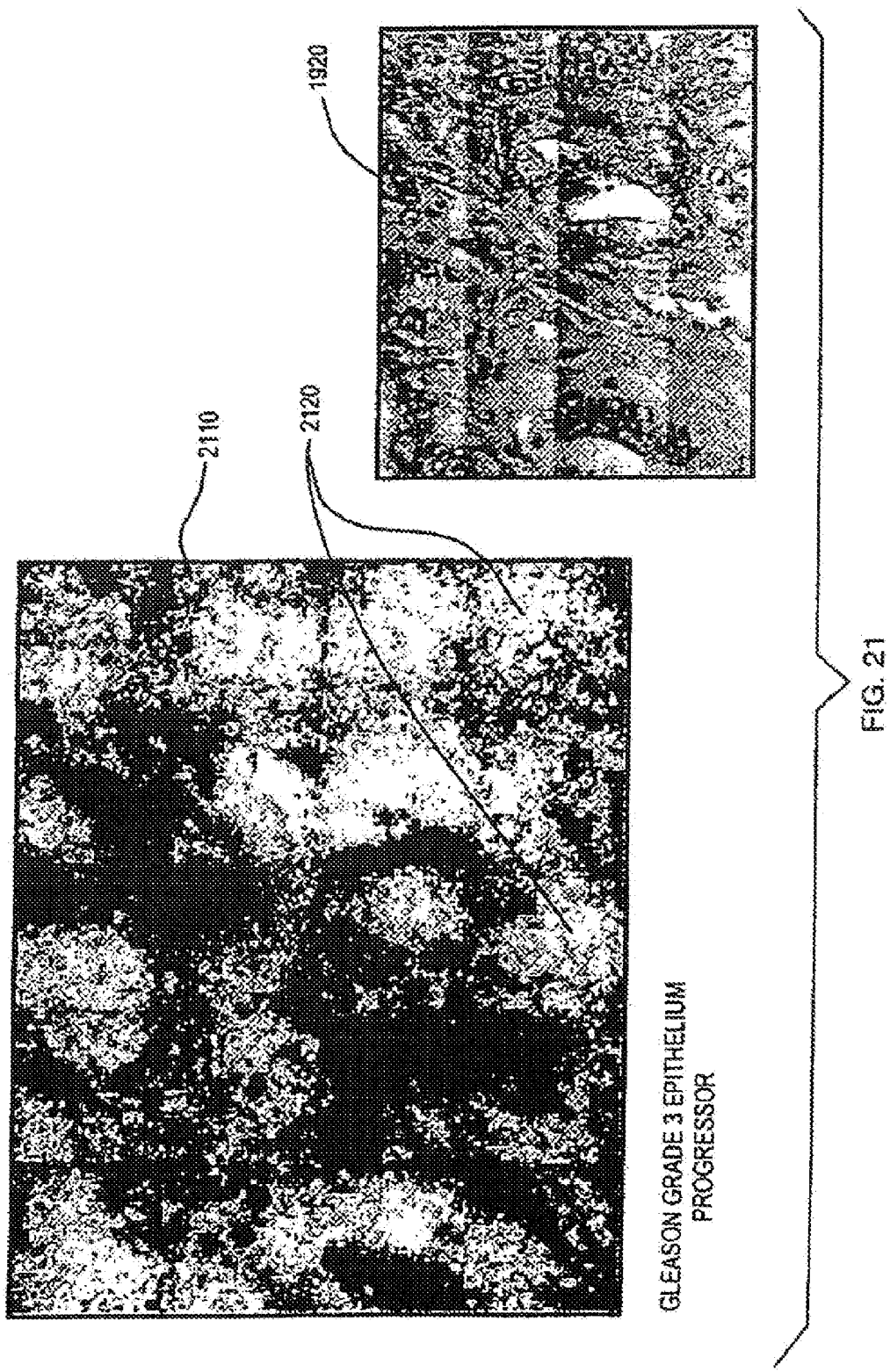
FIG. 21 illustrates an image montage, obtained by spectral mixture resolution, for a Gleason 7 prostate sample showing areas of epithelium tissue of a progressive Gleason 7 prostate cancer sample.
Figure 22:
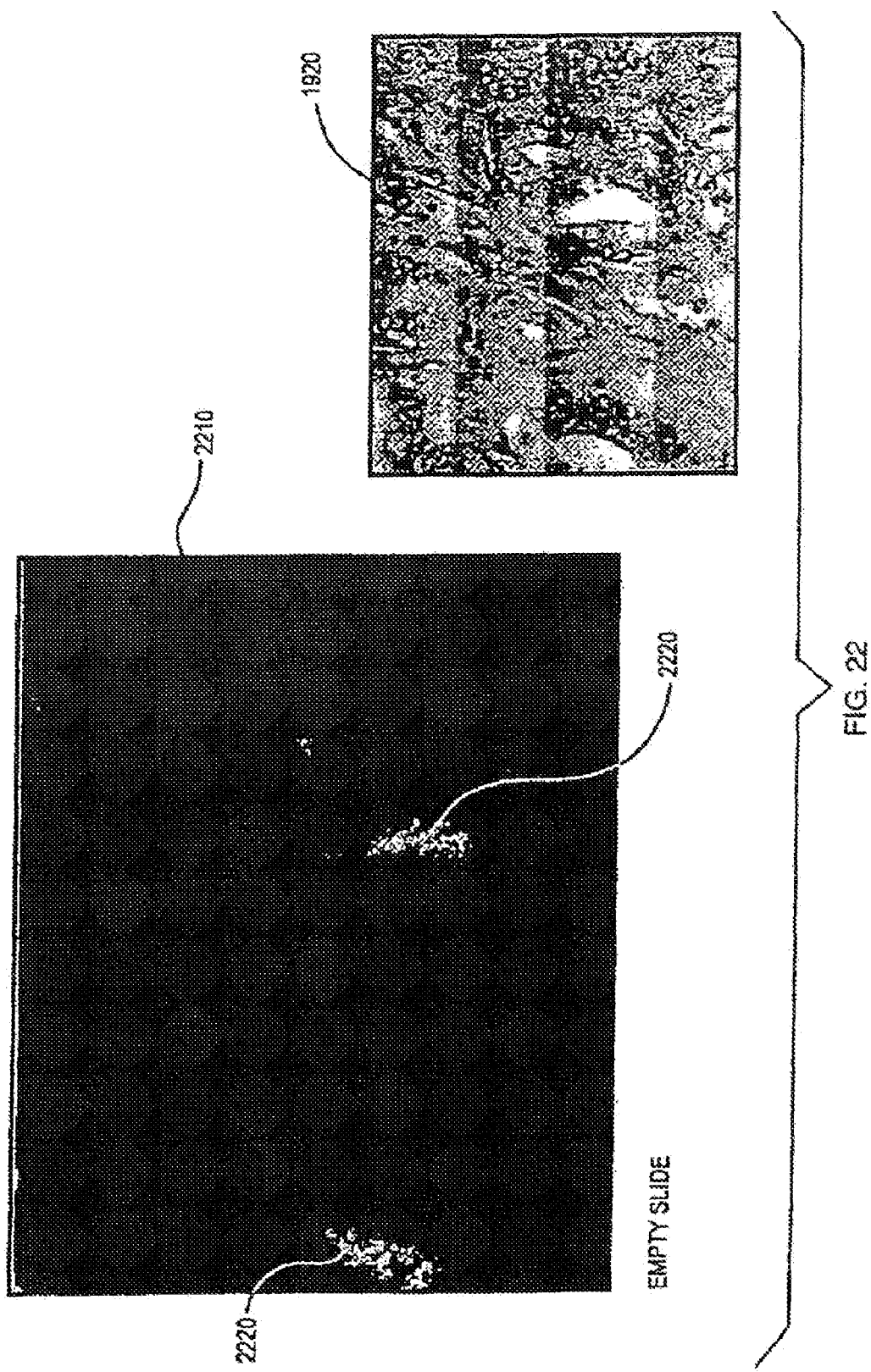
FIG. 22 illustrates an image montage, obtained by spectral mixture resolution, for the empty slide areas of a Gleason 7 prostate sample.
Figure 23:
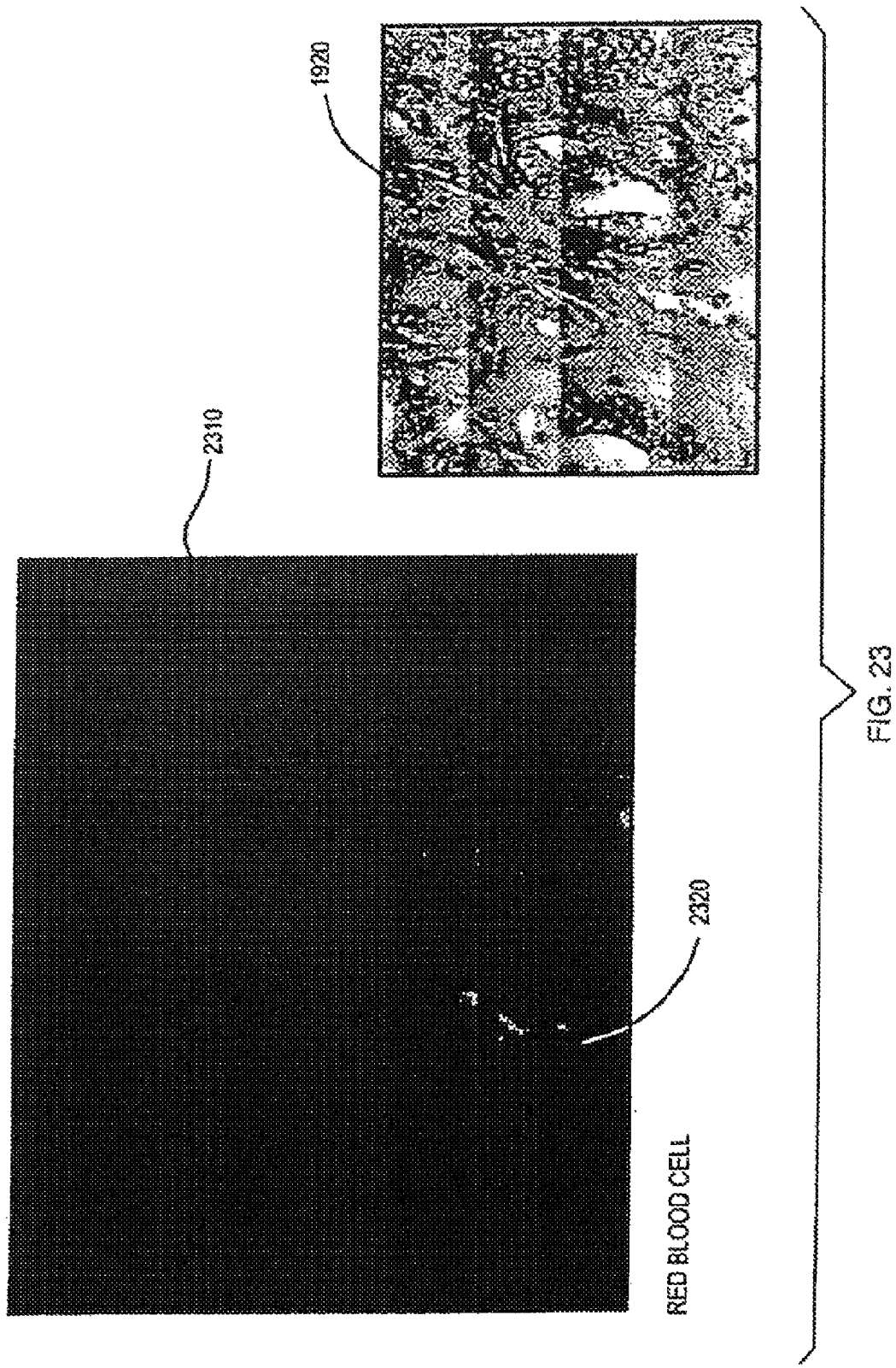
FIG. 23 illustrates an image montage, obtained by spectral mixture resolution, for a Gleason 7 prostate sample showing areas of red blood cells of a progressive Gleason 7 prostate cancer sample.

The concentration images were generated by standard chemometric tools. The concentration image 1910 of FIG. 19 shows areas of white 1930 which represent stroma tissue. In FIG. 20, the concentration image 2010 shows areas of Gleason grade 3 epithelium non-progressive tissue indicated by the white areas 2020. FIG. 21 shows a concentration image 2120 where areas of Gleason grade 3 epithelium progressive tissue are indicated by the white areas 2120. FIGS. 22 and 23 show concentration images 2220 and 2310 where the white areas 2120 indicate blank areas of the glass slide and white areas 2320 indicate red blood cells, respectively. These results show it is not only possible to identify the components of a Gleason 7 tissue sample but also to map the sample as to the location of the components, in particular the epithelium non-progressive and progressive tissue.

Figure 24:
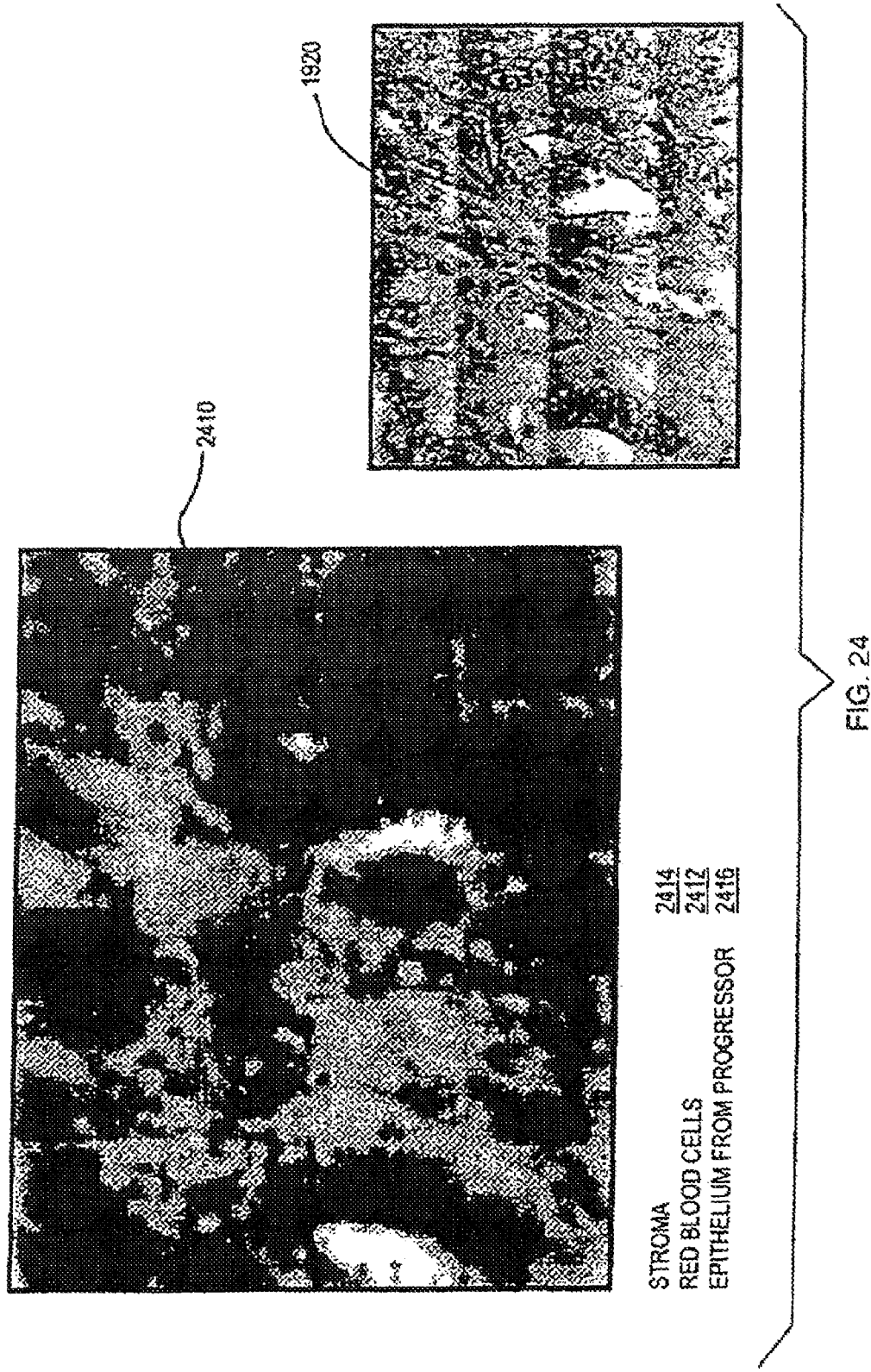
FIG. 24 illustrates a color enhanced Raman molecular image of a progressive Gleason 7 prostate cancer sample.

The results of FIGS. 19-23 were combined to generate a color enhanced molecular image of the Gleason 7 prostate tissue samples. This color enhanced image based on the fusion of different component concentration images is referred to as a molecular image, or alternatively as a Raman molecular image because the contrast which gives rise to the color is due to the molecular environment of the sample and is detected through Raman scattering measurements. In the color enhanced molecular image 2410 of FIG. 24, the red area 2412 indicates red blood cells, the green area 2414 indicates the stroma tissue and the blue area 2416 indicates the epithelium from progressive cancer tissue.

Example 5

Figure 25:
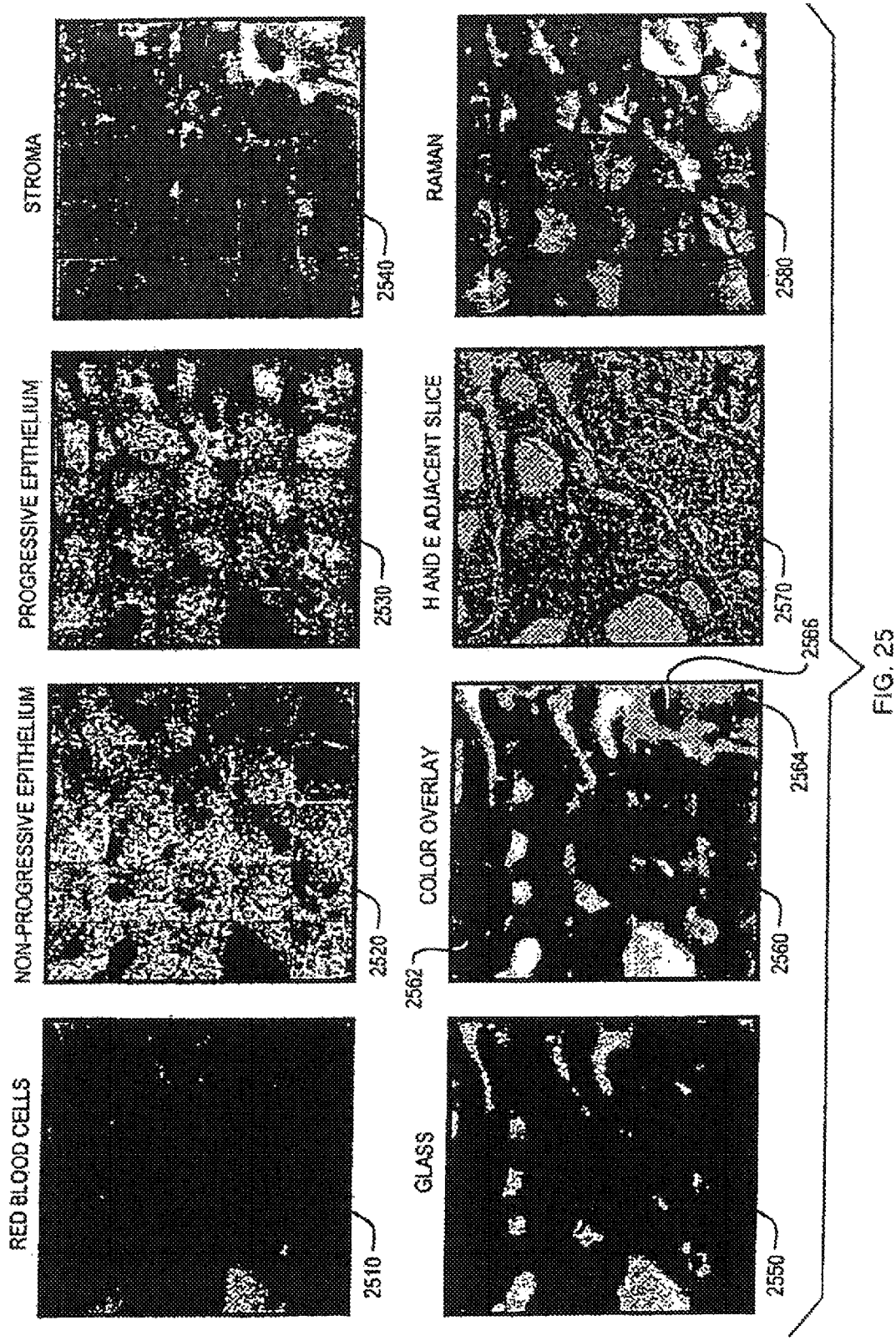
FIG. 25 illustrates several images of a Gleason 7 prostate cancer sample.

FIG. 25 illustrates the classification of tissue samples from a Gleason 7 case using spectral mixture resolution. Areas in each tissue sample were classified as red blood cells, non-progressive epithelium tissue, progressive epithelium tissue, or stroma tissue as described in Example 4. FIG. 25 shows eight different concentration images for a progressive Gleason 7 prostate sample. Concentration image 2510 illustrates red blood cells by the white areas. Concentration image 2520 illustrates white areas representative of non-progressive epithelium cancer tissue. The white areas of concentration image 2530 illustrate progressive epithelium cancer tissue. Stroma tissue is illustrated by the white areas of concentration image 2540. The glass slide is illustrated by the white area of concentration image 2550. A stained sample adjacent tissue slice is shown in image 2570 and a Raman image of the tissue sample is shown in image 2580. Concentration image 2560 shows a color enhance image to represent the various types of tissue found in the sample where the red areas 2562 indicates the location of epithelium from non-progressive tissue, the green areas 2564 indicates the location of stroma tissue, and the blue areas 2566 indicates the location of epithelium from progressive tissue. As in Example 4, these results show it is possible to identify the presence and location of stroma tissue, blood cells and epithelium tissue for progressive and non-progressive cancer samples.

The methods of the present disclosure may be applicable to a variety of cancer where Raman scattering indicates a difference between normal and cancer tissue as shown by the following examples which are intended to be representative and not exhaustive.

Example 6

Figure 26:
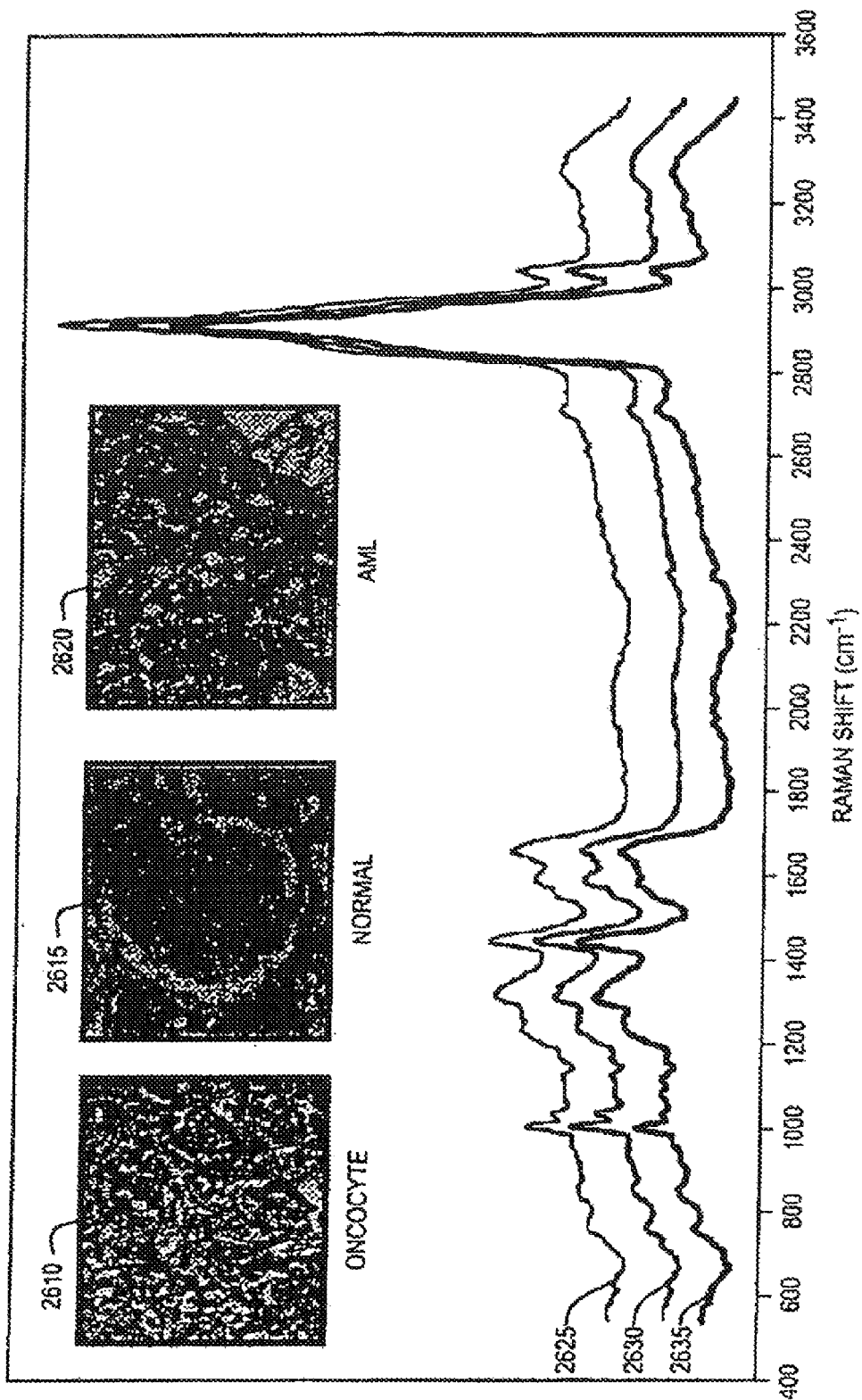
FIG. 26 illustrates several non-Raman images and Raman spectra of kidney tissue.

FIG. 26 illustrates stained images and Raman spectra for various type of kidney tissue. Image 2610 shows a stained sample of kidney tissue showing evidence of oncocyte cell and an associated Raman spectrum 2625. Image 2615 shows a stained sample of normal kidney tissue. Raman spectrum 2635 corresponds to normal kidney tissue. Image 2620 shows a stained sample of angiomyolipoma tissue taken from a kidney and its associated Raman spectrum 2630.

Example 7

Figure 27:
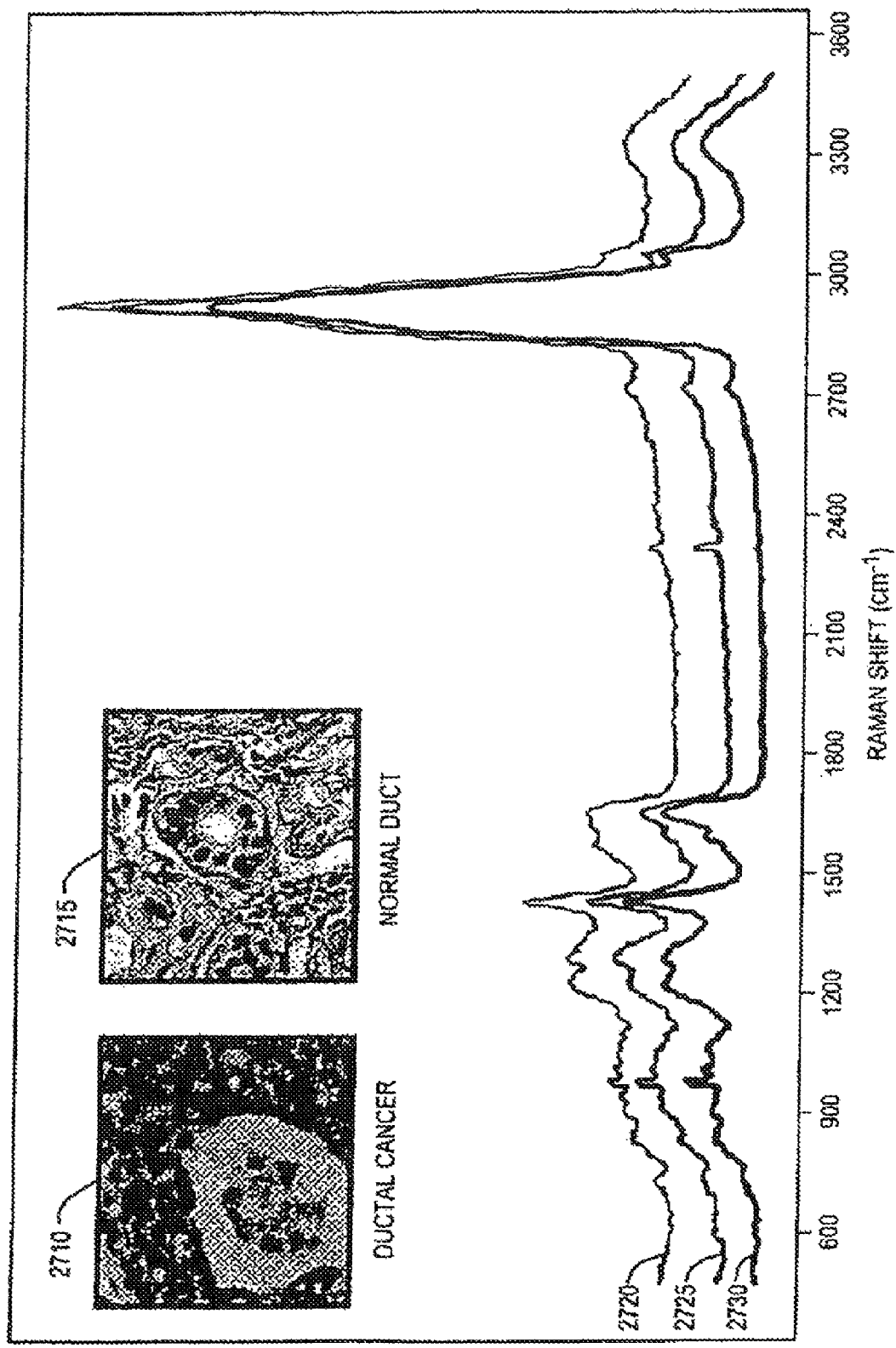
FIG. 27 illustrates several non-Raman images and Raman spectra of breast tissue.

FIG. 27 illustrates stained images and Raman spectra for breast tissue. Image 2710 shows a stained sample of breast tissue characteristic of ductal cancer. The corresponding Raman spectrum is shown by 2730. Raman spectrum 2625 shows a second spectrum of a cancerous breast tissue. Image 2715 shows an image of normal breast tissue and its associated Raman spectrum 2720.

Example 8

Figure 28:
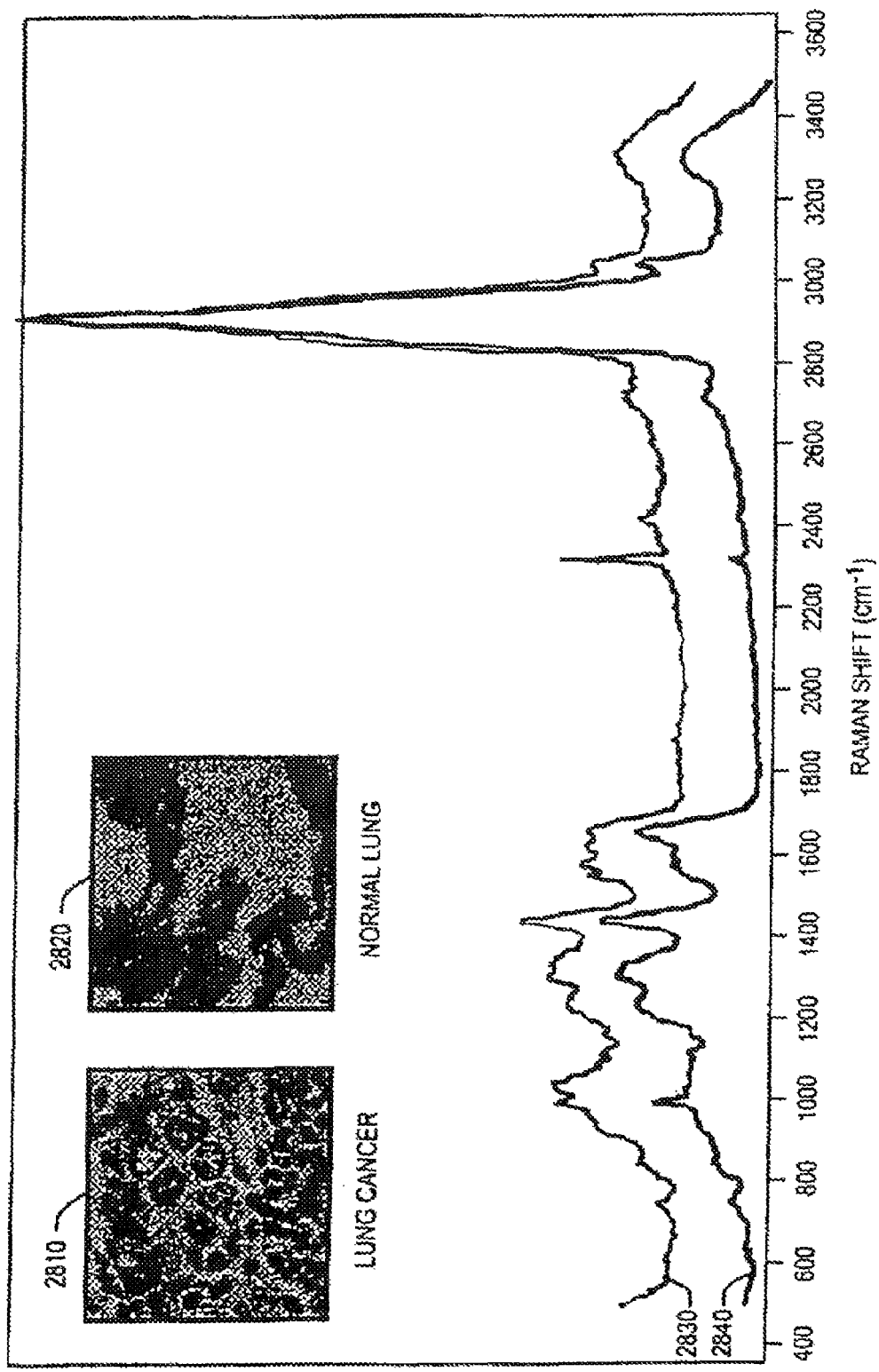
FIG. 28 illustrates several non-Raman images and Raman spectra of lung tissue.

FIG. 28 illustrated stained images and Raman spectra for lung tissue. Image 2810 shows a stained sample of cancerous lung tissue. The corresponding Raman spectrum is shown by 2840. Image 2820 shows an image of normal lung tissue and its associated Raman spectrum 2840.

The data from Examples 6-8 suggests that differences in the Raman spectra for the well characterized diseased or non-diseased tissue may be used to develop a classification model for a disease, including kidney cancer, breast cancer and/or lung cancer. From this classification model, it may be possible to determine whether a test tissue sample is diseased or normal. Furthermore, the differences in the non-Raman images of diseased or non-diseased tissue may be coupled with a Raman classification model for such determination.

Example 9

Figure 29:
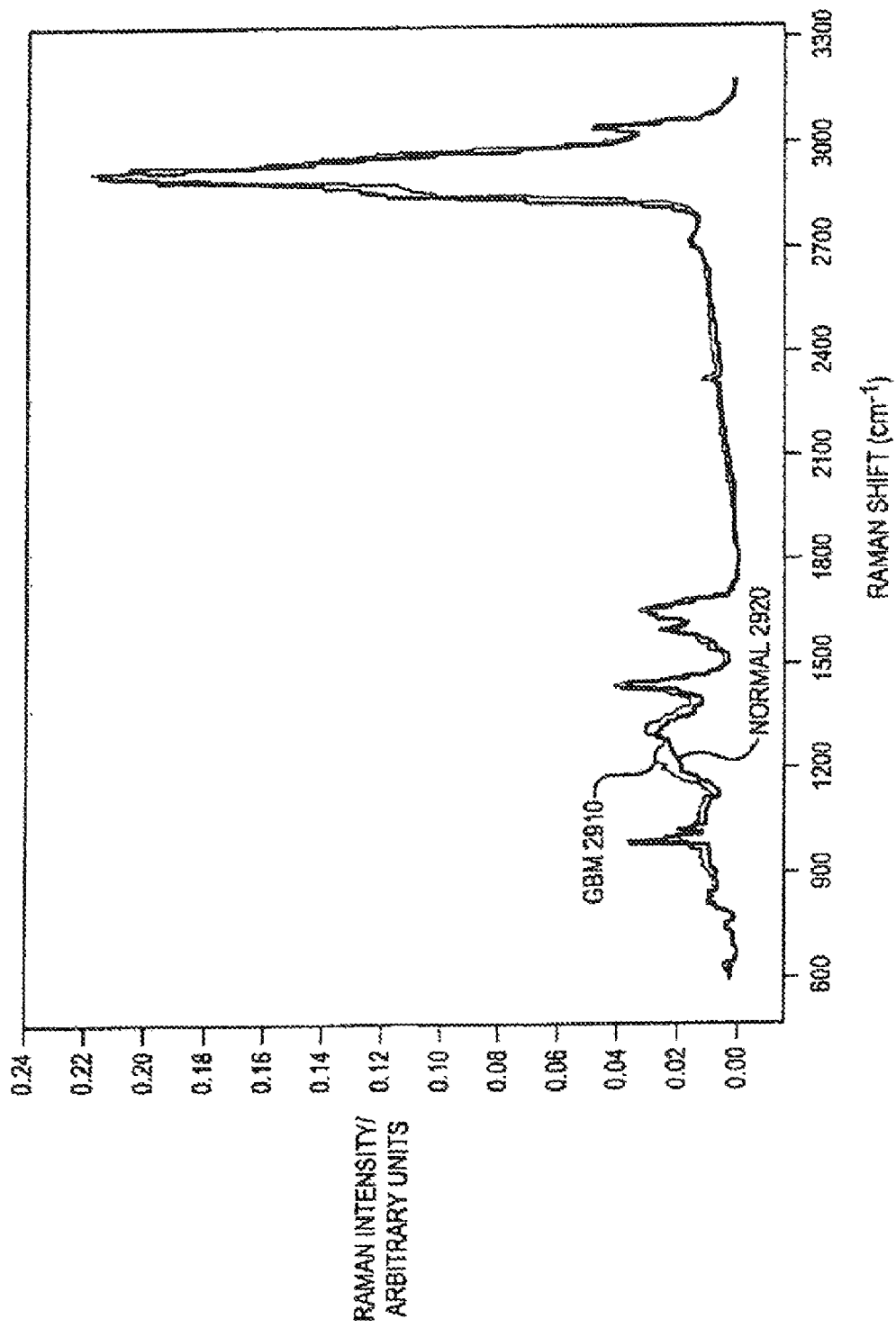
FIG. 29 illustrates several non-Raman images and Raman spectra of brain tissue.

FIG. 29 shows Raman spectra for normal brain tissue 2910 and Glioblastoma Multiforme tissue 2920. These spectra show observable differences in the region of 1100-1400 $cm^{-1}$.

Example 10

Figure 35:
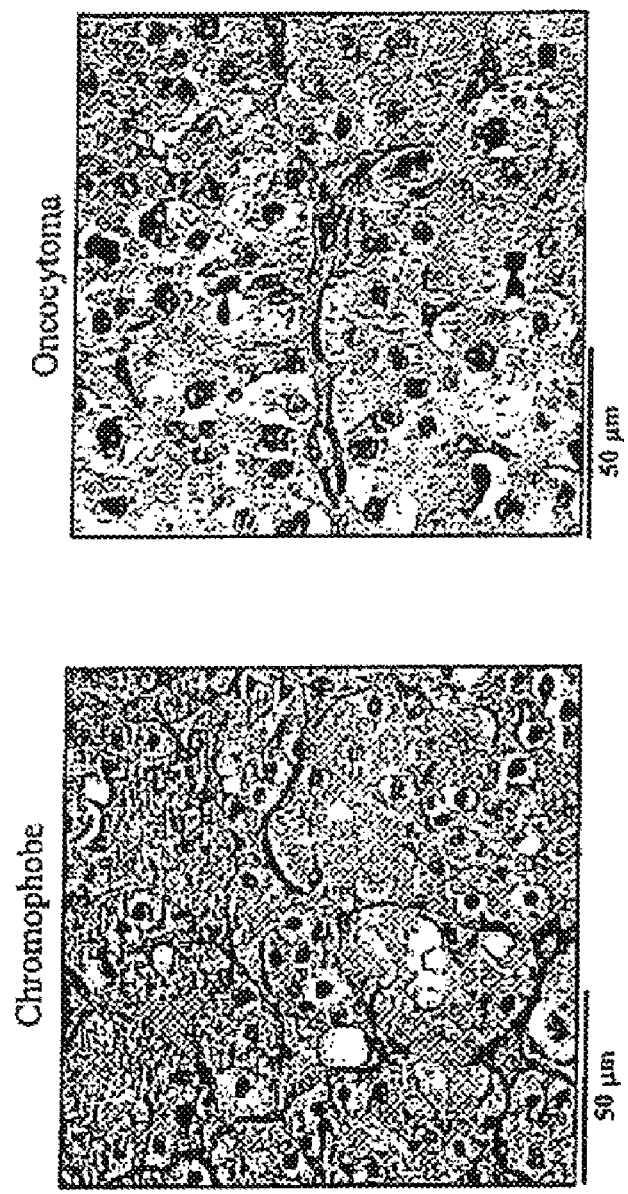
FIG. 35 illustrates bright field images of tissue samples identified as having a renal oncocytoma disease state and a chromophobe renal cell carcinoma disease state.
Figure 36:
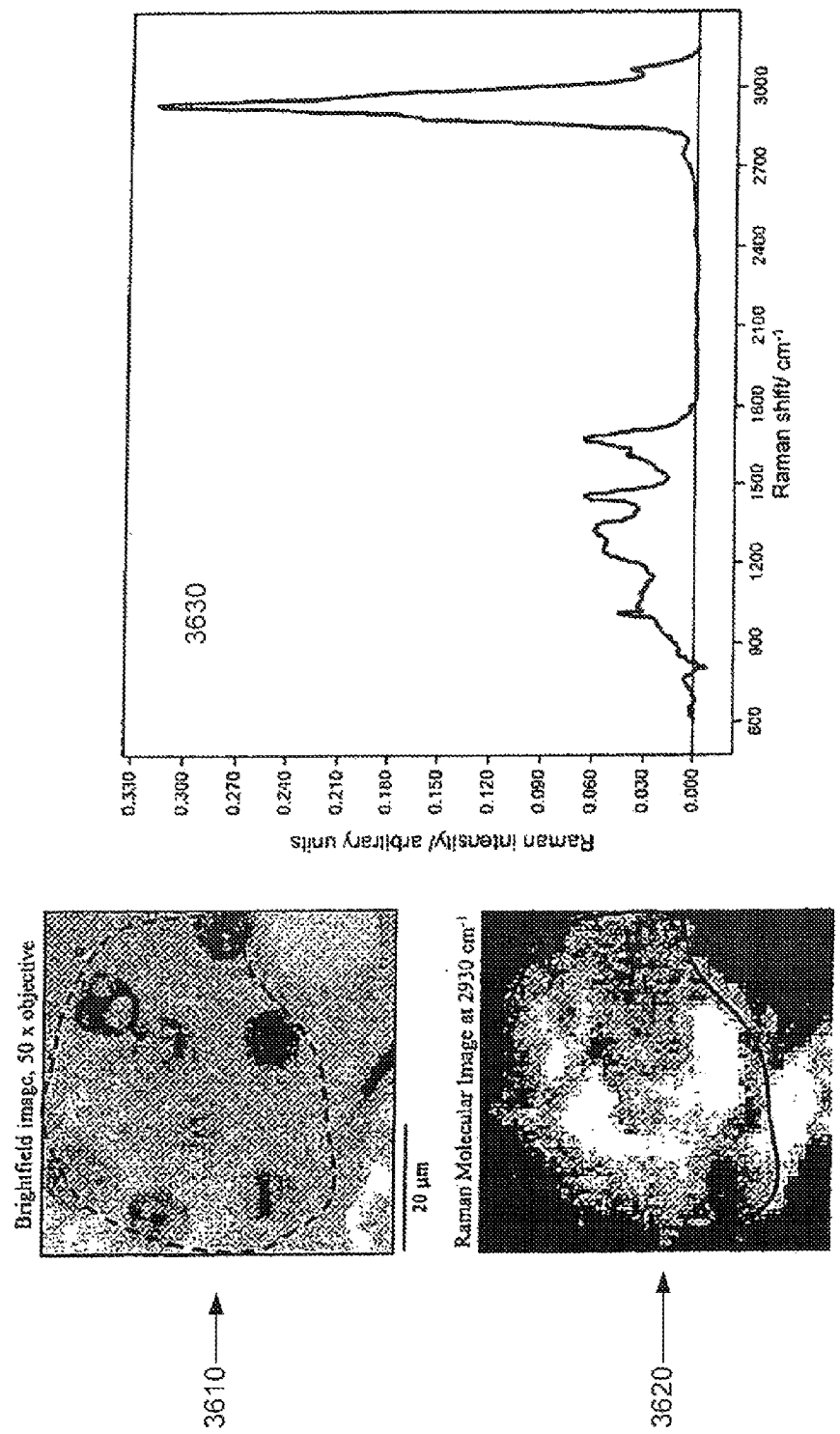
FIG. 36 illustrates a bright field image, a Raman image and a Raman spectrum of a renal oncocytoma sample.

The example demonstrates the creation of a reference Raman database having reference Raman data sets associated with renal oncocytoma disease ("OC") and chromophobe renal carcinoma disease ("ChRCC") as identified by a pathologist. Studies were conducted on eight (8) OC and eight (8) ChRCC cases of renal tissue. FIG. 35 illustrates bright field images for a OC sample 3520 and ChRCC sample 3510 stained with H & E for typical histopathologic examination. Regions of interest typical of OC and ChRCC were noted by a pathologist on adjacent H & E stained tissue sections and subsequently located on the unstained tissue sections. For each sample, 4-9 regions of interest ("ROI") of typical OC and ChRCC were identified for obtaining Raman data sets which were acquired on the ChemImage Falcon II™ imaging System with 532 nm excitation, using 50× microscope objective magnification. The Raman data sets corresponded to a plurality of spatially accurate wavelength resolved images (collectively "Raman images"). A reference data set is illustrated in FIG. 36 for a bright field image 3610 of a ROI of an OC sample from which a Raman image 3620 and a Raman spectrum 3630 were acquired. Note that the images in FIG. 36 are smaller than the images shown in FIG. 35 as the Raman images (one of which is shown in FIG. 35) were collected from fields of view approximately 50 µm in diameter. Raman images were preprocessed to take into account dark current, instrument response, flat-fielding of the light and baseline corrections. Once preprocessed, a plurality of reference Raman spectra were extracted from Raman images by selecting pixel data associated only to epithelial cells within the selected ROI. For each ROI, one reference Raman spectrum was extracted. In total, 57 OC and 57 ChRCC reference Raman spectra were extracted from the reference Raman images. Mean Raman spectra were obtained as described in this example, for the OC samples and ChRCC, are illustrated in FIG. 30. The most distinguishing features in the spectra may be in the "fingerprint" regions, specifically the regions between 900-1155 $cm^{-1}$ (3030) and 1530-1850 $cm^{-1}$ (3040).

Principal component analysis was applied to the Raman data sets for the eight (8) OC and eight (8) ChRCC cases of renal tissue. FIG. 31 illustrates a scatter plot in a predetermined vector space or a projection of the vector space onto the two coordinates (PC2 and PC3) for OC tissue and ChRCC tissue. The points labeled 3110 mathematically describe the reference Raman spectra data sets collected for the OC samples. The points labeled 3120 mathematically describe the reference Raman spectra data sets collected for the ChRCC samples. With a J3 value of 3.97, the distinction between the two classes, OC and ChRCC, is clear. This data indicates that Raman imaging may be used to generate a classification model which may be used to distinguish OC and ChRCC samples.

Figure 37:
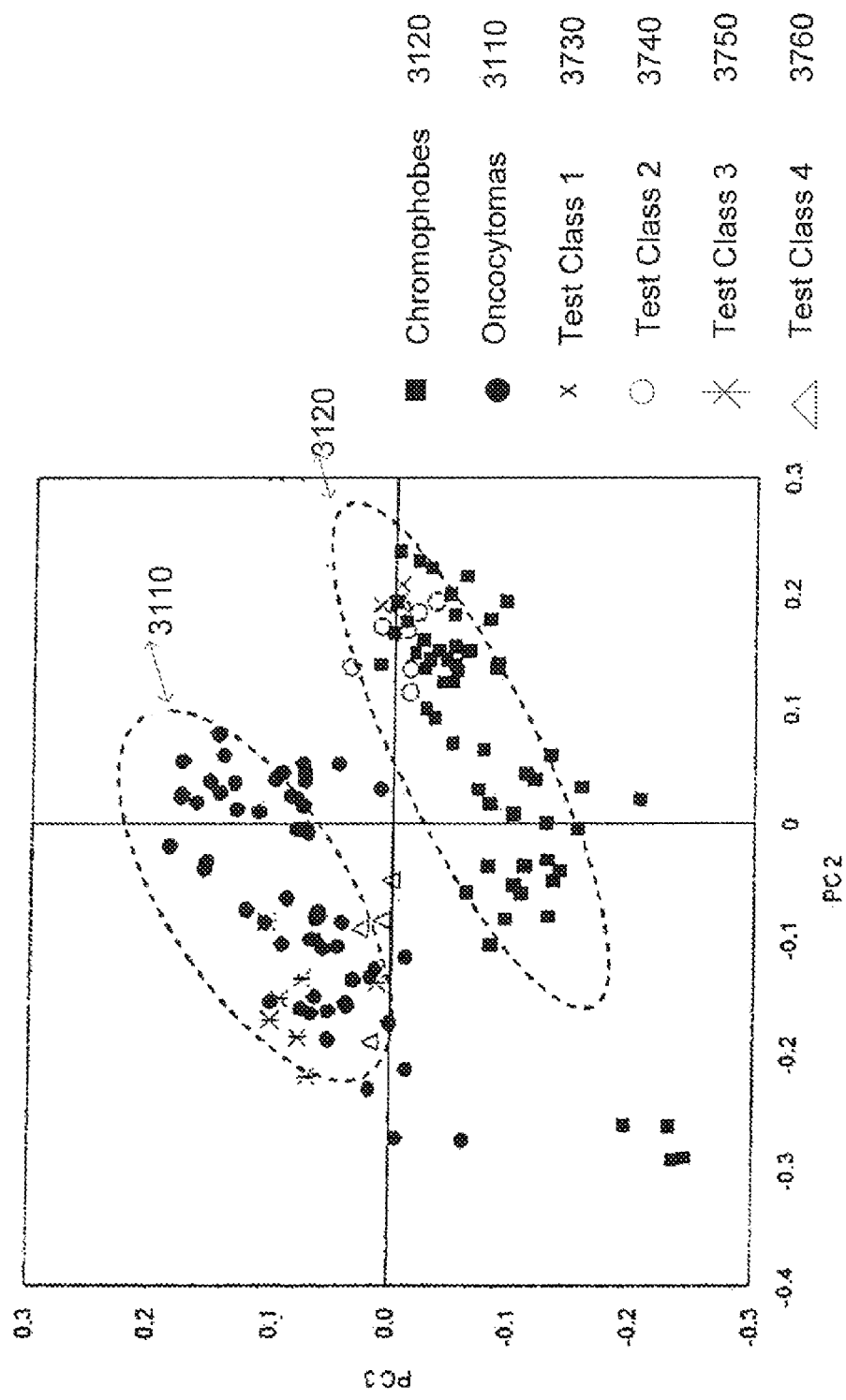
FIG. 37 illustrates the application of the classification model of FIG. 31 to four unknown renal tissue samples.

The classification model, illustrated in FIG. 34, was then used to classify four test renal samples using a total of 22 test Raman spectra obtained as described above. The test samples had been classified as two (2) OC and two (2) ChRCC based on histopathological examination. FIG. 37 shows the resulting scatter plot, which depicts the model data, as previously shown in FIG. 31, and the classification of the test data. The points labeled 3730 and 3740 correspond to samples diagnosed as ChRCC and the points labeled 3750 and 3760 correspond to samples diagnosed OC. As FIG. 37 illustrates, the model classified the data associated with the 4 cases correctly. This data indicates that Raman imaging may be used to generate a classification model to diagnose unknown renal samples as corresponding to an CC disease state or a ChRCC disease state.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed:

1. A method comprising:
   providing a database containing a plurality of reference Raman data sets, each reference Raman data set having an associated known renal sample and at least one of: an associated known metabolic state, an associated known clinical outcome, an associated known disease progression, and combinations thereof;
   irradiating a test renal sample to thereby generate a plurality of interacted photons wherein said interacted photons are selected from the group consisting of: photons scattered by said sample, photons absorbed by said sample, photons reflected by said sample, photons emitted by said sample, and combinations thereof;
   passing said plurality of interacted photons through a tunable filter;
   collecting a test Raman data set representative of said sample based on said interacted photons;
   comparing said test Raman data set to said plurality of reference Raman data sets using a chemometric technique; and
   based on said comparing, providing a determination of at least one of: a metabolic state of said sample, a clinical outcome of said sample, a disease progression of said sample, and combinations thereof.

2. The method of claim 1 wherein said disease progression is determined by identifying said sample as comprising at least one of: renal oncocytoma, chromophobe renal carcinoma, and combinations thereof.

3. The method of claim 1 wherein said plurality of reference data sets corresponds to at least one of: a plurality of reference Raman spectra, each spectrum having an associated known renal sample and at least one of: an associated known metabolic state, an associated known clinical outcome, an associated known disease progression, and combinations thereof; and a plurality of reference spatially accurate wavelength resolved Raman images, each image having a known renal sample and at least one of an associated known metabolic state, an associated known clinical outcome, an associated known disease progression, and combinations thereof.

4. The method of claim 1 wherein said test Raman data set comprises at least one of: a plurality of Raman spectra representative of said sample, a plurality of spatially accurate wavelength resolved Raman images representative of said sample, and combinations thereof.

5. The method of claim 1 wherein said chemometric technique is selected from the group consisting of: principle component analysis, partial least squares discriminate analysis, cosine correlation analysis, Euclidian distance analysis, k-means clustering, multivariate curve resolution, band t. entropy method, mahalanobis distance, adaptive subspace detector, spectral mixture resolution, and combinations thereof.

6. The method of claim 1 further comprising: obtaining said test Raman data set at a data generation site; transmitting said Raman data set over a data communication network to an analysis center; comparing said test Raman data to said reference Raman data sets at said analysis center to thereby determine at least one of the following: a metabolic state of said sample, a clinical outcome of said sample, a disease progression of said sample, and combinations thereof; and transferring said diagnosis to said data generation site via said data communication network.

7. The method of claim 1 wherein said tunable filter comprises a multi-conjugate liquid crystal tunable filter.

8. The method of claim 1 wherein said tunable filter comprises a filter selected from the group consisting of: an electro-optical tunable filter, a liquid crystal tunable filter, an acousto-optical tunable filter, Fabry Perot angle tuned filter, a Lyot filter, an Evans split element liquid crystal tunable filter, a Sole liquid crystal tunable filter, a spectral diversity filter, a photonic crystal filter, a fixed wavelength Fabry Perot tunable filter, an air-tuned Fabry Perot tunable filter, a mechanically-tuned Fabry Perot tunable filter, a liquid crystal Fabry Perot tunable filter, and combinations thereof.

9. A method comprising:
   irradiating a test renal sample to thereby generate a plurality of interacted photons wherein said interacted photons are selected from the group consisting of: photons scattered by said sample, photons absorbed by said sample, photons reflected by said sample, photons emitted by said sample, and combinations thereof;
   passing said plurality of interacted photons through a tunable filter;
   collecting a test Raman data set representative of said sample based on said interacted photons;
   analyzing said test Raman data set to thereby determine at least one of: said sample comprises renal oncocytoma disease, said sample comprises chromophobe renal carcinoma disease, and combinations thereof.

10. The method of claim 9 wherein said analyzing comprises comparing said test Raman data set to a plurality of reference Raman data sets using a chemometric technique wherein said chemometric technique is selected from the group consisting of: principle component analysis, partial least squares discriminate analysis, cosine correlation analysis, Euclidian distance analysis, k-means clustering, multivariate curve resolution, band t. entropy method, mahalanobis distance, adaptive subspace detector, spectral mixture resolution, and combinations thereof.

11. The method of claim 9 wherein said test Raman data set comprises at least one of: a plurality of Raman spectra representative of said sample, a plurality of spatially accurate wavelength resolved images representative of said sample, and combinations thereof.

12. The method of claim 10 wherein each of said plurality of reference Raman data sets comprises at least one of: a plurality of reference Raman spectra wherein each spectrum has an associated known renal sample and an associated known renal disease state, a plurality of reference spatially accurate wavelength resolved Raman images wherein each Raman image has an associated known renal sample and an associated known renal disease state, and combinations thereof.

13. The method of claim 9 wherein said tunable filter comprises a multi-conjugate liquid crystal tunable filter.

14. The method of claim 9 wherein said tunable filter comprises a filter selected from the group consisting of: an electro-optical tunable filter, a liquid crystal tunable filter, an acousto-optical tunable filter, Fabry Perot angle tuned filter, a Lyot filter, an Evans split element liquid crystal tunable filter, a Sole liquid crystal tunable filter, a spectral diversity filter, a photonic crystal filter, a fixed wavelength Fabry Perot tunable filter, an air-tuned Fabry Perot tunable filter, a mechanically-tuned Fabry Perot tunable filter, a liquid crystal Fabry Perot tunable filter, and combinations thereof.

15. A system comprising:
   as reference database comprising a plurality of reference Raman data sets wherein each reference Raman data set is associated with at least one of: a known metabolic state, a known clinical outcome, a known disease progression, and combinations thereof;
   an irradiation source configured to irradiate a test renal sample to thereby generate a plurality of interacted photons wherein said photons are selected from the group consisting of: photons scattered by said sample, photons absorbed by said sample, photons reflected by said sample, photons emitted by said sample, and combinations thereof;
   a tunable filter for filtering said plurality of interacted photons;
   a spectroscopic device configured to collect a test Raman data set from said interacted photons;
   a machine readable program code containing executable program instructions; and
   a processor operatively coupled to said irradiation source and said spectroscopic device, and configured to execute said machine, readable program code so as to perform the following: compare said test Raman data set to said plurality of reference Raman data sets using a chemometric technique, and based on said comparison determining a result wherein said result comprises at least one of: a metabolic state of said sample, clinical outcome of said sample, a disease progression of said sample, and combinations thereof.

16. The system of claim 15 further comprising: said spectroscopic device located at a data generation site; said reference Raman data base located at an analysis site; and said processor located at said data analysis site and operatively coupled to a communication interface, said processor configured to: to execute said machine readable program code so as to perform the following: facilitate transfer of said test Raman data set from said data generation site to said data analysis site via said communication interface, and transfer said result to said data generation site via said data communication network.

17. The system of claim 15 wherein said tunable filter comprises a multi-conjugate liquid crystal tunable filter.

18. The system of claim 15 wherein said tunable filter comprises a filter selected from the group consisting of: an electro-optical tunable filter, a liquid crystal tunable filter, an acousto-optical tunable filter, Fabry Perot angle tuned filter, a Lyot filter, an Evans split element liquid crystal tunable filter, a Sole liquid crystal tunable filter, a spectral diversity filter, a photonic crystal filter, a fixed wavelength Fabry Perot tunable filter, an air-tuned Fabry Perot tunable filter, a mechanically-tuned Fabry Perot tunable filter, a liquid crystal Fabry Perot tunable filter, and combinations thereof.

19. A method comprising:
providing a database containing a plurality of reference Raman data sets, each reference Raman data set having an associated known prostate sample and at least one of: an associated known disease state, an associated known metabolic state, an associated known clinical outcome, an associated known disease progression, and combinations thereof;
irradiating a test prostate sample to thereby generate a plurality of interacted photons wherein said interacted photons are selected from the group consisting of: photons scattered by said sample, photons absorbed by said sample, photons reflected by said sample, photons emitted by said sample, and combinations thereof;
passing said plurality of interacted photons through a tunable filter;
collecting a test Raman data set representative of said sample based on said interacted photons;
comparing said test Raman data set to said plurality of reference Raman data sets using a chemometric technique; and
based on said comparing, providing a determination of at least one of: a disease state of said sample, a metabolic state of said sample, a clinical outcome of said sample, a disease progression of said sample, and combinations thereof.

20. The method of claim 19 wherein said test prostate sample comprises at least one of: a Gleason 6 prostate sample, a Gleason 7 prostate sample, and combinations thereof.

21. The method of claim 19 wherein said plurality of reference data sets corresponds to at least one of: a plurality of reference Raman spectra, each spectrum having an associated known prostate sample and at least one of: an associated known disease state, an associated known metabolic state, an associated known clinical outcome, an associated known disease progression, and combinations thereof; and a plurality of reference spatially accurate wavelength resolved Raman images, each image having a known prostate sample and at least one of: an associated known disease state, an associated known metabolic state, an associated known clinical outcome, an associated known disease progression and combinations thereof.

22. The method of claim 19 wherein said test Raman data set comprises at least one of: a plurality of Raman spectra representative of said sample, a plurality of spatially accurate wavelength resolved Raman images representative of said sample, and combinations thereof.

23. The method of claim 19 wherein said wherein said chemometric technique is selected from the group consisting of: principle component analysis, partial least squares discriminate analysis, cosine correlation analysis, Euclidian distance analysis, k-means clustering, mulitivariate curve resolution, band t. entropy method, mahalanobis distance, adaptive subspace detector, spectral mixture resolution, and combinations thereof.

24. The method of claim 19 further comprising: obtaining said test Raman data set at a data generation site; transmitting said test Raman data set over a data communication network to an analysis center; determining at least one of the following at said analysis center: a disease state of said sample, it metabolic state of said sample, a clinical outcome of said sample, a disease progression of said sample, and combinations thereof; and transferring said diagnosis to said data generation site via said data communication network.

25. The method of claim 19 wherein said tunable filter comprises a multi-conjugate liquid crystal tunable filter.

26. The method of claim 19 wherein said tunable filter comprises a filter selected from the group consisting of: an electro-optical tunable filter, a liquid crystal tunable filter, an acousto-optical tunable filter, Fabry Perot angle tuned filter, a Lyot filter, an Evans split element liquid crystal tunable filter, a Sole liquid crystal tunable filter, a spectral diversity filter, a photonic crystal filter, a fixed wavelength Fabry Perot tunable filter, an air-tuned Fabry Perot tunable filter, a mechanically-tuned Fabry Perot tunable filter, a liquid crystal Fabry Perot tunable filter, and combinations thereof.

27. A system comprising:
a reference database comprising a plurality of reference Raman data sets wherein each reference Raman data set is associated with at least one of: a disease state, a known metabolic state, a known clinical outcome, a known disease progression, and combinations thereof;
an irradiation source configured to irradiate a test prostate sample to thereby generate a plurality of interacted photons wherein said photons are selected from the group consisting of: photons scattered by said sample, photons absorbed by said sample, photons reflected by said sample, photons emitted by said sample, and combinations thereof;
a tunable filter for filtering said plurality of interacted photons;
a spectroscopic device configured to collect a test Raman data set from said interacted photons;
a machine readable program code containing executable program instructions; and
a processor operatively coupled to said irradiation source and said spectroscopic device, and configured to execute said machine readable program code so as to perform the following: compare said test Raman data set to said plurality of reference Raman data sets using a chemometric technique, and based on said comparison determining a result wherein said result comprises at least one of a disease state, a metabolic state of said sample, clinical outcome of said sample, and a disease progression of said sample.

28. The system of claim 27 further comprising: obtaining said test Raman data set at a data generation site; transmitting said test Raman data set over a data communication network to an analysis center; determining at least one of the following at said analysis center: a disease state of said sample, a metabolic state of said sample, a clinical outcome of said sample, a disease progression of said sample, and combinations thereof; and transferring said result to said data generation site via said data communication network.

29. The system claim 27 wherein tunable filter comprises a multi-conjugate liquid crystal tunable filter.

30. The system of claim 27 wherein said tunable filter comprises a filter selected from the group consisting of: an electro-optical tunable filter, a liquid crystal tunable filter, an acousto-optical tunable filter, Fabry Perot angle tuned filter, a Lyot filter, an Evans split element liquid crystal tunable filter, a Sole liquid crystal tunable filter, a spectral diversity filter, a photonic crystal filter, a fixed wavelength Fabry Perot tunable filter, an air-tuned Fabry Perot tunable filter, a mechanically-tuned Fabry Perot tunable filter, a liquid crystal Fabry Perot tunable filter, and combinations thereof.

* * * * *